United States Patent
Hidaka et al.

(10) Patent No.: US 7,169,737 B2
(45) Date of Patent: Jan. 30, 2007

(54) PHENOLIC COMPOUND AND RECORDING MATERIAL USING THE SAME

(75) Inventors: Tomoya Hidaka, Ichihara (JP); Tadashi Kawakami, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 10/507,781

(22) PCT Filed: Mar. 13, 2003

(86) PCT No.: PCT/JP03/03005

§ 371 (c)(1),
(2), (4) Date: Sep. 9, 2004

(87) PCT Pub. No.: WO03/078390

PCT Pub. Date: Sep. 25, 2003

(65) Prior Publication Data

US 2005/0096222 A1 May 5, 2005

(30) Foreign Application Priority Data

| Mar. 14, 2002 | (JP) | ............................. 2002-069640 |
| Mar. 14, 2002 | (JP) | ............................. 2002-069641 |
| Mar. 14, 2002 | (JP) | ............................. 2002-069642 |
| Mar. 22, 2002 | (JP) | ............................. 2002-080021 |
| Mar. 22, 2002 | (JP) | ............................. 2002-080024 |

(51) Int. Cl.
*B41M 5/30* (2006.01)

(52) U.S. Cl. ..................... 503/216; 503/225; 568/716

(58) Field of Classification Search ............... 503/216, 503/225; 568/716, 717
See application file for complete search history.

(56) References Cited

U.S. PATENT DOCUMENTS 4,028,394 A 6/1977 Karsten et al.

(Continued)

FOREIGN PATENT DOCUMENTS

JP 49-116036 11/1974

(Continued)

OTHER PUBLICATIONS

International Search Report for PCT/JP03/03005 mailed on Jul. 29, 2003.

(Continued)

*Primary Examiner*—Bruce H. Hess
(74) *Attorney, Agent, or Firm*—Darby & Darby

(57) ABSTRACT

An object of the present invention is to provide a novel phenolic compound, and a recording material containing the same, which is excellent in storage stability. The object can be achieved by a phenolic compound represented by the formula (I):

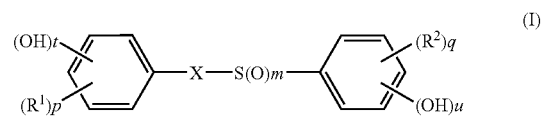

[wherein m represents an integer of 0 to 2; $R^1$ and $R^2$ each independently represents a C1–C6 alkyl group or a C1–C6 alkoxy group; p and q each independently represents an integer of 0 to 4; t and u each independently represents 0 or 1 and do not simultaneously represent 0; and X represents a group represented by any of the formulas (II) to (VII):

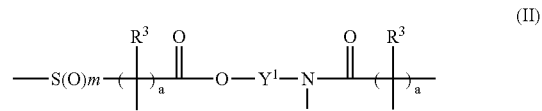

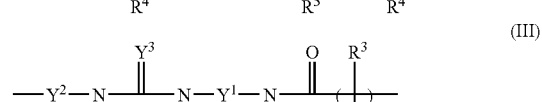

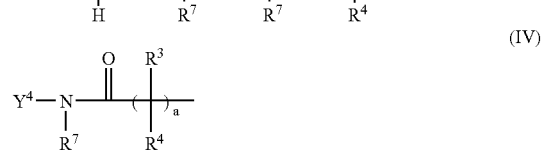

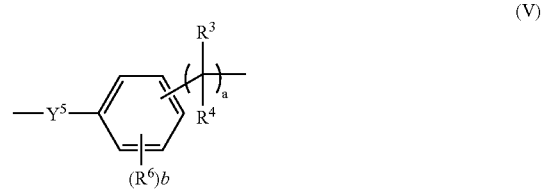

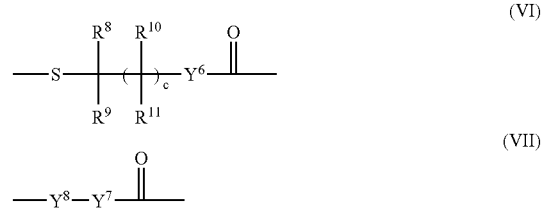

(wherein $R^3$, $R^4$, $R^5$, $R^6$, $R^7$, $R^8$, $R^9$, $R^{10}$ and $R^{11}$ each independently represents a hydrogen atom or a C1–C6 alkyl group; a represents an integer of 1 to 6; b represents an integer of 0 to 4; and c represents an integer of 0 to 6)] and a recording material containing the same.

8 Claims, No Drawings

U.S. PATENT DOCUMENTS

| | | |
|---|---|---|
| 4,508,865 A | 4/1985 | Spivack et al. |
| 4,521,320 A | 6/1985 | Spivack et al. |
| 4,552,926 A | 11/1985 | Spivack et al. |

FOREIGN PATENT DOCUMENTS

| | | |
|---|---|---|
| JP | 50-5356 | 1/1975 |
| JP | 59-165680 | 9/1984 |
| JP | 2-117889 | 5/1990 |
| JP | 02-204091 | 8/1990 |
| JP | 04-217657 | 8/1992 |
| JP | 07-025141 | 1/1995 |
| JP | 07-314894 | 12/1995 |
| JP | 08-290661 | 11/1996 |
| WO | WO-01/25193 A1 | 4/2001 |

OTHER PUBLICATIONS

Patent Abstracts of Japan for JP 10-264531 published on Oct. 6, 1998.
Patent Abstracts of Japan for JP 07-025141 published on Jan. 27, 1995.
Patent Abstracts of Japan for JP 07-149046 published on Jun. 13, 1995.
Patent Abstracts of Japan for JP 07-314894 published on Dec. 5, 1995.
Patent Abstracts of Japan for JP 02-204091 published on Aug. 14, 1990.
Patent Abstracts of Japan for JP 04-217657 published on Aug. 8, 1992.
Patent Abstracts of Japan for JP 64-072891 published on Mar. 17, 1989.

PHENOLIC COMPOUND AND RECORDING MATERIAL USING THE SAME

CROSS-REFERENCE TO PRIOR APPLICATION

This is a U.S. national phase application under 35 U.S.C. §371 of International Patent Application No. PCT/JP03/03005 filed Mar. 13, 2003, and claims the benefit of Japanese Patent Application Nos. 2002-069640 filed Mar. 14, 2002, 2002-069641 filed Mar. 14, 2002, 2002-069642 filed Mar. 14, 2002, 2002-080021 filed Mar. 22, 2002 and 2002-080024 filed Mar. 22, 2002 which are incorporated by reference herein. The International Application was published in Japanese on Mar. 13, 2003 as WO 03/078390 A1 under PCT Article 21(2).

TECHNICAL FIELD

The present invention relates to a novel phenolic compound, and to a recording material containing the same, which is excellent in storage stability.

BACKGROUND ART

Recording materials, to which the principle of color development resulting from the reaction between a color developing dye and a developer is applied, have been widely used for thermal papers for output recordings by facsimile machines, printers or the like or pressure sensitive copy papers for slip pads simultaneously transcribing multiple sheets, because these recording materials are capable of recording by using a comparatively simple recording apparatus in a short time without undergoing any troublesome procedures such as development and fixing. It is required to develop, as the recording materials described above, those which can develop color faster, retain clear whiteness of the uncolored area (hereinafter referred to as "background"), and also provide high toughness in images, especially excellent light resistance in the images in view of long-term storage stability.

2,4'-dihydroxydiphenylsulfone has conventionally been known as a developer having excellent light resistance, but was still unsatisfactory. As a method for solving these problems, Japanese Patent Application, First Publication No. Hei 8-290661 and Japanese Patent Application, First Publication No. Hei 10-264531 describe that excellent light resistance of the images is achieved by using 2,4'-dihydroxydiphenylsulfone in combination with specific dyes and coreactants. Also, Japanese Patent Application, First Publication No. Hei 7-25141, Japanese Patent Application, First Publication No. Hei 7-149046 and Japanese Patent Application, First Publication No. Hei 7-314894 describe that light resistance is improved by adding antioxidants and ultraviolet absorbers. However, these methods caused problems such as increase in manufacturing cost, various manufacturing processes, and complicated operations.

As compounds relating to the present invention, Japanese Patent Application, First Publication No. Hei 2-204091, Japanese Patent Application, First Publication No. Hei 1-72891, Japanese Patent Application, First Publication No. Hei 4-217657 and WO01/25193 disclose phenolic compounds as a developer. It is desired to develop a technique of providing an excellent recording material which exerts excellent effect on storage stability of the background and images.

DISCLOSURE OF THE INVENTION

Under these circumstances, the present invention has been made and an object thereof is to provide a recording material which is excellent in storage stability of the background and images, especially light resistance of the images.

The present invention is directed to the following:

1. A phenolic compound represented by the formula (I):

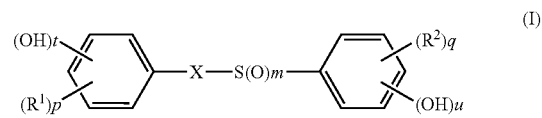

[wherein m represents an integer of 0 to 2; $R^1$ and $R^2$ each independently represents a hydroxyl group, a nitro group, a carboxyl group, a halogen atom, a C1–C6 alkyl group, a C1–C6 alkoxy group, a C1–C6 alkoxycarbonyl group, a sulfamoyl group, a phenylsulfamoyl group, a C1–C6 alkylsulfamoyl group, a di(C1–C6) alkylsulfamoyl group, a carbamoyl group, a phenylcarbamoyl group, a C1–C6 alkylcarbamoyl group, a di(C1–C6) alkylcarbamoyl group, an ureide group, a C1–C6 alkylureide group, a di(C1–C6) alkylureide group, a tri(C1–C6) alkylureide group, or a phenylureide group which may have a substituent; p and q each independently represents an integer of 0 to 4, $R^1$ may be the same or different when p is an integer of 2 or more, and $R^2$ may be the same or different when q is an integer of 2 or more; t and u each independently represents 0 or 1 and do not simultaneously represent 0; and X represents a group represented by any of the formulas (II) to (VII);

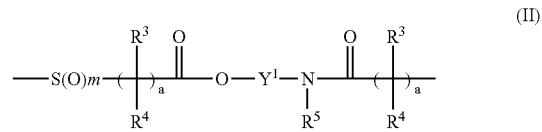

(wherein m is as defined above; $R^3$ and $R^4$ each independently represents a hydrogen atom or a C1–C6 alkyl group; a represents an integer of 1 to 6; $Y^1$ represents a C1–C6 alkylene group, or a group of the following formula:

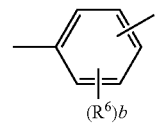

(wherein $R^6$ represents a nitro group, a halogen atom, a C1–C6 alkyl group, a C1–C6 alkoxy group, or a C1–C6 alkoxycarbonyl group; and b represents an integer of 0 to 4 and $R^6$ may be the same or different when b is an integer of 2 or more) or a group selected from the following formulas:

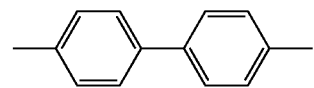

-continued

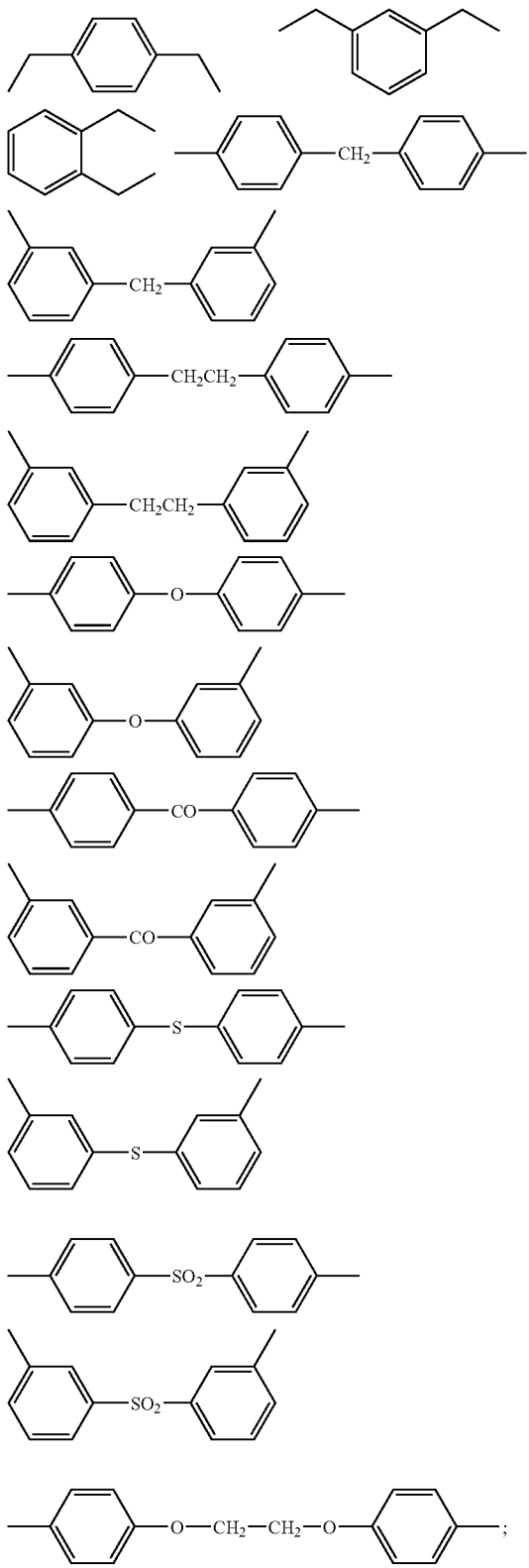

and R⁵ represents a hydrogen atom, a C1–C6 alkyl group, a phenyl group which may have a substituent, a benzyl group which may have a substituent, or the following formula:

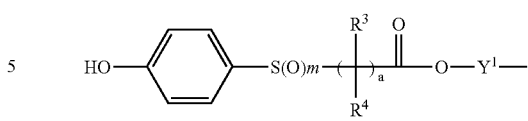

($R^3$, $R^4$, a, m and $Y^1$ are as defined above)),

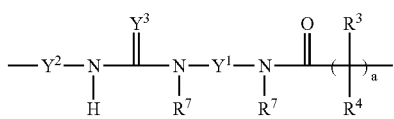

(wherein $R^3$, $R^4$, a and $Y^1$ are as defined above; $R^7$ represents a hydrogen atom, a C1–C6 alkyl group, a phenyl group which may have a substituent, or a benzyl group which may have a substituent; $Y^2$ represents a single bond, CO or $SO_2$; and $Y^3$ represents an oxygen atom or a sulfur atom),

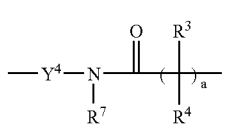

(wherein $R^3$, $R^4$, $R^7$ and a are as defined above; and $Y^4$ represents CO or $SO_2$),

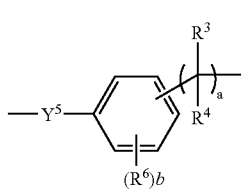

(wherein $R^3$, $R^4$, $R^6$, a and b are as defined above; and $Y^5$ represents CO or $NR^7CO$ ($R^7$ is as defined above)),

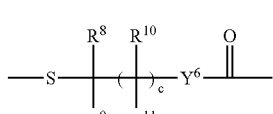

(wherein $R^8$ and $R^9$ each independently represents a hydrogen atom, a C1–C6 alkyl group, or a phenyl group which may have a substituent; $R^{10}$ and $R^{11}$ each independently represents a hydrogen atom or a C1–C6 alkyl group; c represents an integer of 0 to 6; and $Y^6$ represents a single bond or the following formula:

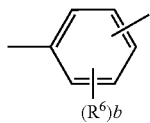

($R^6$ and b are as defined above)), and

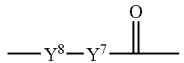

(wherein $Y^7$ represents a single bond or NH; and $Y^8$ represents a single bond or the following formula:

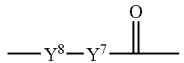

($Y^1$ and $Y^7$ are as defined above));

provided that, when X represents a group represented by the formula (VI) or (VII), m represents 0, when X represents a group represented by the formula (II) or (VI), p and q represent 0, t and u represent 1, and both of two hydroxyl groups represent a para-substituting group, when X represents a group represented by the formula (III), (IV) or (VII), q represents 0, u represents 1 and this hydroxyl group represents a para-substituting group, and when X represents a group represented by the formula (VII) and $Y^8$ represents the following formula:

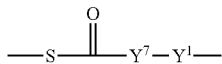

($Y^1$ and $Y^7$ are as defined above), p represents 0, t represents 1, and this hydroxyl group represents a para-substituting group;

2. The phenolic compound according to 1., wherein X is a group represented by the formula (VIII):

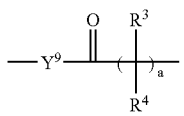

[wherein $R^3$, $R^4$ and a are as defined above; and $Y^9$ represents a group represented by any of the formulas (IX) to (XI)]:

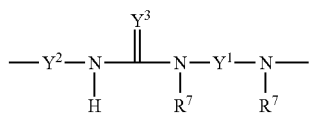

(wherein $R^3$, $R^4$, $R^5$, a, m and $Y^1$ are as defined above),

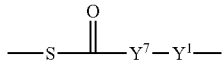

(wherein $R^7$, $Y^1$, $Y^2$ and $Y^3$ are as defined above), and

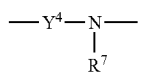

(wherein $R^7$ and $Y^4$ are as defined above)];

3. The phenolic compound according to 1., wherein the phenolic compound represented by the formula (I) is a phenolic compound represented by the formula (XII):

[wherein $R^1$, $R^2$ $R^3$ $R^4$ $R^6$, a, b, m, p, q, t, u and $Y^5$ are as defined above];

4. The phenolic compound according to 1., wherein the phenolic compound represented by the formula (I) is a phenolic compound represented by the formula (XIII):

[wherein $R^8$, $R^9$, $R^{10}$, $R^{11}$, c and $Y^6$ are as defined above];

5. The phenolic compound according to 1., wherein the phenolic compound represented by the formula (I) is a phenolic compound represented by the formula (XIV):

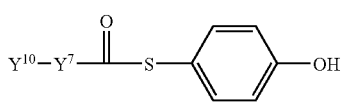

(XIV)

[wherein $Y^7$ is as defined above; and $Y^{10}$ represents the following formula:

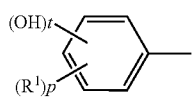

(wherein $R^1$, p and t are as defined above) or the following formula:

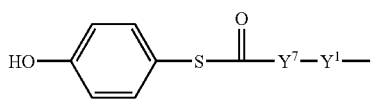

wherein $Y^1$ and $Y^7$ are as defined above)];

6. The phenolic compound according to 1., wherein the phenolic compound represented by the formula (I) is a phenolic compound represented by the formula (XV):

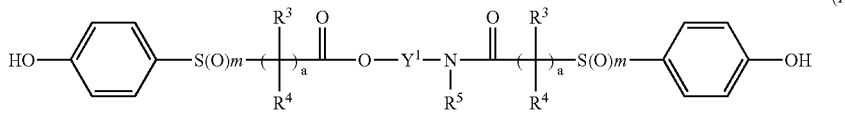

(XV)

[wherein $R^3$, $R^4$, $R^5$, a, m and $Y^1$ are as defined above];

7. The phenolic compound according to 1., wherein the phenolic compound represented by the formula (I) is a phenolic compound represented by the formula (XVI):

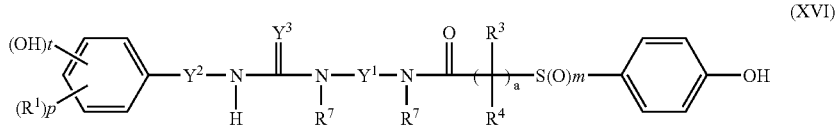

(XVI)

[wherein $R^1$, $R^3$, $R^4$, $R^7$, a, m, p, t, $Y^1$, $Y^2$ and $Y^3$ are as defined above]

8. The phenolic compound according to 1., wherein the phenolic compound represented by the formula (I) is a phenolic compound represented by the formula (XVII):

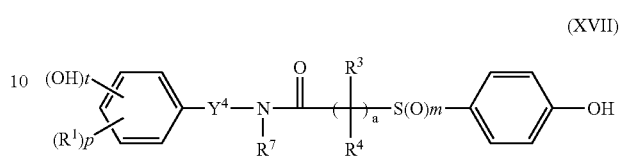

(XVII)

[wherein $R^1$, $R^3$, $R^4$, $R^7$, a, m, p, t and $Y^4$ are as defined above];

9. A recording material containing a color developing dye, comprising at least one phenolic compound represented by the formula (I):

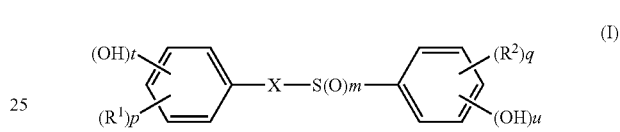

(I)

[wherein m represents an integer of 0 to 2; $R^1$ and $R^2$ each independently represents a hydroxyl group, a nitro group, a carboxyl group, a halogen atom, a C1–C6 alkyl group, a C1–C6 alkoxy group, a C1–C6 alkoxycarbonyl group, a sulfamoyl group, a phenylsulfamoyl group, a C1–C6 alkylsulfamoyl group, a di(C1–C6) alkylsulfamoyl group, a carbamoyl group, a phenylcarbamoyl group, a C1–C6 alkylcarbamoyl group, a di(C1–C6) alkylcarbamoyl group, an ureide group, a C1–C6 alkylureide group, a di(C1–C6) alkylureide group, a tri(C1–C6) alkylureide group, or a phenylureide group which may have a substituent; p and q each independently represents an integer of 0 to 4, $R^1$ may be the same or different when p is an integer of 2 or more, and $R^2$ may be the same or different when q is an integer of 2 or more; t and u each independently represents 0 or 1 and does not simultaneously represent 0; and X represents a group represented by any of the formulas (II) to (VII);

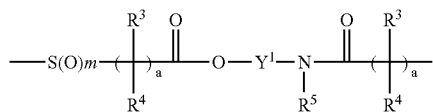
(II)

(wherein m is as defined above; R³ and R⁴ each independently represents a hydrogen atom or a C1–C6 alkyl group; a represents an integer of 1 to 6; Y¹ represents a C1–C6 alkylene group, or a group of the following formula:

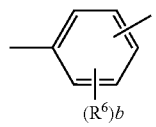

(wherein R⁶ represents a nitro group, a halogen atom, a C1–C6 alkyl group, a C1–C6 alkoxy group, or a C1–C6 alkoxycarbonyl group; and b represents an integer of 0 to 4 and R⁶ may be the same or different when b is an integer of 2 or more) or a group selected from the following formulas:

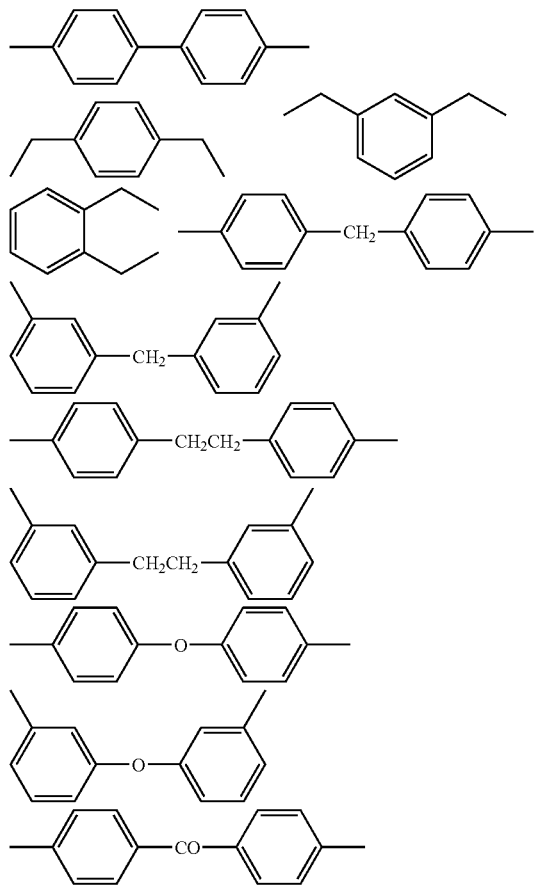

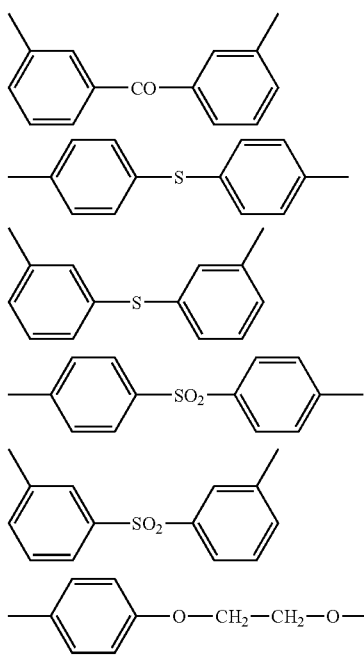

and R⁵ represents a hydrogen atom, a C1–C6 alkyl group, a phenyl group which may have a substituent, a benzyl group which may have a substituent, or the following formula:

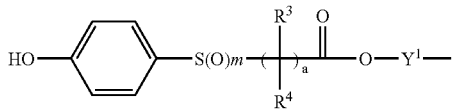

(R³, R⁴, a, m and Y¹ are as defined above)),

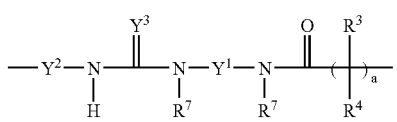
(III)

(wherein R³, R⁴, a and Y¹ are as defined above; R⁷ represents a hydrogen atom, a C1–C6 alkyl group, a phenyl group which may have a substituent, or a benzyl group which may have a substituent; Y² represents a single bond, CO or SO₂; and Y³ represents an oxygen atom or a sulfur atom),

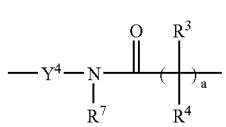
(IV)

(wherein R³, R⁴, R⁷ and a are as defined above; and Y⁴ represents CO or SO₂), (V)

$$-Y^5-\underset{(R^6)_b}{\underset{|}{\bigcirc}}\underset{R^4}{\overset{R^3}{(\ )_a}}$$

(wherein $R^3$, $R^4$, $R^6$, a and b are as defined above; and $Y^5$ represents CO or $NR^7CO$ ($R^7$ is as defined above)), (VI)

$$-S-\underset{R^9}{\overset{R^8}{\underset{|}{C}}}-(\ )_c-\underset{R^{11}}{\overset{R^{10}}{\underset{|}{C}}}-Y^6-\overset{O}{\underset{\|}{C}}-$$

(wherein $R^8$ and $R^9$ each independently represents a hydrogen atom, a C1–C6 alkyl group, or a phenyl group which may have a substituent; $R^{10}$ and $R^{11}$ each independently represents a hydrogen atom or a C1–C6 alkyl group; c represents an integer of 0 to 6; and $Y^6$ represents a single bond or the following formula:

$$-\underset{(R^6)_b}{\bigcirc}-$$

($R^6$ and b are as defined above)), and (VII)

$$-Y^8-Y^7-\overset{O}{\underset{\|}{C}}-$$

(wherein $Y^7$ represents a single bond or NH; and $Y^8$ represents a single bond or the following formula:

$$-S-\overset{O}{\underset{\|}{C}}-Y^7-Y^1-$$

($Y^1$ and $Y^7$ are as defined above));
provided that, when X represents a group represented by the formula (VI) or (VII), m represents 0,
when X represents a group represented by the formula (II) or (VI), p and q represent 0, t and u represent 1, and both of two hydroxyl groups represent a para-substituting group,
when X represents a group represented by the formula (III), (IV) or (VII), q represents 0, u represents 1 and this hydroxyl group represents a para-substituting group, and
when X represents a group represented by the formula (VII) and $Y^8$ represents the following formula:

$$-S-\overset{O}{\underset{\|}{C}}-Y^7-Y^1-$$

($Y^1$ and $Y^7$ are as defined above), p represents 0, t represents 1, and this hydroxyl group represents a para-substituting group;

10. The recording material according to 9., wherein X is a group represented by the formula (VIII):

(VIII)

$$-Y^9-\overset{O}{\underset{\|}{C}}-\underset{R^4}{\overset{R^3}{(\ )_a}}$$

[wherein $R^3$, $R^4$ and a are as defined above; and $Y^9$ represents a group represented by any of the formulas (IX) to (XI):

(IX)

$$-S(O)_m-\underset{R^4}{\overset{R^3}{(\ )_a}}-\overset{O}{\underset{\|}{C}}-O-Y^1-\underset{R^5}{\overset{}{N}}-$$

(wherein $R^3$, $R^4$, $R^5$, a, m and $Y^1$ are as defined above), (X)

$$-Y^2-\underset{H}{\overset{}{N}}-\overset{Y^3}{\underset{\|}{C}}-\underset{R^7}{\overset{}{N}}-Y^1-\underset{R^7}{\overset{}{N}}-$$

(wherein $R^7$, $Y^1$, $Y^2$ and $Y^3$ are as defined above), and (XI)

$$-Y^4-\underset{R^7}{\overset{}{N}}-$$

(wherein $R^7$ and $Y^4$ are as defined above)];

11. The recording material according to 9., wherein the phenolic compound represented by the formula (I) is a phenolic compound represented by the formula (XII):

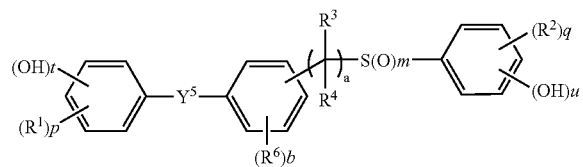

[wherein $R^1$, $R^2$, $R^3$, $R^4$, $R^6$, a, b, m, p, q, t, u and $Y^5$ are as defined above];

12. The recording material according to 9., wherein the phenolic compound represented by the formula (I) is a phenolic compound represented by the formula (XIII):

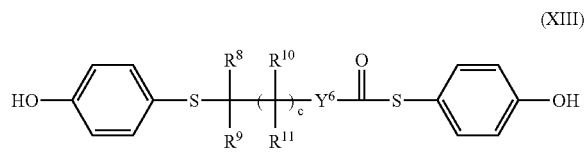

[wherein $R^8$, $R^9$, $R^{10}$, $R^{11}$, c and $Y^6$ are as defined above];

13. The recording material according to 9., wherein the phenolic compound represented by the formula (I) is a phenolic compound represented by the formula (XIV):

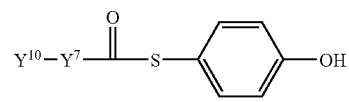

[wherein $Y^7$ are as defined above; and $Y^{10}$ represents the following formula:

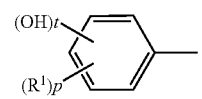

(wherein $R^1$, p and t are as defined above) or the following formula:

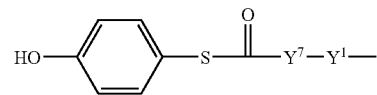

(wherein $Y^1$ and $Y^7$ are as defined above)];

14. The recording material according to 9., wherein the phenolic compound represented by the formula (I) is a phenolic compound represented by the formula (XV):

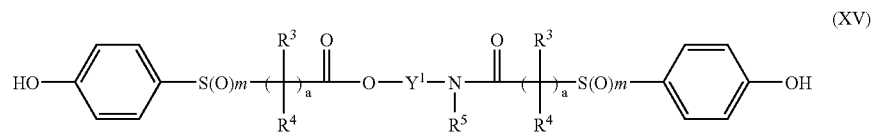

[wherein $R^1$, $R^2$, $R^3$, $R^4$, $R^5$, a, m, p, q, t, s and $Y^1$ are as defined above];

15. The recording material according to 9., wherein the phenolic compound represented by the formula (I) is a phenolic compound represented by the formula (XVI):

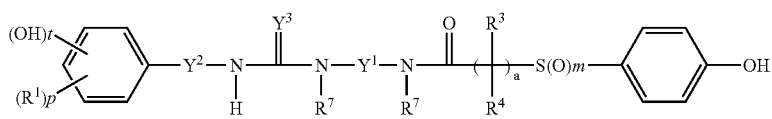

(XVI)

[wherein $R^1$, $R^3$, $R^4$, $R^7$, a, m, p, t, $Y^1$, $Y^2$ and $Y^3$ are as defined above]; and 16. The recording material according to 9., wherein the phenolic compound represented by the formula (I) is a phenolic compound represented by the formula (XVII):

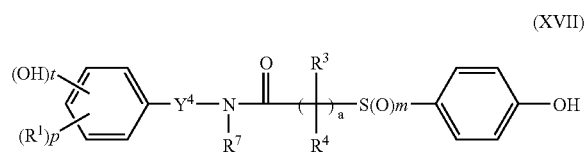

(XVII)

[wherein $R^1$, $R^3$, $R^4$, $R^7$, a, m, p, t and $Y^4$ are as defined above].

The recording material containing a phenolic compound represented by the formula (XII) of the present invention is excellent in light resistance of the images, heat resistance of the images, light resistance of the background, and heat resistance of the background; the recording material containing a phenolic compound represented by the formula (XIV) of the present invention is excellent in light resistance of the images, resistance of the images to plasticizers, resistance of the background to humidity and heat, and heat resistance of the background; the recording material containing a phenolic compound represented by the formula (XV) of the present invention is excellent in light resistance of the images, heat resistance of the images, and resistance of the background to humidity and heat; the recording material containing a phenolic compound represented by the formula (XVI) of the present invention is excellent in light resistance of the images, heat resistance of the images, and resistance of the images to plasticizers; and the recording material containing a phenolic compound represented by the formula (XVII) of the present invention is excellent in light resistance of the images, and resistance of the background to humidity and heat.

The present invention will now be described in detail.

The present invention is directed to a phenolic compound represented by the formula (I) and the phenolic compound represented by the formula (I) can be used as a developer of a recording material containing a color developing dye.

In the formula (I), $R^1$ and $R^2$ each independently represents a hydroxyl group, a nitro group, a carboxyl group, a sulfamoyl group, a carbamoyl group, a phenylsulfamoyl group, or a phenylcarbamoyl group; a halogen atom such as a fluorine atom, chlorine atom, bromine atom, or iodine atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; a C1–C6 alkoxy group such as a methoxy group, ethoxy group, n-propoxy group, isopropoxy group, n-butoxy group, sec-butoxy group, or t-butoxy group; a C1–C6 alkoxycarbonyl group such as a methoxycarbonyl group, ethoxycarbonyl group, propoxycarbonyl group, or isopropoxycarbonyl group; a C1–C6 alkylsulfamoyl group such as a methylsulfamoyl, ethylsulfamoyl, or propylsulfamoyl group; a di(C1–C6) alkylsulfamoyl group such as dimethylsulfamoyl group, diethylsulfamoyl group, or methylethylsulfamoyl group; a C1–C6 alkylcarbamoyl group such as a methylcarbamoyl group, ethylcarbamoyl group, or propylcarbamoyl group; a di(C1–C6) alkylcarbamoyl group such as dimethylcarbamoyl group, diethylcarbamoyl group, or methylethylcarbamoyl group; an ureide group; a C1–C6 alkylureide group such as N-methylureide group, N'-methylureide group, N-ethylureide group, N'-ethylureide group, N-propylureide group, N'-propylureide group, N-isopropylureide group, or N'-isopropylureide group; a di(C1–C6) alkylureide group such as N',N'-dimethylureide group, N,N'-dimethylureide group, N',N'-diethylureide group, N,N'-diethylureide group, N-methyl-N'-ethylureide group, N-ethyl-N'-methylureide group, or N',N'-methylethylureide group; a tri(C1–C6) alkylureide group such as N,N',N'-trimethylureide group, N,N',N'-triethylureide group, or N-methyl-N',N'-diethylureide group; or a phenylureide group such as N-phenylureide group, N'-phenylureide group, N',N'-diphenylureide group, N,N'-diphenylureide group, N,N',N'-triphenylureide group, N-methyl-N'-phenylureide group, N-methyl-N',N'-diphenylureide group, N-phenyl-N'-methylureide group, or N-phenyl-N',N'-dimethylureide group. The benzene ring of the phenylureide group may have a substituent and examples of the substituent include a hydroxyl group; a halogen atom such as a fluorine atom, chlorine atom, bromine atom, or iodine atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; and a C1–C6 alkoxy group such as a methoxy group, ethoxy group, n-propoxy group, isopropoxy group, n-butoxy group, sec-butoxy group, or t-butoxy group.

$R^3$, $R^4$, $R^{10}$ and $R^{11}$ each independently represents a hydrogen atom; or a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group.

$R^5$ represents a hydrogen atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; a phenyl group which may have a substituent, or a benzyl group which may have a substituent (examples of the substituent of the phenyl group and the benzyl group include a hydroxyl group; a halogen atom such as a fluorine atom, chlorine atom, bromine atom, or iodine atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; and a C1–C6 alkoxy group such as a methoxy group, ethoxy group, n-propoxy group, isopropoxy group, n-butoxy group, sec-butoxy group, or t-butoxy group); or a group represented by the following formula:

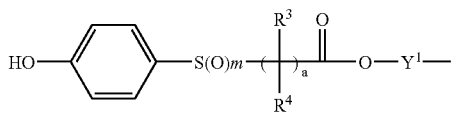

$R^6$ represents a nitro group; a halogen atom such as a fluorine atom, chlorine atom, bromine atom, or iodine atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; a C1–C6 alkoxy group such as a methoxy group, ethoxy group, n-propoxy group, isopropoxy group, n-butoxy group, sec-butoxy group, or t-butoxy group; or a C1–C6 alkoxycarbonyl group such as a methoxycarbonyl group, ethoxycarbonyl group, propoxycarbonyl group, or isopropoxycarbonyl group.

$R^7$ represents a hydrogen atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; or a phenyl group which may have a substituent, or a benzyl group which may have a substituent (examples of the substituent of the phenyl group and the benzyl group include a hydroxyl group; a halogen atom such as a fluorine atom, chlorine atom, bromine atom, or iodine atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; and a C1–C6 alkoxy group such as a methoxy group, ethoxy group, n-propoxy group, isopropoxy group, n-butoxy group, sec-butoxy group, or t-butoxy group).

$R^8$ and $R^9$ each independently represents a hydrogen atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; or a phenyl group which may have a substituent (examples of the substituent include a hydroxyl group; a halogen atom such as a fluorine atom, chlorine atom, bromine atom, or iodine atom; a C1–C6 alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group, or 2-methylpentyl group; and a C1–C6 alkoxy group such as a methoxy group, ethoxy group, n-propoxy group, isopropoxy group, n-butoxy group, sec-butoxy group, or t-butoxy group).

A general method for synthesis of a phenolic compound represented by the formula (I) of the present invention will now be described.

1) Among the phenolic compound represented by the formula (XII), of the present invention, a compound wherein m is 0 can be obtained by reacting a compound represented by the formula (1):

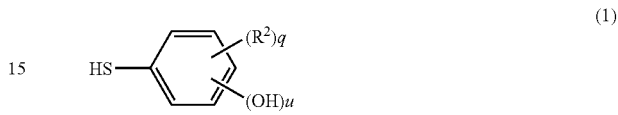

[wherein $R^2$, q and u are as defined above] with a compound represented by the formula (2):

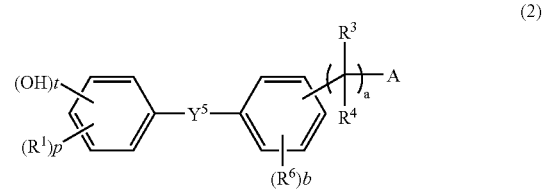

[wherein $R^1$, $R^3$, $R^4$, $R^6$, a, b, p, t and $Y^5$ are as defined above; and A represents a halogen atom such as a chlorine atom or bromine atom] in an organic solvent such as methanol in the presence of a base.

Among the phenolic compounds represented by the formula (XII) of the present invention, a compound wherein m is 1 or 2 can be obtained by oxidizing the compound obtained by the method described above in a suitable solvent using an oxidizing agent such as aqueous hydrogen peroxide or m-chloroperbenzoic acid.

Among the compounds represented by the formula (2), a compound wherein $Y^5$ is $NR^7CO$ can be obtained by reacting a compound represented by the formula (3):

[wherein $R^1$, $R^7$, p and t are as defined above] with a compound represented by the formula (4):

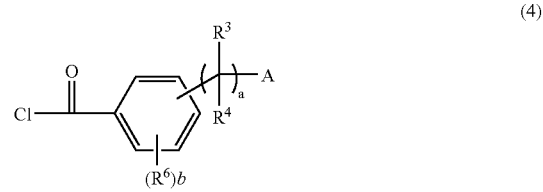

[wherein $R^3$, $R^4$, $R^6$, a, b and A are as defined above].

Among the compound represented by the formula (2), a compound wherein $Y^5$ is CO can be obtained by the Friedel-Crafts reaction between a compound represented by formula (5):

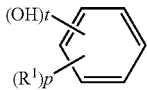
(5)

[wherein $R^1$, p and t are as defined above] and a compound represented by the formula (4).

The compounds thus synthesized are shown in Table 1 to Table 6.

2) The phenolic compound represented by the formula (XIII) of the present invention can be obtained by reacting 4-mercaptophenol with a compound represented by the formula (6):

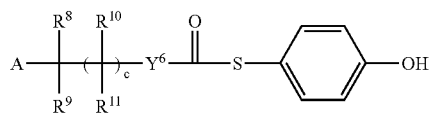
(6)

[wherein $R^8$, $R^9$, $R^{10}$, $R^{11}$, C, $Y^6$ and A are as defined above] in an organic solvent such as methanol in the presence of a base.

A compound represented by the formula (6) can be obtained by reacting 4-mercaptophenol with a compound represented by the formula (7):

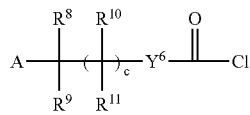
(7)

[wherein $R^8$, $R^9$, $R^{10}$, $R^{11}$, c, $Y^6$ and A are as defined above].

The compounds thus synthesized are shown in Table 7.

3) Among the phenolic compounds represented by the formula (XIV) of the present invention, a phenolic compound represented by the formula (8):

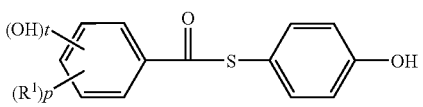
(8)

[wherein $R^1$, p and t are as defined above] can be obtained by reacting 4-mercaptophenol with a compound represented by the formula (9):

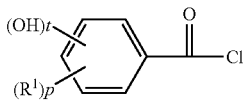
(9)

[wherein $R^1$, p and t are as defined above] in an organic solvent such as dimethoxyethane in the presence of a base.

Among the phenolic compound represented by the formula (XIV) of the present invention, a phenolic compound represented by the formula (10):

(10)

[wherein $R^1$, p and t are as defined above] can be obtained by reacting 4-mercaptophenol with a compound represented by the formula (11):

(11)

[wherein $R^1$, p and t are as defined above] in an organic solvent such as toluene.

Among the phenolic compound represented by the formula (XIV) of the present invention, a compound represented by the formula (12):

(12)

[wherein $Y^1$ is as defined above] can be obtained by reacting 4-mercaptophenol with a compound represented by the formula (13):

(13)

[wherein $Y^1$ is as defined above] in an organic solvent such as dimethoxyethane in the presence of a base.

Among the phenolic compounds represented by the formula (XIV) of the present invention, a compound represented by the formula (14):

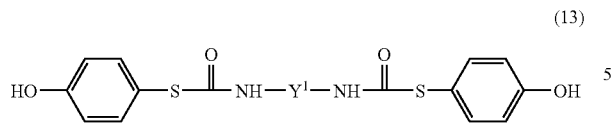
(13)

[wherein $Y^1$ is as defined above] can be obtained by reacting 4-mercaptophenol with a compound represented by the formula (15):

(15)

[wherein $Y^1$ is as defined above] in an organic solvent such as dimethoxyethane in the presence of a base.

The compounds thus synthesized are shown in Table 8 and Table 9.

4) Among the phenolic compounds represented by the formula (XV) of the present invention, a compound wherein m is 0 can be obtained by reacting a compound represented by the formula (16):

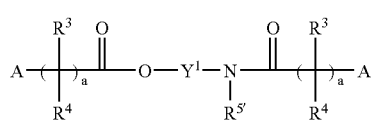
(16)

[wherein $R^3$, $R^4$, a, $Y^1$ and A are as defined above; and $R^5$ represents a hydrogen atom, a C1–C6 alkyl group, a phenyl group which may have a substituent, a benzyl group which may have a substituent, or the following formula:

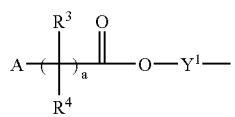

(wherein $R^3$, $R^4$, a and $Y^1$ are as defined above)] with 4-mercaptophenol in an organic solvent such as methanol in the presence of a base.

Among the phenolic compounds represented by the formula (XV) of the present invention, a compound wherein m is 1 or 2 can be obtained by oxidizing the compound obtained by the method described above in a suitable solvent using an oxidizing agent such as aqueous hydrogen peroxide or m-chloroperbenzoic acid.

A compound represented by the formula (16) can be obtained by reacting a compound represented by the formula (17):

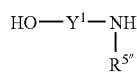
(17)

[wherein $Y^1$ is as defined above; and $R^{5''}$ represents a hydrogen atom, a C1–C6 alkyl group, a phenyl group which may have a substituent, a benzyl group which may have a substituent, or HO—$Y^1$—($Y^1$ is as defined above)] with a compound represented by the formula (18):

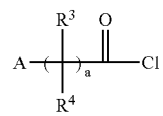
(18)

[wherein $R^3$, $R^4$, a and A are as defined above].

The compounds thus synthesized are shown in Table 10.

5) Among the phenolic compounds represented by the formula (XVI) of the present invention, a compound wherein m is 0 can be obtained by reacting a compound represented by the formula (19):

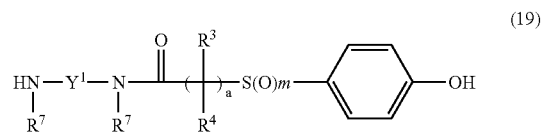
(19)

[wherein $R^3$, $R^4$, $R^7$, a, m and $Y^1$ are as defined above] with a compound represented by the formula (20):

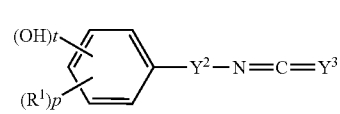
(20)

[wherein $R^1$, p, t, $Y^2$ and $Y^3$ are as defined above] in an organic solvent such as dimethoxyethane.

Among the phenolic compounds represented by the formula (XVI) of the present invention, a compound wherein m is 1 or 2 can be obtained by oxidizing the compounds obtained by the method described above in a suitable solvent using an oxidizing agent such as aqueous hydrogen peroxide or m-chloroperbenzoic acid.

A compound represented by the formula (19) can be obtained by reacting 4-mercaptophenol with a compound represented by the formula (21):

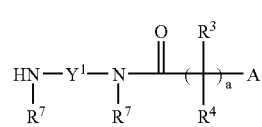
(21)

[wherein $R^3$, $R^4$, $R^7$, a, $Y^1$ and A are as defined above] in an organic solvent such as methanol in the presence of a base.

A compound represented by the formula (21) can be obtained by reacting a compound represented by the formula (22):

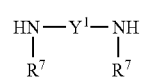
(22)

[wherein $R^7$ and $Y^1$ are as defined above] with a compound represented by the formula (23):

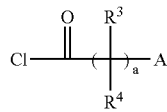
(23)

[wherein $R^3$, $R^4$, a and A are as defined above].

The compounds thus synthesized are shown in Table 11.

6) Among the phenolic compounds represented by the formula (XVII) of the present invention, a compound wherein m is 0 can be obtained by reacting 4-mercaptophenol with a compound represented by the formula (24):

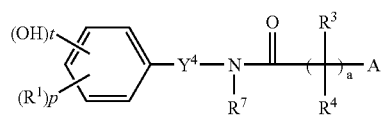
(24)

[wherein $R^1$, $R^3$, $R^4$, a, p, t, $Y^4$ and A are as defined above] in an organic solvent such as methanol in the presence of a base.

Among the phenolic compounds represented by the formula (XVII) of the present invention, a compound wherein m is 1 or 2 can be obtained by oxidizing the compound obtained by the method described above in a suitable solvent using an oxidizing agent such as aqueous hydrogen peroxide or m-chloroperbenzoic acid.

A compound represented by the formula (24) can be obtained by reacting a compound represented by the formula (25):

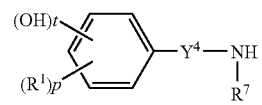
(25)

[wherein $R^1$, $R^7$, p, t and $Y^4$ are as defined above] with a compound represented by the formula (26):

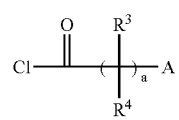
(26)

[wherein $R^3$, $R^4$, a and A are as defined above].

The compounds thus synthesized are shown in Table 12.

TABLE 1

| Compound No. | (OH)t, (R¹)p | | | | | (R⁶)b | | | | R³ | R⁴ | a | m | (OH)u, (R²)q | | | | | Melting point (°C.) |
|---|---|---|---|---|---|---|---|---|---|---|---|---|---|---|---|---|---|---|---|
| | 2- | 3- | 4- | 5- | 6- | 2'- | 3'- | 5'- | 6'- | | | | | 2"- | 3"- | 4"- | 5"- | 6"- | |
| XII-1 | H | H | H | H | H | H | H | H | H | H | H | 1 | 0 | H | H | OH | H | H | |
| XII-2 | H | H | H | H | H | H | H | H | H | H | H | 1 | 1 | H | H | OH | H | H | |
| XII-3 | H | H | H | H | H | H | H | H | H | H | H | 1 | 2 | H | H | OH | H | H | |
| XII-4 | H | H | H | H | H | H | H | H | H | H | H | 1 | 0 | OH | H | H | H | H | |
| XII-5 | H | H | OH | H | H | H | H | H | H | H | H | 1 | 0 | H | H | H | H | H | |
| XII-6 | H | H | OH | H | H | H | H | H | H | H | H | 1 | 1 | H | H | H | H | H | |
| XII-7 | H | H | OH | H | H | H | H | H | H | H | H | 1 | 2 | H | H | H | H | H | |
| XII-8 | H | OH | H | H | H | H | H | H | H | H | H | 1 | 0 | H | H | H | H | H | |
| XII-9 | H | OH | H | H | H | H | H | H | H | H | H | 1 | 1 | H | H | H | H | H | |
| XII-10 | H | OH | H | H | H | H | H | H | H | H | H | 1 | 2 | H | H | H | H | H | |
| XII-11 | OH | H | H | H | H | H | H | H | H | H | H | 1 | 0 | H | H | H | H | H | |
| XII-12 | OH | H | H | H | H | H | H | H | H | H | H | 1 | 1 | H | H | H | H | H | |
| XII-13 | OH | H | H | H | H | H | H | H | H | H | H | 1 | 2 | H | H | H | H | H | |
| XII-14 | H | H | OH | H | H | H | H | H | H | H | H | 1 | 0 | H | H | OH | H | H | |
| XII-15 | H | H | OH | H | H | H | H | H | H | H | H | 1 | 1 | H | H | OH | H | H | |
| XII-16 | H | H | OH | H | H | H | H | H | H | H | H | 1 | 2 | H | H | OH | H | H | |
| XII-17 | H | OH | H | H | H | H | H | H | H | H | H | 1 | 0 | H | H | OH | H | H | |
| XII-18 | H | OH | H | H | H | H | H | H | H | H | H | 1 | 1 | H | H | OH | H | H | |
| XII-19 | H | OH | H | H | H | H | H | H | H | H | H | 1 | 2 | H | H | OH | H | H | |
| XII-20 | OH | H | H | H | H | H | H | H | H | H | H | 1 | 0 | H | H | OH | H | H | |
| XII-21 | OH | H | H | H | H | H | H | H | H | H | H | 1 | 1 | H | H | OH | H | H | |
| XII-22 | OH | H | H | H | H | H | H | H | H | H | H | 1 | 2 | H | H | OH | H | H | |
| XII-23 | H | H | OH | H | H | H | H | H | H | H | H | 2 | 0 | H | H | OH | H | H | |
| XII-24 | H | H | OH | H | H | H | H | H | H | H | H | 2 | 1 | H | H | OH | H | H | |
| XII-25 | H | H | OH | H | H | H | H | H | H | H | H | 2 | 2 | H | H | OH | H | H | |
| XII-26 | H | OH | H | H | H | H | H | H | H | H | H | 2 | 0 | H | H | OH | H | H | |

TABLE 1-continued

| Compound No. | (OH)t, (R¹)p 2- | 3- | 4- | 5- | 6- | (R⁶)b 2'- | 3'- | 5'- | 6'- | R³ | R⁴ | a | m | (OH)u, (R²)q 2"- | 3"- | 4"- | 5"- | 6"- | Melting point (° C.) |
|---|---|---|---|---|---|---|---|---|---|---|---|---|---|---|---|---|---|---|---|
| XII-27 | H | OH | H | H | H | H | H | H | H | H | H | 2 | 1 | H | H | OH | H | H | |
| XII-28 | H | OH | H | H | H | H | H | H | H | H | H | 2 | 2 | H | H | OH | H | H | |
| XII-29 | OH | H | H | H | H | H | H | H | H | H | H | 2 | 0 | H | H | OH | H | H | |
| XII-30 | OH | H | H | H | H | H | H | H | H | H | H | 2 | 1 | H | H | OH | H | H | |
| XII-31 | OH | H | H | H | H | H | H | H | H | H | H | 2 | 2 | H | H | OH | H | H | |
| XII-32 | H | H | H | H | H | H | H | H | H | H | H | 1 | 0 | OH | H | OH | H | H | |
| XII-33 | H | H | OH | H | H | H | H | H | H | H | H | 1 | 0 | OH | H | OH | H | H | |
| XII-34 | H | OH | H | H | H | H | H | H | H | H | H | 1 | 0 | OH | H | OH | H | H | |
| XII-35 | OH | H | H | H | H | H | H | H | H | H | H | 1 | 0 | OH | H | OH | H | H | |
| XII-36 | H | H | H | H | H | H | H | H | H | CH₃ | H | 1 | 0 | H | H | OH | H | H | |
| XII-37 | H | H | H | H | H | H | H | H | H | CH₃ | H | 1 | 2 | H | H | OH | H | H | |
| XII-38 | H | H | H | H | H | H | H | H | H | CH₃ | CH₃ | 1 | 0 | H | H | OH | H | H | |
| XII-39 | H | H | H | H | H | H | H | H | H | CH₃ | CH₃ | 1 | 2 | H | H | OH | H | H | |
| XII-40 | H | H | H | H | H | CH₃ | H | H | H | H | H | 1 | 0 | H | H | OH | H | H | |
| XII-41 | H | H | H | H | H | CH₃ | H | H | H | H | H | 1 | 2 | H | H | OH | H | H | |
| XII-42 | H | H | H | H | H | H | CH₃ | H | H | H | H | 1 | 0 | H | H | OH | H | H | |
| XII-43 | H | H | H | H | H | H | CH₃ | H | H | H | H | 1 | 2 | H | H | OH | H | H | |
| XII-44 | H | H | H | H | H | Cl | H | H | H | H | H | 1 | 0 | H | H | OH | H | H | |
| XII-45 | H | H | H | H | H | Cl | H | H | H | H | H | 1 | 2 | H | H | OH | H | H | |
| XII-46 | H | H | H | H | H | H | Cl | H | H | H | H | 1 | 0 | H | H | OH | H | H | |
| XII-47 | H | H | H | H | H | H | Cl | H | H | H | H | 1 | 2 | H | H | OH | H | H | |
| XII-48 | H | H | CH₃ | H | H | H | H | H | H | H | H | 1 | 0 | H | H | OH | H | H | |
| XII-49 | H | H | CH₃ | H | H | H | H | H | H | H | H | 1 | 2 | H | H | OH | H | H | |
| XII-50 | H | CH₃ | H | H | H | H | H | H | H | H | H | 1 | 0 | H | H | OH | H | H | |
| XII-51 | H | CH₃ | H | H | H | H | H | H | H | H | H | 1 | 2 | H | H | OH | H | H | |
| XII-52 | CH₃ | H | H | H | H | H | H | H | H | H | H | 1 | 0 | H | H | OH | H | H | |
| XII-53 | CH₃ | H | H | H | H | H | H | H | H | H | H | 1 | 2 | H | H | OH | H | H | |
| XII-54 | H | H | CH₃O | H | H | H | H | H | H | H | H | 1 | 0 | H | H | OH | H | H | |
| XII-55 | H | H | CH₃O | H | H | H | H | H | H | H | H | 1 | 2 | H | H | OH | H | H | |
| XII-56 | H | CH₃O | H | H | H | H | H | H | H | H | H | 1 | 0 | H | H | OH | H | H | |
| XII-57 | H | CH₃O | H | H | H | H | H | H | H | H | H | 1 | 2 | H | H | OH | H | H | |
| XII-58 | CH₃O | H | H | H | H | H | H | H | H | H | H | 1 | 0 | H | H | OH | H | H | |
| XII-59 | CH₃O | H | H | H | H | H | H | H | H | H | H | 1 | 2 | H | H | OH | H | H | |
| XII-60 | H | H | NO₂ | H | H | H | H | H | H | H | H | 1 | 0 | H | H | OH | H | H | |
| XII-61 | H | H | NO₂ | H | H | H | H | H | H | H | H | 1 | 2 | H | H | OH | H | H | |
| XII-62 | H | NO₂ | H | H | H | H | H | H | H | H | H | 1 | 0 | H | H | OH | H | H | |
| XII-63 | H | NO₂ | H | H | H | H | H | H | H | H | H | 1 | 2 | H | H | OH | H | H | |
| XII-64 | NO₂ | H | H | H | H | H | H | H | H | H | H | 1 | 0 | H | H | OH | H | H | |
| XII-65 | NO₂ | H | H | H | H | H | H | H | H | H | H | 1 | 2 | H | H | OH | H | H | |
| XII-66 | H | H | Cl | H | H | H | H | H | H | H | H | 1 | 0 | H | H | OH | H | H | |
| XII-67 | H | H | Cl | H | H | H | H | H | H | H | H | 1 | 2 | H | H | OH | H | H | |
| XII-68 | H | Cl | H | H | H | H | H | H | H | H | H | 1 | 0 | H | H | OH | H | H | |
| XII-69 | H | Cl | H | H | H | H | H | H | H | H | H | 1 | 2 | H | H | OH | H | H | |
| XII-70 | Cl | H | H | H | H | H | H | H | H | H | H | 1 | 0 | H | H | OH | H | H | |
| XII-71 | Cl | H | H | H | H | H | H | H | H | H | H | 1 | 2 | H | H | OH | H | H | |
| XII-72 | H | CO₂CH₃ | H | H | H | H | H | H | H | H | H | 1 | 0 | H | H | OH | H | H | |
| XII-73 | H | CO₂CH₃ | H | H | H | H | H | H | H | H | H | 1 | 2 | H | H | OH | H | H | |
| XII-74 | H | CO₂H | H | H | H | H | H | H | H | H | H | 1 | 0 | H | H | OH | H | H | |
| XII-75 | H | CO₂H | H | H | H | H | H | H | H | H | H | 1 | 2 | H | H | OH | H | H | |
| XII-76 | H | SO₂NH₂ | H | H | H | H | H | H | H | H | H | 1 | 0 | H | H | OH | H | H | |
| XII-77 | H | SO₂NH₂ | H | H | H | H | H | H | H | H | H | 1 | 2 | H | H | OH | H | H | |

TABLE 2

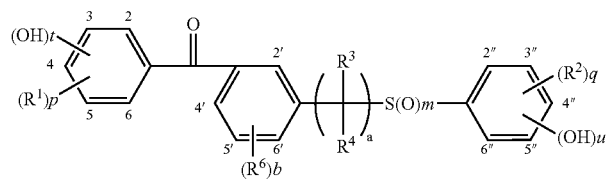

| Compound No. | (OH)t, (R¹)p 2- | 3- | 4- | 5- | 6- | 2'- | (R⁶)b 3'- | 5'- | 6'- | $R^3$ | $R^4$ | a | m | (OH)u, (R²)q 2"- | 3"- | 4"- | 5"- | 6"- | Melting point (°C.) |
|---|---|---|---|---|---|---|---|---|---|---|---|---|---|---|---|---|---|---|---|
| XII-78 | H | H | H | H | H | H | H | H | H | H | H | 1 | 0 | H | H | OH | H | H | |
| XII-79 | H | H | H | H | H | H | H | H | H | H | H | 1 | 1 | H | H | OH | H | H | |
| XII-80 | H | H | H | H | H | H | H | H | H | H | H | 1 | 2 | H | H | OH | H | H | |
| XII-81 | H | H | H | H | H | H | H | H | H | H | H | 1 | 0 | OH | H | H | H | H | |
| XII-82 | H | H | OH | H | H | H | H | H | H | H | H | 1 | 0 | H | H | H | H | H | |
| XII-83 | H | H | OH | H | H | H | H | H | H | H | H | 1 | 1 | H | H | H | H | H | |
| XII-84 | H | H | OH | H | H | H | H | H | H | H | H | 1 | 2 | H | H | H | H | H | |
| XII-85 | H | OH | H | H | H | H | H | H | H | H | H | 1 | 0 | H | H | H | H | H | |
| XII-86 | H | OH | H | H | H | H | H | H | H | H | H | 1 | 1 | H | H | H | H | H | |
| XII-87 | H | OH | H | H | H | H | H | H | H | H | H | 1 | 2 | H | H | H | H | H | |
| XII-88 | OH | H | H | H | H | H | H | H | H | H | H | 1 | 0 | H | H | H | H | H | |
| XII-89 | OH | H | H | H | H | H | H | H | H | H | H | 1 | 1 | H | H | H | H | H | |
| XII-90 | OH | H | H | H | H | H | H | H | H | H | H | 1 | 2 | H | H | H | H | H | |
| XII-91 | H | H | OH | H | H | H | H | H | H | H | H | 1 | 0 | H | H | OH | H | H | |
| XII-92 | H | H | OH | H | H | H | H | H | H | H | H | 1 | 1 | H | H | OH | H | H | |
| XII-93 | H | H | OH | H | H | H | H | H | H | H | H | 1 | 2 | H | H | OH | H | H | |
| XII-94 | H | OH | H | H | H | H | H | H | H | H | H | 1 | 0 | H | H | OH | H | H | |
| XII-95 | H | OH | H | H | H | H | H | H | H | H | H | 1 | 1 | H | H | OH | H | H | |
| XII-96 | H | OH | H | H | H | H | H | H | H | H | H | 1 | 2 | H | H | OH | H | H | |
| XII-97 | OH | H | H | H | H | H | H | H | H | H | H | 1 | 0 | H | H | OH | H | H | |
| XII-98 | OH | H | H | H | H | H | H | H | H | H | H | 1 | 1 | H | H | OH | H | H | |
| XII-99 | OH | H | H | H | H | H | H | H | H | H | H | 1 | 2 | H | H | OH | H | H | |
| XII-100 | H | H | OH | H | H | H | H | H | H | H | H | 2 | 0 | H | H | OH | H | H | |
| XII-101 | H | H | OH | H | H | H | H | H | H | H | H | 2 | 1 | H | H | OH | H | H | |
| XII-102 | H | H | OH | H | H | H | H | H | H | H | H | 2 | 2 | H | H | OH | H | H | |
| XII-103 | H | OH | H | H | H | H | H | H | H | H | H | 2 | 0 | H | H | OH | H | H | |
| XII-104 | H | OH | H | H | H | H | H | H | H | H | H | 2 | 1 | H | H | OH | H | H | |
| XII-105 | H | OH | H | H | H | H | H | H | H | H | H | 2 | 2 | H | H | OH | H | H | |
| XII-106 | OH | H | H | H | H | H | H | H | H | H | H | 2 | 0 | H | H | OH | H | H | |
| XII-107 | OH | H | H | H | H | H | H | H | H | H | H | 2 | 1 | H | H | OH | H | H | |
| XII-108 | OH | H | H | H | H | H | H | H | H | H | H | 2 | 2 | H | H | OH | H | H | |
| XII-109 | H | H | H | H | H | H | H | H | H | H | H | 1 | 0 | OH | H | OH | H | H | |
| XII-110 | H | H | OH | H | H | H | H | H | H | H | H | 1 | 0 | OH | H | OH | H | H | |
| XII-111 | H | OH | H | H | H | H | H | H | H | H | H | 1 | 0 | OH | H | OH | H | H | |
| XII-112 | OH | H | H | H | H | H | H | H | H | H | H | 1 | 0 | OH | H | OH | H | H | |
| XII-113 | H | H | H | H | H | H | H | H | H | CH₃ | H | 1 | 0 | H | H | OH | H | H | |
| XII-114 | H | H | H | H | H | H | H | H | H | CH₃ | H | 1 | 2 | H | H | OH | H | H | |
| XII-115 | H | H | H | H | H | H | H | H | H | CH₃ | CH₃ | 1 | 0 | H | H | OH | H | H | |
| XII-116 | H | H | H | H | H | H | H | H | H | CH₃ | CH₃ | 1 | 2 | H | H | OH | H | H | |
| XII-117 | H | H | H | H | H | CH₃ | H | H | H | H | H | 1 | 0 | H | H | OH | H | H | |
| XII-118 | H | H | H | H | H | CH₃ | H | H | H | H | H | 1 | 2 | H | H | OH | H | H | |
| XII-119 | H | H | H | H | H | H | CH₃ | H | H | H | H | 1 | 0 | H | H | OH | H | H | |
| XII-120 | H | H | H | H | H | H | CH₃ | H | H | H | H | 1 | 2 | H | H | OH | H | H | |
| XII-121 | H | H | H | H | H | H | H | CH₃ | H | H | H | 1 | 0 | H | H | OH | H | H | |
| XII-122 | H | H | H | H | H | H | H | CH₃ | H | H | H | 1 | 2 | H | H | OH | H | H | |
| XII-123 | H | H | H | H | H | H | H | H | CH₃ | H | H | 1 | 0 | H | H | OH | H | H | |
| XII-124 | H | H | H | H | H | H | H | H | CH₃ | H | H | 1 | 2 | H | H | OH | H | H | |
| XII-125 | H | H | H | H | H | Cl | H | H | H | H | H | 1 | 0 | H | H | OH | H | H | |
| XII-126 | H | H | H | H | H | Cl | H | H | H | H | H | 1 | 2 | H | H | OH | H | H | |
| XII-127 | H | H | H | H | H | H | Cl | H | H | H | H | 1 | 0 | H | H | OH | H | H | |
| XII-128 | H | H | H | H | H | H | Cl | H | H | H | H | 1 | 2 | H | H | OH | H | H | |
| XII-129 | H | H | H | H | H | Cl | H | Cl | H | H | H | 1 | 0 | H | H | OH | H | H | |
| XII-130 | H | H | H | H | H | Cl | H | Cl | H | H | H | 1 | 2 | H | H | OH | H | H | |
| XII-131 | H | H | H | H | H | H | H | H | Cl | H | H | 1 | 0 | H | H | OH | H | H | |
| XII-132 | H | H | H | H | H | H | H | H | Cl | H | H | 1 | 1 | H | H | OH | H | H | |
| XII-133 | H | H | CH₃ | H | H | H | H | H | H | H | H | 1 | 0 | H | H | OH | H | H | |
| XII-134 | H | H | CH₃ | H | H | H | H | H | H | H | H | 1 | 2 | H | H | OH | H | H | |
| XII-135 | H | CH₃ | H | H | H | H | H | H | H | H | H | 1 | 0 | H | H | OH | H | H | |
| XII-136 | H | CH₃ | H | H | H | H | H | H | H | H | H | 1 | 2 | H | H | OH | H | H | |
| XII-137 | CH₃ | H | H | H | H | H | H | H | H | H | H | 1 | 0 | H | H | OH | H | H | |
| XII-138 | CH₃ | H | H | H | H | H | H | H | H | H | H | 1 | 2 | H | H | OH | H | H | |
| XII-139 | H | H | CH₃O | H | H | H | H | H | H | H | H | 1 | 0 | H | H | OH | H | H | |
| XII-140 | H | H | CH₃O | H | H | H | H | H | H | H | H | 1 | 2 | H | H | OH | H | H | |
| XII-141 | H | CH₃O | H | H | H | H | H | H | H | H | H | 1 | 0 | H | H | OH | H | H | |

TABLE 2-continued

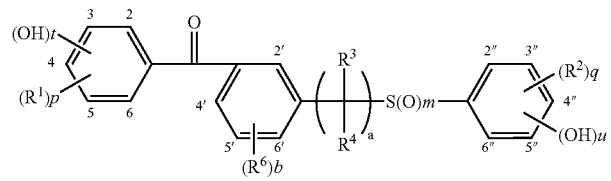

| Compound No. | (OH)t, (R¹)p 2- | 3- | 4- | 5- | 6- | 2'- | (R⁶)b 3'- | 5'- | 6'- | R³ | R⁴ | a | m | (OH)u, (R²)q 2"- | 3"- | 4"- | 5"- | 6"- | Melting point (° C.) |
|---|---|---|---|---|---|---|---|---|---|---|---|---|---|---|---|---|---|---|---|
| XII-142 | H | CH₃O | H | H | H | H | H | H | H | H | H | 1 | 2 | H | H | OH | H | H | |
| XII-143 | CH₃O | H | H | H | H | H | H | H | H | H | H | 1 | 0 | H | H | OH | H | H | |
| XII-144 | CH₃O | H | H | H | H | H | H | H | H | H | H | 1 | 2 | H | H | OH | H | H | |
| XII-145 | H | H | NO₂ | H | H | H | H | H | H | H | H | 1 | 0 | H | H | OH | H | H | |
| XII-146 | H | H | NO₂ | H | H | H | H | H | H | H | H | 1 | 2 | H | H | OH | H | H | |
| XII-147 | H | NO₂ | H | H | H | H | H | H | H | H | H | 1 | 0 | H | H | OH | H | H | |
| XII-148 | H | NO₂ | H | H | H | H | H | H | H | H | H | 1 | 2 | H | H | OH | H | H | |
| XII-149 | NO₂ | H | H | H | H | H | H | H | H | H | H | 1 | 0 | H | H | OH | H | H | |
| XII-150 | NO₂ | H | H | H | H | H | H | H | H | H | H | 1 | 2 | H | H | OH | H | H | |
| XII-151 | H | H | Cl | H | H | H | H | H | H | H | H | 1 | 0 | H | H | OH | H | H | |
| XII-152 | H | H | Cl | H | H | H | H | H | H | H | H | 1 | 2 | H | H | OH | H | H | |
| XII-153 | H | Cl | H | H | H | H | H | H | H | H | H | 1 | 0 | H | H | OH | H | H | |
| XII-154 | H | Cl | H | H | H | H | H | H | H | H | H | 1 | 2 | H | H | OH | H | H | |
| XII-155 | Cl | H | H | H | H | H | H | H | H | H | H | 1 | 0 | H | H | OH | H | H | |
| XII-156 | Cl | H | H | H | H | H | H | H | H | H | H | 1 | 2 | H | H | OH | H | H | |
| XII-157 | H | CO₂CH₃ | H | H | H | H | H | H | H | H | H | 1 | 0 | H | H | OH | H | H | |
| XII-158 | H | CO₂CH₃ | H | H | H | H | H | H | H | H | H | 1 | 2 | H | H | OH | H | H | |
| XII-159 | H | CO₂H | H | H | H | H | H | H | H | H | H | 1 | 0 | H | H | OH | H | H | |
| XII-160 | H | CO₂H | H | H | H | H | H | H | H | H | H | 1 | 2 | H | H | OH | H | H | |
| XII-161 | H | SO₂NH₂ | H | H | H | H | H | H | H | H | H | 1 | 0 | H | H | OH | H | H | |
| XII-162 | H | SO₂NH₂ | H | H | H | H | H | H | H | H | H | 1 | 2 | H | H | OH | H | H | |

TABLE 3

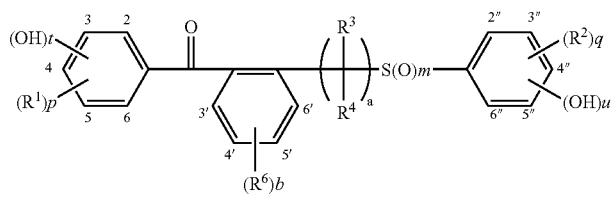

| Compound No. | (OH)t, (R¹)p 2- | 3- | 4- | 5- | 6- | 2'- | (R⁶)b 3'- | 5'- | 6'- | R³ | R⁴ | a | m | (OH)u, (R²)q 2"- | 3"- | 4"- | 5"- | 6"- | Melting point (° C.) |
|---|---|---|---|---|---|---|---|---|---|---|---|---|---|---|---|---|---|---|---|
| XII-163 | H | H | H | H | H | H | H | H | H | H | H | 1 | 0 | H | H | OH | H | H | |
| XII-164 | H | H | H | H | H | H | H | H | H | H | H | 1 | 1 | H | H | OH | H | H | |
| XII-165 | H | H | H | H | H | H | H | H | H | H | H | 1 | 2 | H | H | OH | H | H | |
| XII-166 | H | H | H | H | H | H | H | H | H | H | H | 1 | 0 | OH | H | H | H | H | |
| XII-167 | H | H | OH | H | H | H | H | H | H | H | H | 1 | 0 | H | H | H | H | H | |
| XII-168 | H | H | OH | H | H | H | H | H | H | H | H | 1 | 1 | H | H | H | H | H | |
| XII-169 | H | H | OH | H | H | H | H | H | H | H | H | 1 | 2 | H | H | H | H | H | |
| XII-170 | H | OH | H | H | H | H | H | H | H | H | H | 1 | 0 | H | H | H | H | H | |
| XII-171 | H | OH | H | H | H | H | H | H | H | H | H | 1 | 1 | H | H | H | H | H | |
| XII-172 | H | OH | H | H | H | H | H | H | H | H | H | 1 | 2 | H | H | H | H | H | |
| XII-173 | OH | H | H | H | H | H | H | H | H | H | H | 1 | 0 | H | H | H | H | H | |
| XII-174 | OH | H | H | H | H | H | H | H | H | H | H | 1 | 1 | H | H | H | H | H | |
| XII-175 | OH | H | H | H | H | H | H | H | H | H | H | 1 | 2 | H | H | H | H | H | |
| XII-176 | H | H | OH | H | H | H | H | H | H | H | H | 1 | 0 | H | H | OH | H | H | |
| XII-177 | H | H | OH | H | H | H | H | H | H | H | H | 1 | 1 | H | H | OH | H | H | |
| XII-178 | H | H | OH | H | H | H | H | H | H | H | H | 1 | 2 | H | H | OH | H | H | |
| XII-179 | H | OH | H | H | H | H | H | H | H | H | H | 1 | 0 | H | H | OH | H | H | |
| XII-180 | H | OH | H | H | H | H | H | H | H | H | H | 1 | 1 | H | H | OH | H | H | |
| XII-181 | H | OH | H | H | H | H | H | H | H | H | H | 1 | 2 | H | H | OH | H | H | |
| XII-182 | OH | H | H | H | H | H | H | H | H | H | H | 1 | 0 | H | H | OH | H | H | |
| XII-183 | OH | H | H | H | H | H | H | H | H | H | H | 1 | 1 | H | H | OH | H | H | |
| XII-184 | OH | H | H | H | H | H | H | H | H | H | H | 1 | 2 | H | H | OH | H | H | |
| XII-185 | H | H | OH | H | H | H | H | H | H | H | H | 2 | 0 | H | H | OH | H | H | |

TABLE 3-continued

| Compound No. | (OH)t, (R¹)p | | | | | (R⁶)b | | | | | | | | (OH)u, (R²)q | | | | | Melting point (° C.) |
|---|---|---|---|---|---|---|---|---|---|---|---|---|---|---|---|---|---|---|---|
| | 2- | 3- | 4- | 5- | 6- | 2'- | 3'- | 5'- | 6'- | R³ | R⁴ | a | m | 2''- | 3''- | 4''- | 5''- | 6''- | |
| XII-186 | H | H | OH | H | H | H | H | H | H | H | H | 2 | 1 | H | H | OH | H | H | |
| XII-187 | H | H | OH | H | H | H | H | H | H | H | H | 2 | 2 | H | H | OH | H | H | |
| XII-188 | H | OH | H | H | H | H | H | H | H | H | H | 2 | 0 | H | H | OH | H | H | |
| XII-189 | H | OH | H | H | H | H | H | H | H | H | H | 2 | 1 | H | H | OH | H | H | |
| XII-190 | H | OH | H | H | H | H | H | H | H | H | H | 2 | 2 | H | H | OH | H | H | |
| XII-191 | OH | H | H | H | H | H | H | H | H | H | H | 2 | 0 | H | H | OH | H | H | |
| XII-192 | OH | H | H | H | H | H | H | H | H | H | H | 2 | 1 | H | H | OH | H | H | |
| XII-193 | OH | H | H | H | H | H | H | H | H | H | H | 2 | 2 | H | H | OH | H | H | |
| XII-194 | H | H | H | H | H | H | H | H | H | H | H | 1 | 0 | OH | H | OH | H | H | |
| XII-195 | H | H | OH | H | H | H | H | H | H | H | H | 1 | 0 | OH | H | OH | H | H | |
| XII-196 | H | OH | H | H | H | H | H | H | H | H | H | 1 | 0 | OH | H | OH | H | H | |
| XII-197 | OH | H | H | H | H | H | H | H | H | H | H | 1 | 0 | OH | H | OH | H | H | |
| XII-198 | H | H | H | H | H | H | H | H | H | CH₃ | H | 1 | 0 | H | H | OH | H | H | |
| XII-199 | H | H | H | H | H | H | H | H | H | CH₃ | H | 1 | 2 | H | H | OH | H | H | |
| XII-200 | H | H | H | H | H | H | H | H | H | CH₃ | CH₃ | 1 | 0 | H | H | OH | H | H | |
| XII-201 | H | H | H | H | H | H | H | H | H | CH₃ | CH₃ | 1 | 2 | H | H | OH | H | H | |
| XII-202 | H | H | H | H | H | CH₃ | H | H | H | H | H | 1 | 0 | H | H | OH | H | H | |
| XII-203 | H | H | H | H | H | CH₃ | H | H | H | H | H | 1 | 2 | H | H | OH | H | H | |
| XII-204 | H | H | H | H | H | H | CH₃ | H | H | H | H | 1 | 0 | H | H | OH | H | H | |
| XII-205 | H | H | H | H | H | H | CH₃ | H | H | H | H | 1 | 2 | H | H | OH | H | H | |
| XII-206 | H | H | H | H | H | H | H | CH₃ | H | H | H | 1 | 0 | H | H | OH | H | H | |
| XII-207 | H | H | H | H | H | H | H | CH₃ | H | H | H | 1 | 2 | H | H | OH | H | H | |
| XII-208 | H | H | H | H | H | H | H | H | CH₃ | H | H | 1 | 0 | H | H | OH | H | H | |
| XII-209 | H | H | H | H | H | H | H | H | CH₃ | H | H | 1 | 2 | H | H | OH | H | H | |
| XII-210 | H | H | H | H | H | Cl | H | H | H | H | H | 1 | 0 | H | H | OH | H | H | |
| XII-211 | H | H | H | H | H | Cl | H | H | H | H | H | 1 | 2 | H | H | OH | H | H | |
| XII-212 | H | H | H | H | H | H | Cl | H | H | H | H | 1 | 0 | H | H | OH | H | H | |
| XII-213 | H | H | H | H | H | H | Cl | H | H | H | H | 1 | 2 | H | H | OH | H | H | |
| XII-214 | H | H | H | H | H | Cl | H | Cl | H | H | H | 1 | 0 | H | H | OH | H | H | |
| XII-215 | H | H | H | H | H | Cl | H | Cl | H | H | H | 1 | 2 | H | H | OH | H | H | |
| XII-216 | H | H | H | H | H | H | H | Cl | H | H | H | 1 | 0 | H | H | OH | H | H | |
| XII-217 | H | H | H | H | H | H | H | Cl | H | H | H | 1 | 2 | H | H | OH | H | H | |
| XII-218 | H | H | CH₃ | H | H | H | H | H | H | H | H | 1 | 0 | H | H | OH | H | H | |
| XII-219 | H | H | CH₃ | H | H | H | H | H | H | H | H | 1 | 2 | H | H | OH | H | H | |
| XII-220 | H | CH₃ | H | H | H | H | H | H | H | H | H | 1 | 0 | H | H | OH | H | H | |
| XII-221 | H | CH₃ | H | H | H | H | H | H | H | H | H | 1 | 2 | H | H | OH | H | H | |
| XII-222 | CH₃ | H | H | H | H | H | H | H | H | H | H | 1 | 0 | H | H | OH | H | H | |
| XII-223 | CH₃ | H | H | H | H | H | H | H | H | H | H | 1 | 2 | H | H | OH | H | H | |
| XII-224 | H | H | CH₃O | H | H | H | H | H | H | H | H | 1 | 0 | H | H | OH | H | H | |
| XII-225 | H | H | CH₃O | H | H | H | H | H | H | H | H | 1 | 2 | H | H | OH | H | H | |
| XII-226 | H | CH₃O | H | H | H | H | H | H | H | H | H | 1 | 0 | H | H | OH | H | H | |
| XII-227 | H | CH₃O | H | H | H | H | H | H | H | H | H | 1 | 2 | H | H | OH | H | H | |
| XII-228 | CH₃O | H | H | H | H | H | H | H | H | H | H | 1 | 0 | H | H | OH | H | H | |
| XII-229 | CH₃O | H | H | H | H | H | H | H | H | H | H | 1 | 2 | H | H | OH | H | H | |
| XII-230 | H | H | NO₂ | H | H | H | H | H | H | H | H | 1 | 0 | H | H | OH | H | H | |
| XII-231 | H | H | NO₂ | H | H | H | H | H | H | H | H | 1 | 2 | H | H | OH | H | H | |
| XII-232 | H | NO₂ | H | H | H | H | H | H | H | H | H | 1 | 0 | H | H | OH | H | H | |
| XII-233 | H | NO₂ | H | H | H | H | H | H | H | H | H | 1 | 2 | H | H | OH | H | H | |
| XII-234 | NO₂ | H | H | H | H | H | H | H | H | H | H | 1 | 0 | H | H | OH | H | H | |
| XII-235 | NO₂ | H | H | H | H | H | H | H | H | H | H | 1 | 2 | H | H | OH | H | H | |
| XII-236 | H | H | Cl | H | H | H | H | H | H | H | H | 1 | 0 | H | H | OH | H | H | |
| XII-237 | H | H | Cl | H | H | H | H | H | H | H | H | 1 | 2 | H | H | OH | H | H | |
| XII-238 | H | Cl | H | H | H | H | H | H | H | H | H | 1 | 0 | H | H | OH | H | H | |
| XII-239 | H | Cl | H | H | H | H | H | H | H | H | H | 1 | 2 | H | H | OH | H | H | |
| XII-240 | Cl | H | H | H | H | H | H | H | H | H | H | 1 | 0 | H | H | OH | H | H | |
| XII-241 | Cl | H | H | H | H | H | H | H | H | H | H | 1 | 2 | H | H | OH | H | H | |
| XII-242 | H | CO₂CH₃ | H | H | H | H | H | H | H | H | H | 1 | 0 | H | H | OH | H | H | |
| XII-243 | H | CO₂CH₃ | H | H | H | H | H | H | H | H | H | 1 | 2 | H | H | OH | H | H | |
| XII-244 | H | CO₂H | H | H | H | H | H | H | H | H | H | 1 | 0 | H | H | OH | H | H | |
| XII-245 | H | CO₂H | H | H | H | H | H | H | H | H | H | 1 | 2 | H | H | OH | H | H | |
| XII-246 | H | SO₂NH₂ | H | H | H | H | H | H | H | H | H | 1 | 0 | H | H | OH | H | H | |
| XII-247 | H | SO₂NH₂ | H | H | H | H | H | H | H | H | H | 1 | 2 | H | H | OH | H | H | |

TABLE 4

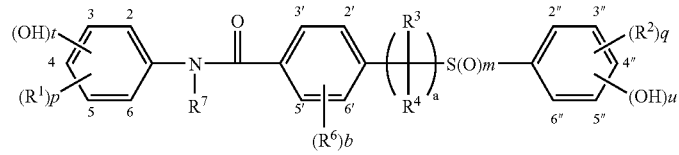

| Compound No. | (OH)t, (R¹)p 2- | 3- | 4- | 5- | 6- | (R⁶)b 2'- | 3'- | 5'- | 6'- | R⁷ | R³ | R⁴ | a | m | (OH)u, (R²)q 2"- | 3"- | 4"- | 5"- | 6"- | Melting point (°C.) |
|---|---|---|---|---|---|---|---|---|---|---|---|---|---|---|---|---|---|---|---|---|
| XII-248 | H | H | H | H | H | H | H | H | H | H | H | H | 1 | 0 | H | H | OH | H | H | 220–222 |
| XII-249 | H | H | H | H | H | H | H | H | H | H | H | H | 1 | 1 | H | H | OH | H | H | |
| XII-250 | H | H | H | H | H | H | H | H | H | H | H | H | 1 | 2 | H | H | OH | H | H | |
| XII-251 | H | H | H | H | H | H | H | H | H | H | H | H | 1 | 0 | OH | H | H | H | H | |
| XII-252 | H | H | OH | H | H | H | H | H | H | H | H | H | 1 | 0 | H | H | H | H | H | |
| XII-253 | H | H | OH | H | H | H | H | H | H | H | H | H | 1 | 1 | H | H | H | H | H | |
| XII-254 | H | H | OH | H | H | H | H | H | H | H | H | H | 1 | 2 | H | H | H | H | H | |
| XII-255 | H | OH | H | H | H | H | H | H | H | H | H | H | 1 | 0 | H | H | H | H | H | |
| XII-256 | H | OH | H | H | H | H | H | H | H | H | H | H | 1 | 1 | H | H | H | H | H | |
| XII-257 | H | OH | H | H | H | H | H | H | H | H | H | H | 1 | 2 | H | H | H | H | H | |
| XII-258 | OH | H | H | H | H | H | H | H | H | H | H | H | 1 | 0 | H | H | H | H | H | |
| XII-259 | OH | H | H | H | H | H | H | H | H | H | H | H | 1 | 1 | H | H | H | H | H | |
| XII-260 | OH | H | H | H | H | H | H | H | H | H | H | H | 1 | 2 | H | H | H | H | H | |
| XII-261 | H | H | OH | H | H | H | H | H | H | H | H | H | 1 | 0 | H | H | OH | H | H | |
| XII-262 | H | H | OH | H | H | H | H | H | H | H | H | H | 1 | 1 | H | H | OH | H | H | |
| XII-263 | H | H | OH | H | H | H | H | H | H | H | H | H | 1 | 2 | H | H | OH | H | H | |
| XII-264 | H | OH | H | H | H | H | H | H | H | H | H | H | 1 | 0 | H | H | OH | H | H | 218–222 |
| XII-265 | H | OH | H | H | H | H | H | H | H | H | H | H | 1 | 1 | H | H | OH | H | H | |
| XII-266 | H | OH | H | H | H | H | H | H | H | H | H | H | 1 | 2 | H | H | OH | H | H | |
| XII-267 | OH | H | H | H | H | H | H | H | H | H | H | H | 1 | 0 | H | H | OH | H | H | 152–156 |
| XII-268 | OH | H | H | H | H | H | H | H | H | H | H | H | 1 | 1 | H | H | OH | H | H | |
| XII-269 | OH | H | H | H | H | H | H | H | H | H | H | H | 1 | 2 | H | H | OH | H | H | 250 |
| XII-270 | H | H | OH | H | H | H | H | H | H | H | H | H | 2 | 0 | H | H | OH | H | H | |
| XII-271 | H | H | OH | H | H | H | H | H | H | H | H | H | 2 | 1 | H | H | OH | H | H | |
| XII-272 | H | H | OH | H | H | H | H | H | H | H | H | H | 2 | 2 | H | H | OH | H | H | |
| XII-273 | H | OH | H | H | H | H | H | H | H | H | H | H | 2 | 0 | H | H | OH | H | H | |
| XII-274 | H | OH | H | H | H | H | H | H | H | H | H | H | 2 | 1 | H | H | OH | H | H | |
| XII-275 | H | OH | H | H | H | H | H | H | H | H | H | H | 2 | 2 | H | H | OH | H | H | |
| XII-276 | OH | H | H | H | H | H | H | H | H | H | H | H | 2 | 0 | H | H | OH | H | H | |
| XII-277 | OH | H | H | H | H | H | H | H | H | H | H | H | 2 | 1 | H | H | OH | H | H | |
| XII-278 | OH | H | H | H | H | H | H | H | H | H | H | H | 2 | 2 | H | H | OH | H | H | |
| XII-279 | H | H | H | H | H | H | H | H | H | H | H | H | 1 | 0 | OH | H | OH | H | H | |
| XII-280 | H | H | OH | H | H | H | H | H | H | H | H | H | 1 | 0 | OH | H | H | H | H | |
| XII-281 | H | OH | H | H | H | H | H | H | H | H | H | H | 1 | 0 | OH | H | H | H | H | |
| XII-282 | OH | H | H | H | H | H | H | H | H | H | H | H | 1 | 0 | OH | H | H | H | H | |
| XII-283 | H | H | H | H | H | H | H | H | H | H | CH₃ | H | 1 | 0 | H | H | OH | H | H | |
| XII-284 | H | H | H | H | H | H | H | H | H | H | CH₃ | H | 1 | 2 | H | H | OH | H | H | |
| XII-285 | H | H | H | H | H | H | H | H | H | H | CH₃ | CH₃ | 1 | 0 | H | H | OH | H | H | |
| XII-286 | H | H | H | H | H | H | H | H | H | H | CH₃ | CH₃ | 1 | 2 | H | H | OH | H | H | |
| XII-287 | H | H | H | H | H | CH₃ | H | H | H | H | H | H | 1 | 0 | H | H | OH | H | H | |
| XII-288 | H | H | H | H | H | CH₃ | H | H | H | H | H | H | 1 | 2 | H | H | OH | H | H | |
| XII-289 | H | H | H | H | H | H | CH₃ | H | H | H | H | H | 1 | 0 | H | H | OH | H | H | |
| XII-290 | H | H | H | H | H | H | CH₃ | H | H | H | H | H | 1 | 2 | H | H | OH | H | H | |
| XII-291 | H | H | H | H | H | Cl | H | H | H | H | H | H | 1 | 0 | H | H | OH | H | H | |
| XII-292 | H | H | H | H | H | Cl | H | H | H | H | H | H | 1 | 2 | H | H | OH | H | H | |
| XII-293 | H | H | H | H | H | H | Cl | H | H | H | H | H | 1 | 0 | H | H | OH | H | H | |
| XII-294 | H | H | H | H | H | H | Cl | H | H | H | H | H | 1 | 2 | H | H | OH | H | H | |
| XII-295 | H | H | CH₃ | H | H | H | H | H | H | H | H | H | 1 | 0 | H | H | OH | H | H | |
| XII-296 | H | H | CH₃ | H | H | H | H | H | H | H | H | H | 1 | 2 | H | H | OH | H | H | |
| XII-297 | H | CH₃ | H | H | H | H | H | H | H | H | H | H | 1 | 0 | H | H | OH | H | H | 176–177 |
| XII-298 | H | CH₃ | H | H | H | H | H | H | H | H | H | H | 1 | 2 | H | H | OH | H | H | |
| XII-299 | CH₃ | H | H | H | H | H | H | H | H | H | H | H | 1 | 0 | H | H | OH | H | H | |
| XII-300 | CH₃ | H | H | H | H | H | H | H | H | H | H | H | 1 | 2 | H | H | OH | H | H | |
| XII-301 | H | H | CH₃O | H | H | H | H | H | H | H | H | H | 1 | 0 | H | H | OH | H | H | 233–234 |
| XII-302 | H | H | CH₃O | H | H | H | H | H | H | H | H | H | 1 | 2 | H | H | OH | H | H | |
| XII-303 | H | CH₃O | H | H | H | H | H | H | H | H | H | H | 1 | 0 | H | H | OH | H | H | 145–147 |
| XII-304 | H | CH₃O | H | H | H | H | H | H | H | H | H | H | 1 | 2 | H | H | OH | H | H | |
| XII-305 | CH₃O | H | H | H | H | H | H | H | H | H | H | H | 1 | 0 | H | H | OH | H | H | |
| XII-306 | CH₃O | H | H | H | H | H | H | H | H | H | H | H | 1 | 2 | H | H | OH | H | H | |
| XII-307 | H | H | NO₂ | H | H | H | H | H | H | H | H | H | 1 | 0 | H | H | OH | H | H | |
| XII-308 | H | H | NO₂ | H | H | H | H | H | H | H | H | H | 1 | 2 | H | H | OH | H | H | |
| XII-309 | H | NO₂ | H | H | H | H | H | H | H | H | H | H | 1 | 0 | H | H | OH | H | H | |
| XII-310 | H | NO₂ | H | H | H | H | H | H | H | H | H | H | 1 | 2 | H | H | OH | H | H | |
| XII-311 | NO₂ | H | H | H | H | H | H | H | H | H | H | H | 1 | 0 | H | H | OH | H | H | |
| XII-312 | NO₂ | H | H | H | H | H | H | H | H | H | H | H | 1 | 2 | H | H | OH | H | H | |

TABLE 4-continued

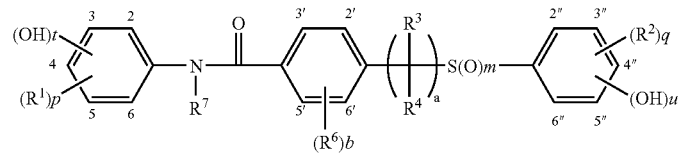

| Compound No. | (OH)t, (R¹)p 2- | 3- | 4- | 5- | 6- | (R⁶)b 2'- | 3'- | 5'- | 6'- | R⁷ | R³ | R⁴ | a | m | (OH)u, (R²)q 2"- | 3"- | 4"- | 5"- | 6"- | Melting point (°C.) |
|---|---|---|---|---|---|---|---|---|---|---|---|---|---|---|---|---|---|---|---|---|
| XII-313 | H | H | Cl | H | H | H | H | H | H | H | H | H | 1 | 0 | H | H | OH | H | H | |
| XII-314 | H | H | Cl | H | H | H | H | H | H | H | H | H | 1 | 2 | H | H | OH | H | H | |
| XII-315 | H | Cl | H | H | H | H | H | H | H | H | H | H | 1 | 0 | H | H | OH | H | H | |
| XII-316 | H | Cl | H | H | H | H | H | H | H | H | H | H | 1 | 2 | H | H | OH | H | H | |
| XII-317 | Cl | H | H | H | H | H | H | H | H | H | H | H | 1 | 0 | H | H | OH | H | H | |
| XII-318 | Cl | H | H | H | H | H | H | H | H | H | H | H | 1 | 2 | H | H | OH | H | H | |
| XII-319 | H | H | H | H | H | H | H | H | H | CH₃ | H | H | 1 | 0 | H | H | OH | H | H | |
| XII-320 | H | H | H | H | H | H | H | H | H | CH₃ | H | H | 1 | 2 | H | H | OH | H | H | |
| XII-321 | H | H | H | H | H | H | H | H | H | Ph | H | H | 1 | 0 | H | H | OH | H | H | |
| XII-322 | H | H | H | H | H | H | H | H | H | Ph | H | H | 1 | 2 | H | H | OH | H | H | |
| XII-323 | H | H | H | H | H | H | H | H | H | CH₂Ph | H | H | 1 | 0 | H | H | OH | H | H | |
| XII-324 | H | H | H | H | H | H | H | H | H | CH₂Ph | H | H | 1 | 2 | H | H | OH | H | H | |
| XII-325 | H | CO₂CH₃ | H | H | H | H | H | H | H | H | H | H | 1 | 0 | H | H | OH | H | H | |
| XII-326 | H | CO₂CH₃ | H | H | H | H | H | H | H | H | H | H | 1 | 2 | H | H | OH | H | H | |
| XII-327 | H | CO₂H | H | H | H | H | H | H | H | H | H | H | 1 | 0 | H | H | OH | H | H | |
| XII-328 | H | CO₂H | H | H | H | H | H | H | H | H | H | H | 1 | 2 | H | H | OH | H | H | |
| XII-329 | H | SO₂NH₂ | H | H | H | H | H | H | H | H | H | H | 1 | 0 | H | H | OH | H | H | |
| XII-330 | H | SO₂NH₂ | H | H | H | H | H | H | H | H | H | H | 1 | 2 | H | H | OH | H | H | |
| XII-331 | H | OH | CH₃ | H | H | H | H | H | H | H | H | H | 1 | 0 | H | H | OH | H | H | 211–214 |
| XII-332 | H | OH | CH₃ | H | H | H | H | H | H | H | H | H | 1 | 2 | H | H | OH | H | H | |
| XII-333 | CH₃ | H | CH₃O | H | H | H | H | H | H | H | H | H | 1 | 0 | H | H | OH | H | H | 167–168 |
| XII-334 | CH₃ | H | CH₃O | H | H | H | H | H | H | H | H | H | 1 | 2 | H | H | OH | H | H | |

TABLE 5

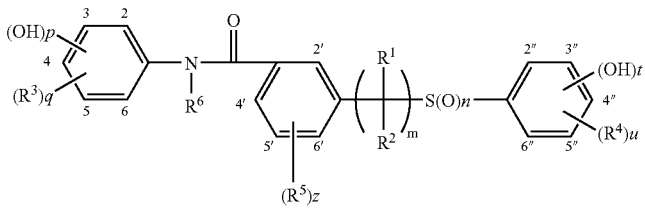

| Compound No. | (OH)t, (R¹)p 2- | 3- | 4- | 5- | 6- | (R⁶)b 2'- | 3'- | 5'- | 6'- | R⁷ | R³ | R⁴ | a | m | (OH)u, (R²)q 2"- | 3"- | 4"- | 5"- | 6"- | Melting point (°C.) |
|---|---|---|---|---|---|---|---|---|---|---|---|---|---|---|---|---|---|---|---|---|
| XII-335 | H | H | H | H | H | H | H | H | H | H | H | H | 1 | 0 | H | H | OH | H | H | |
| XII-336 | H | H | H | H | H | H | H | H | H | H | H | H | 1 | 1 | H | H | OH | H | H | |
| XII-337 | H | H | H | H | H | H | H | H | H | H | H | H | 1 | 2 | H | H | OH | H | H | |
| XII-338 | H | H | H | H | H | H | H | H | H | H | H | H | 1 | 0 | OH | H | H | H | H | |
| XII-339 | H | H | OH | H | H | H | H | H | H | H | H | H | 1 | 0 | H | H | H | H | H | |
| XII-340 | H | H | OH | H | H | H | H | H | H | H | H | H | 1 | 1 | H | H | H | H | H | |
| XII-341 | H | H | OH | H | H | H | H | H | H | H | H | H | 1 | 2 | H | H | H | H | H | |
| XII-342 | H | OH | H | H | H | H | H | H | H | H | H | H | 1 | 0 | H | H | H | H | H | |
| XII-343 | H | OH | H | H | H | H | H | H | H | H | H | H | 1 | 1 | H | H | H | H | H | |
| XII-344 | H | OH | H | H | H | H | H | H | H | H | H | H | 1 | 2 | H | H | H | H | H | |
| XII-345 | OH | H | H | H | H | H | H | H | H | H | H | H | 1 | 0 | H | H | H | H | H | |
| XII-346 | OH | H | H | H | H | H | H | H | H | H | H | H | 1 | 1 | H | H | H | H | H | |
| XII-347 | OH | H | H | H | H | H | H | H | H | H | H | H | 1 | 2 | H | H | H | H | H | |
| XII-348 | H | H | OH | H | H | H | H | H | H | H | H | H | 1 | 0 | H | H | OH | H | H | |
| XII-349 | H | H | OH | H | H | H | H | H | H | H | H | H | 1 | 1 | H | H | OH | H | H | |
| XII-350 | H | H | OH | H | H | H | H | H | H | H | H | H | 1 | 2 | H | H | OH | H | H | |
| XII-351 | H | OH | H | H | H | H | H | H | H | H | H | H | 1 | 0 | H | H | OH | H | H | |
| XII-352 | H | OH | H | H | H | H | H | H | H | H | H | H | 1 | 1 | H | H | OH | H | H | |
| XII-353 | H | OH | H | H | H | H | H | H | H | H | H | H | 1 | 2 | H | H | OH | H | H | |
| XII-354 | OH | H | H | H | H | H | H | H | H | H | H | H | 1 | 0 | H | H | OH | H | H | |
| XII-355 | OH | H | H | H | H | H | H | H | H | H | H | H | 1 | 1 | H | H | OH | H | H | |
| XII-356 | OH | H | H | H | H | H | H | H | H | H | H | H | 1 | 2 | H | H | OH | H | H | |

TABLE 5-continued

| Compound No. | (OH)t, (R¹)p 2- | 3- | 4- | 5- | 6- | (R⁶)b 2'- | 3'- | 5'- | 6'- | R⁷ | R³ | R⁴ | a | m | (OH)u, (R²)q 2''- | 3''- | 4''- | 5''- | 6''- | Melting point (°C.) |
|---|---|---|---|---|---|---|---|---|---|---|---|---|---|---|---|---|---|---|---|---|
| XII-357 | H | H | OH | H | H | H | H | H | H | H | H | H | 2 | 0 | H | H | OH | H | H | |
| XII-358 | H | H | OH | H | H | H | H | H | H | H | H | H | 2 | 1 | H | H | OH | H | H | |
| XII-359 | H | H | OH | H | H | H | H | H | H | H | H | H | 2 | 2 | H | H | OH | H | H | |
| XII-360 | H | OH | H | H | H | H | H | H | H | H | H | H | 2 | 0 | H | H | OH | H | H | |
| XII-361 | H | OH | H | H | H | H | H | H | H | H | H | H | 2 | 1 | H | H | OH | H | H | |
| XII-362 | H | OH | H | H | H | H | H | H | H | H | H | H | 2 | 2 | H | H | OH | H | H | |
| XII-363 | OH | H | H | H | H | H | H | H | H | H | H | H | 2 | 0 | H | H | OH | H | H | |
| XII-364 | OH | H | H | H | H | H | H | H | H | H | H | H | 2 | 1 | H | H | OH | H | H | |
| XII-365 | OH | H | H | H | H | H | H | H | H | H | H | H | 2 | 2 | H | H | OH | H | H | |
| XII-366 | H | H | H | H | H | H | H | H | H | H | H | H | 1 | 0 | H | H | OH | H | H | |
| XII-367 | H | H | OH | H | H | H | H | H | H | H | H | H | 1 | 0 | OH | H | OH | H | H | |
| XII-368 | H | OH | H | H | H | H | H | H | H | H | H | H | 1 | 0 | OH | H | OH | H | H | |
| XII-369 | OH | H | H | H | H | H | H | H | H | H | H | H | 1 | 0 | OH | H | OH | H | H | |
| XII-370 | H | H | H | H | H | H | H | H | H | H | CH₃ | H | 1 | 0 | H | H | OH | H | H | |
| XII-371 | H | H | H | H | H | H | H | H | H | H | CH₃ | H | 1 | 2 | H | H | OH | H | H | |
| XII-372 | H | H | H | H | H | H | H | H | H | H | CH₃ | CH₃ | 1 | 0 | H | H | OH | H | H | |
| XII-373 | H | H | H | H | H | H | H | H | H | H | CH₃ | CH₃ | 1 | 2 | H | H | OH | H | H | |
| XII-374 | H | H | H | H | H | CH₃ | H | H | H | H | H | H | 1 | 0 | H | H | OH | H | H | |
| XII-375 | H | H | H | H | H | CH₃ | H | H | H | H | H | H | 1 | 2 | H | H | OH | H | H | |
| XII-376 | H | H | H | H | H | H | CH₃ | H | H | H | H | H | 1 | 0 | H | H | OH | H | H | |
| XII-377 | H | H | H | H | H | H | CH₃ | H | H | H | H | H | 1 | 2 | H | H | OH | H | H | |
| XII-378 | H | H | H | H | H | H | H | CH₃ | H | H | H | H | 1 | 0 | H | H | OH | H | H | |
| XII-379 | H | H | H | H | H | H | H | CH₃ | H | H | H | H | 1 | 2 | H | H | OH | H | H | |
| XII-380 | H | H | H | H | H | H | H | H | CH₃ | H | H | H | 1 | 0 | H | H | OH | H | H | |
| XII-381 | H | H | H | H | H | H | H | H | CH₃ | H | H | H | 1 | 2 | H | H | OH | H | H | |
| XII-382 | H | H | H | H | H | Cl | H | H | H | H | H | H | 1 | 0 | H | H | OH | H | H | |
| XII-383 | H | H | H | H | H | Cl | H | H | H | H | H | H | 1 | 2 | H | H | OH | H | H | |
| XII-384 | H | H | H | H | H | H | Cl | H | H | H | H | H | 1 | 0 | H | H | OH | H | H | |
| XII-385 | H | H | H | H | H | H | Cl | H | H | H | H | H | 1 | 2 | H | H | OH | H | H | |
| XII-386 | H | H | H | H | H | Cl | H | Cl | H | H | H | H | 1 | 0 | H | H | OH | H | H | |
| XII-387 | H | H | H | H | H | Cl | H | Cl | H | H | H | H | 1 | 2 | H | H | OH | H | H | |
| XII-388 | H | H | H | H | H | H | H | H | Cl | H | H | H | 1 | 0 | H | H | OH | H | H | |
| XII-389 | H | H | H | H | H | H | H | H | Cl | H | H | H | 1 | 2 | H | H | OH | H | H | |
| XII-390 | H | H | CH₃ | H | H | H | H | H | H | H | H | H | 1 | 0 | H | H | OH | H | H | |
| XII-391 | H | H | CH₃ | H | H | H | H | H | H | H | H | H | 1 | 2 | H | H | OH | H | H | |
| XII-392 | H | CH₃ | H | H | H | H | H | H | H | H | H | H | 1 | 0 | H | H | OH | H | H | |
| XII-393 | H | CH₃ | H | H | H | H | H | H | H | H | H | H | 1 | 2 | H | H | OH | H | H | |
| XII-394 | CH₃ | H | H | H | H | H | H | H | H | H | H | H | 1 | 0 | H | H | OH | H | H | |
| XII-395 | CH₃ | H | H | H | H | H | H | H | H | H | H | H | 1 | 2 | H | H | OH | H | H | |
| XII-396 | H | H | CH₃O | H | H | H | H | H | H | H | H | H | 1 | 0 | H | H | OH | H | H | |
| XII-397 | H | H | CH₃O | H | H | H | H | H | H | H | H | H | 1 | 2 | H | H | OH | H | H | |
| XII-398 | H | CH₃O | H | H | H | H | H | H | H | H | H | H | 1 | 0 | H | H | OH | H | H | |
| XII-399 | H | CH₃O | H | H | H | H | H | H | H | H | H | H | 1 | 2 | H | H | OH | H | H | |
| XII-400 | CH₃O | H | H | H | H | H | H | H | H | H | H | H | 1 | 0 | H | H | OH | H | H | |
| XII-401 | CH₃O | H | H | H | H | H | H | H | H | H | H | H | 1 | 2 | H | H | OH | H | H | |
| XII-402 | H | H | NO₂ | H | H | H | H | H | H | H | H | H | 1 | 0 | H | H | OH | H | H | |
| XII-403 | H | H | NO₂ | H | H | H | H | H | H | H | H | H | 1 | 2 | H | H | OH | H | H | |
| XII-404 | H | NO₂ | H | H | H | H | H | H | H | H | H | H | 1 | 0 | H | H | OH | H | H | |
| XII-405 | H | NO₂ | H | H | H | H | H | H | H | H | H | H | 1 | 2 | H | H | OH | H | H | |
| XII-406 | NO₂ | H | H | H | H | H | H | H | H | H | H | H | 1 | 0 | H | H | OH | H | H | |
| XII-407 | NO₂ | H | H | H | H | H | H | H | H | H | H | H | 1 | 2 | H | H | OH | H | H | |
| XII-408 | H | H | Cl | H | H | H | H | H | H | H | H | H | 1 | 0 | H | H | OH | H | H | |
| XII-409 | H | H | Cl | H | H | H | H | H | H | H | H | H | 1 | 2 | H | H | OH | H | H | |
| XII-410 | H | Cl | H | H | H | H | H | H | H | H | H | H | 1 | 0 | H | H | OH | H | H | |
| XII-411 | H | Cl | H | H | H | H | H | H | H | H | H | H | 1 | 2 | H | H | OH | H | H | |
| XII-412 | Cl | H | H | H | H | H | H | H | H | H | H | H | 1 | 0 | H | H | OH | H | H | |
| XII-413 | Cl | H | H | H | H | H | H | H | H | H | H | H | 1 | 2 | H | H | OH | H | H | |
| XII-414 | H | H | H | H | H | H | H | H | H | CH₃ | H | H | 1 | 0 | H | H | OH | H | H | |
| XII-415 | H | H | H | H | H | H | H | H | H | CH₃ | H | H | 1 | 2 | H | H | OH | H | H | |
| XII-416 | H | H | H | H | H | H | H | H | H | Ph | H | H | 1 | 0 | H | H | OH | H | H | |
| XII-417 | H | H | H | H | H | H | H | H | H | Ph | H | H | 1 | 2 | H | H | OH | H | H | |
| XII-418 | H | H | H | H | H | H | H | H | H | CH₂Ph | H | H | 1 | 0 | H | H | OH | H | H | |
| XII-419 | H | H | H | H | H | H | H | H | H | CH₂Ph | H | H | 1 | 2 | H | H | OH | H | H | |

TABLE 5-continued

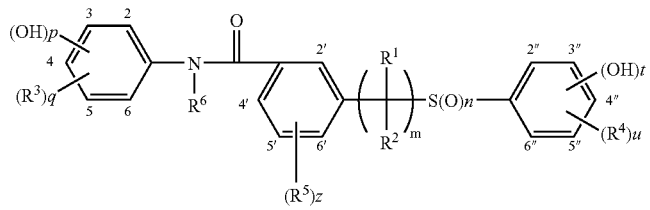

| Compound No. | (OH)t, (R¹)p | | | | | (R⁶)b | | | | | | | | a | m | (OH)u, (R²)q | | | | | Melting point (° C.) |
|---|---|---|---|---|---|---|---|---|---|---|---|---|---|---|---|---|---|---|---|---|---|
| | 2- | 3- | 4- | 5- | 6- | 2'- | 3'- | 5'- | 6'- | R⁷ | R³ | R⁴ | | | | 2"- | 3"- | 4"- | 5"- | 6"- | |
| XII-420 | H | CO₂CH₃ | H | H | H | H | H | H | H | H | H | H | 1 | 0 | H | H | OH | H | H | |
| XII-421 | H | CO₂CH₃ | H | H | H | H | H | H | H | H | H | H | 1 | 2 | H | H | OH | H | H | |
| XII-422 | H | CO₂H | H | H | H | H | H | H | H | H | H | H | 1 | 0 | H | H | OH | H | H | |
| XII-423 | H | CO₂H | H | H | H | H | H | H | H | H | H | H | 1 | 2 | H | H | OH | H | H | |
| XII-424 | H | SO₂NH₂ | H | H | H | H | H | H | H | H | H | H | 1 | 0 | H | H | OH | H | H | |
| XII-425 | H | SO₂NH₂ | H | H | H | H | H | H | H | H | H | H | 1 | 2 | H | H | OH | H | H | |

TABLE 6

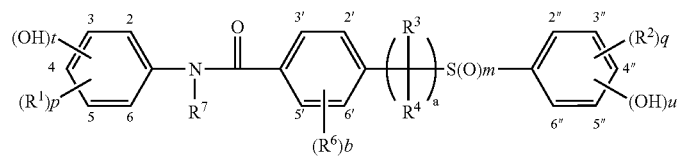

| Compound No. | (OH)t, (R¹)p | | | | | (R⁶)b | | | | | | | | a | m | (OH)u, (R²)q | | | | | Melting point (° C.) |
|---|---|---|---|---|---|---|---|---|---|---|---|---|---|---|---|---|---|---|---|---|---|
| | 2- | 3- | 4- | 5- | 6- | 2'- | 3'- | 5'- | 6'- | R⁷ | R³ | R⁴ | | | | 2"- | 3"- | 4"- | 5"- | 6"- | |
| XII-426 | H | H | H | H | H | H | H | H | H | H | H | H | 1 | 0 | H | H | OH | H | H | |
| XII-427 | H | H | H | H | H | H | H | H | H | H | H | H | 1 | 1 | H | H | OH | H | H | |
| XII-428 | H | H | H | H | H | H | H | H | H | H | H | H | 1 | 2 | H | H | OH | H | H | |
| XII-429 | H | H | H | H | H | H | H | H | H | H | H | H | 1 | 0 | OH | H | H | H | H | |
| XII-430 | H | H | OH | H | H | H | H | H | H | H | H | H | 1 | 0 | H | H | H | H | H | |
| XII-431 | H | H | OH | H | H | H | H | H | H | H | H | H | 1 | 1 | H | H | H | H | H | |
| XII-432 | H | H | OH | H | H | H | H | H | H | H | H | H | 1 | 2 | H | H | H | H | H | |
| XII-433 | H | OH | H | H | H | H | H | H | H | H | H | H | 1 | 0 | H | H | H | H | H | |
| XII-434 | H | OH | H | H | H | H | H | H | H | H | H | H | 1 | 1 | H | H | H | H | H | |
| XII-435 | H | OH | H | H | H | H | H | H | H | H | H | H | 1 | 2 | H | H | H | H | H | |
| XII-436 | OH | H | H | H | H | H | H | H | H | H | H | H | 1 | 0 | H | H | H | H | H | |
| XII-437 | OH | H | H | H | H | H | H | H | H | H | H | H | 1 | 1 | H | H | H | H | H | |
| XII-438 | OH | H | H | H | H | H | H | H | H | H | H | H | 1 | 2 | H | H | H | H | H | |
| XII-439 | H | H | OH | H | H | H | H | H | H | H | H | H | 1 | 0 | H | H | OH | H | H | |
| XII-440 | H | H | OH | H | H | H | H | H | H | H | H | H | 1 | 1 | H | H | OH | H | H | |
| XII-441 | H | H | OH | H | H | H | H | H | H | H | H | H | 1 | 2 | H | H | OH | H | H | |
| XII-442 | H | OH | H | H | H | H | H | H | H | H | H | H | 1 | 0 | H | H | OH | H | H | |
| XII-443 | H | OH | H | H | H | H | H | H | H | H | H | H | 1 | 1 | H | H | OH | H | H | |
| XII-444 | H | OH | H | H | H | H | H | H | H | H | H | H | 1 | 2 | H | H | OH | H | H | |
| XII-445 | OH | H | H | H | H | H | H | H | H | H | H | H | 1 | 0 | H | H | OH | H | H | |
| XII-446 | OH | H | H | H | H | H | H | H | H | H | H | H | 1 | 1 | H | H | OH | H | H | |
| XII-447 | OH | H | H | H | H | H | H | H | H | H | H | H | 1 | 2 | H | H | OH | H | H | |
| XII-448 | H | H | OH | H | H | H | H | H | H | H | H | H | 2 | 0 | H | H | OH | H | H | |
| XII-449 | H | H | OH | H | H | H | H | H | H | H | H | H | 2 | 1 | H | H | OH | H | H | |
| XII-450 | H | H | OH | H | H | H | H | H | H | H | H | H | 2 | 2 | H | H | OH | H | H | |
| XII-451 | H | OH | H | H | H | H | H | H | H | H | H | H | 2 | 0 | H | H | OH | H | H | |
| XII-452 | H | OH | H | H | H | H | H | H | H | H | H | H | 2 | 1 | H | H | OH | H | H | |
| XII-453 | H | OH | H | H | H | H | H | H | H | H | H | H | 2 | 2 | H | H | OH | H | H | |
| XII-454 | OH | H | H | H | H | H | H | H | H | H | H | H | 2 | 0 | H | H | OH | H | H | |
| XII-455 | OH | H | H | H | H | H | H | H | H | H | H | H | 2 | 1 | H | H | OH | H | H | |
| XII-456 | OH | H | H | H | H | H | H | H | H | H | H | H | 2 | 2 | H | H | OH | H | H | |
| XII-457 | H | H | H | H | H | H | H | H | H | H | H | H | 1 | 0 | OH | H | OH | H | H | |
| XII-458 | H | H | OH | H | H | H | H | H | H | H | H | H | 1 | 0 | OH | H | OH | H | H | |
| XII-459 | H | OH | H | H | H | H | H | H | H | H | H | H | 1 | 0 | OH | H | OH | H | H | |
| XII-460 | OH | H | H | H | H | H | H | H | H | H | H | H | 1 | 0 | OH | H | OH | H | H | |
| XII-461 | H | H | H | H | H | H | H | H | H | H | CH₃ | H | 1 | 0 | H | H | OH | H | H | |
| XII-462 | H | H | H | H | H | H | H | H | H | H | CH₃ | H | 1 | 2 | H | H | OH | H | H | |
| XII-463 | H | H | H | H | H | H | H | H | H | H | CH₃ | CH₃ | 1 | 0 | H | H | OH | H | H | |

TABLE 6-continued

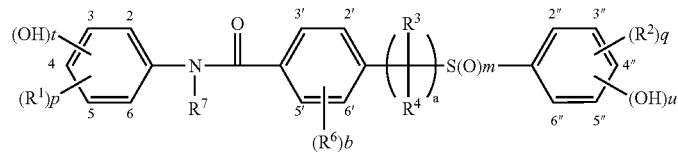

| Compound No. | (OH)t, (R¹)p 2- | 3- | 4- | 5- | 6- | (R⁶)b 2'- | 3'- | 5'- | 6'- | R⁷ | R³ | R⁴ | a | m | (OH)u, (R²)q 2"- | 3"- | 4"- | 5"- | 6"- | Melting point (° C.) |
|---|---|---|---|---|---|---|---|---|---|---|---|---|---|---|---|---|---|---|---|---|
| XII-464 | H | H | H | H | H | H | H | H | H | H | CH₃ | CH₃ | 1 | 2 | H | H | OH | H | H | |
| XII-465 | H | H | H | H | H | CH₃ | H | H | H | H | H | H | 1 | 0 | H | H | OH | H | H | |
| XII-466 | H | H | H | H | H | CH₃ | H | H | H | H | H | H | 1 | 2 | H | H | OH | H | H | |
| XII-467 | H | H | H | H | H | H | CH₃ | H | H | H | H | H | 1 | 0 | H | H | OH | H | H | |
| XII-468 | H | H | H | H | H | H | CH₃ | H | H | H | H | H | 1 | 2 | H | H | OH | H | H | |
| XII-469 | H | H | H | H | H | H | H | CH₃ | H | H | H | H | 1 | 0 | H | H | OH | H | H | |
| XII-470 | H | H | H | H | H | H | H | CH₃ | H | H | H | H | 1 | 2 | H | H | OH | H | H | |
| XII-471 | H | H | H | H | H | H | H | H | CH₃ | H | H | H | 1 | 0 | H | H | OH | H | H | |
| XII-472 | H | H | H | H | H | H | H | H | CH₃ | H | H | H | 1 | 2 | H | H | OH | H | H | |
| XII-473 | H | H | H | H | H | Cl | H | H | H | H | H | H | 1 | 0 | H | H | OH | H | H | |
| XII-474 | H | H | H | H | H | Cl | H | H | H | H | H | H | 1 | 2 | H | H | OH | H | H | |
| XII-475 | H | H | H | H | H | H | Cl | H | H | H | H | H | 1 | 0 | H | H | OH | H | H | |
| XII-476 | H | H | H | H | H | H | Cl | H | H | H | H | H | 1 | 2 | H | H | OH | H | H | |
| XII-477 | H | H | H | H | H | Cl | H | Cl | H | H | H | H | 1 | 0 | H | H | OH | H | H | |
| XII-478 | H | H | H | H | H | Cl | H | Cl | H | H | H | H | 1 | 2 | H | H | OH | H | H | |
| XII-479 | H | H | H | H | H | H | H | H | Cl | H | H | H | 1 | 0 | H | H | OH | H | H | |
| XII-480 | H | H | H | H | H | H | H | H | Cl | H | H | H | 1 | 2 | H | H | OH | H | H | |
| XII-481 | H | H | CH₃ | H | H | H | H | H | H | H | H | H | 1 | 0 | H | H | OH | H | H | |
| XII-482 | H | H | CH₃ | H | H | H | H | H | H | H | H | H | 1 | 2 | H | H | OH | H | H | |
| XII-483 | H | CH₃ | H | H | H | H | H | H | H | H | H | H | 1 | 0 | H | H | OH | H | H | |
| XII-484 | H | CH₃ | H | H | H | H | H | H | H | H | H | H | 1 | 2 | H | H | OH | H | H | |
| XII-485 | CH₃ | H | H | H | H | H | H | H | H | H | H | H | 1 | 0 | H | H | OH | H | H | |
| XII-486 | CH₃ | H | H | H | H | H | H | H | H | H | H | H | 1 | 2 | H | H | OH | H | H | |
| XII-487 | H | H | CH₃O | H | H | H | H | H | H | H | H | H | 1 | 0 | H | H | OH | H | H | |
| XII-488 | H | H | CH₃O | H | H | H | H | H | H | H | H | H | 1 | 2 | H | H | OH | H | H | |
| XII-489 | H | CH₃O | H | H | H | H | H | H | H | H | H | H | 1 | 0 | H | H | OH | H | H | |
| XII-490 | H | CH₃O | H | H | H | H | H | H | H | H | H | H | 1 | 2 | H | H | OH | H | H | |
| XII-491 | CH₃O | H | H | H | H | H | H | H | H | H | H | H | 1 | 0 | H | H | OH | H | H | |
| XII-492 | CH₃O | H | H | H | H | H | H | H | H | H | H | H | 1 | 2 | H | H | OH | H | H | |
| XII-493 | H | H | NO₂ | H | H | H | H | H | H | H | H | H | 1 | 0 | H | H | OH | H | H | |
| XII-494 | H | H | NO₂ | H | H | H | H | H | H | H | H | H | 1 | 2 | H | H | OH | H | H | |
| XII-495 | H | NO₂ | H | H | H | H | H | H | H | H | H | H | 1 | 0 | H | H | OH | H | H | |
| XII-496 | H | NO₂ | H | H | H | H | H | H | H | H | H | H | 1 | 2 | H | H | OH | H | H | |
| XII-497 | NO₂ | H | H | H | H | H | H | H | H | H | H | H | 1 | 0 | H | H | OH | H | H | |
| XII-498 | NO₂ | H | H | H | H | H | H | H | H | H | H | H | 1 | 2 | H | H | OH | H | H | |
| XII-499 | H | H | Cl | H | H | H | H | H | H | H | H | H | 1 | 0 | H | H | OH | H | H | |
| XII-500 | H | H | Cl | H | H | H | H | H | H | H | H | H | 1 | 2 | H | H | OH | H | H | |
| XII-501 | H | Cl | H | H | H | H | H | H | H | H | H | H | 1 | 0 | H | H | OH | H | H | |
| XII-502 | H | Cl | H | H | H | H | H | H | H | H | H | H | 1 | 2 | H | H | OH | H | H | |
| XII-503 | Cl | H | H | H | H | H | H | H | H | H | H | H | 1 | 0 | H | H | OH | H | H | |
| XII-504 | Cl | H | H | H | H | H | H | H | H | H | H | H | 1 | 2 | H | H | OH | H | H | |
| XII-505 | H | H | H | H | H | H | H | H | H | CH₃ | H | H | 1 | 0 | H | H | OH | H | H | |
| XII-506 | H | H | H | H | H | H | H | H | H | CH₃ | H | H | 1 | 2 | H | H | OH | H | H | |
| XII-507 | H | H | H | H | H | H | H | H | H | Ph | H | H | 1 | 0 | H | H | OH | H | H | |
| XII-508 | H | H | H | H | H | H | H | H | H | Ph | H | H | 1 | 2 | H | H | OH | H | H | |
| XII-509 | H | H | H | H | H | H | H | H | H | CH₂Ph | H | H | 1 | 0 | H | H | OH | H | H | |
| XII-510 | H | H | H | H | H | H | H | H | H | CH₂Ph | H | H | 1 | 2 | H | H | OH | H | H | |
| XII-511 | H | CO₂CH₃ | H | H | H | H | H | H | H | H | H | H | 1 | 0 | H | H | OH | H | H | |
| XII-512 | H | CO₂CH₃ | H | H | H | H | H | H | H | H | H | H | 1 | 2 | H | H | OH | H | H | |
| XII-513 | H | CO₂H | H | H | H | H | H | H | H | H | H | H | 1 | 0 | H | H | OH | H | H | |
| XII-514 | H | CO₂H | H | H | H | H | H | H | H | H | H | H | 1 | 2 | H | H | OH | H | H | |
| XII-515 | H | SO₂NH₂ | H | H | H | H | H | H | H | H | H | H | 1 | 0 | H | H | OH | H | H | |
| XII-516 | H | SO₂NH₂ | H | H | H | H | H | H | H | H | H | H | 1 | 2 | H | H | OH | H | H | |

TABLE 7

[Structure: HO-C6H4-S-C(R8)(R9)-(C(R10)(R11))c-Y6-C(=O)-S-C6H4-OH]

| Compound No. | Y6 | R10 | R11 | n | R8 | R9 |
|---|---|---|---|---|---|---|
| XIII-1 | none | H | H | 1 | H | H |
| XIII-2 | none | CH3 | H | 1 | H | H |
| XIII-3 | none | H | H | 1 | CH3 | H |
| XIII-4 | none | H | H | 1 | Ph | H |
| XIII-5 | none | — | — | 0 | H | H |
| XIII-6 | none | — | — | 0 | CH3 | H |
| XIII-7 | none | — | — | 0 | CH3 | CH3 |
| XIII-8 | none | — | — | 0 | C2H5 | H |
| xIII-9 | none | — | — | 0 | n-C3H7 | H |
| XIII-10 | none | — | — | 0 | i-C3H7 | H |
| XIII-11 | 1,4-phenylene | H | H | 1 | H | H |
| XIII-12 | 1,4-phenylene | CH3 | H | 1 | H | H |
| XIII-13 | 1,4-phenylene | H | H | 1 | CH3 | H |
| XIII-14 | 1,4-phenylene | H | H | 1 | Ph | H |
| XIII-15 | 1,4-phenylene | — | — | 0 | H | H |
| XIII-16 | 1,4-phenylene | — | — | 0 | CH3 | H |
| XIII-17 | 1,4-phenylene | — | — | 0 | CH3 | CH3 |
| XIII-18 | 1,4-phenylene | — | — | 0 | C2H5 | H |
| XIII-19 | 1,4-phenylene | — | — | 0 | n-C3H7 | H |
| XIII-20 | 1,4-phenylene | — | — | 0 | i-C3H7 | H |
| XIII-21 | 1,4-phenylene | 13 | — | 0 | Ph | |
| XIII-22 | | | | | | |
| XIII-23 | 1,3-phenylene | H | H | 1 | H | H |
| XIII-24 | 1,3-phenylene | CH3 | H | 1 | H | H |
| XIII-25 | 1,3-phenylene | H | H | 1 | CH3 | H |
| XIII-26 | 1,3-phenylene | H | H | 1 | Ph | H |
| XIII-27 | 1,3-phenylene | — | — | 0 | H | H |
| XIII-28 | 1,3-phenylene | — | — | 0 | CH3 | H |
| XIII-29 | 1,3-phenylene | — | — | 0 | CH3 | CH3 |
| XIII-30 | 1,3-phenylene | — | — | 0 | C2H5 | H |
| XIII-31 | 1,3-phenylene | — | — | 0 | n-C3H7 | H |
| XIII-32 | 1,3-phenylene | — | — | 0 | i-C3H7 | H |
| XIII-33 | 1,3-phenylene | — | — | 0 | Ph | H |
| XIII-34 | 1,2-phenylene | H | H | 1 | H | H |
| XIII-35 | 1,2-phenylene | CH3 | H | 1 | H | H |
| XIII-36 | 1,2-phenylene | H | H | 1 | CH3 | H |
| XIII-37 | 1,2-phenylene | H | H | 1 | Ph | H |
| XIII-38 | 1,2-phenylene | — | — | 0 | H | H |
| XIII-39 | 1,2-phenylene | — | — | 0 | CH3 | H |
| XIII-40 | 1,2-phenylene | — | — | 0 | CH3 | CH3 |
| XIII-41 | 1,2-phenylene | — | — | 0 | C2H5 | H |
| XIII-42 | 1,2-phenylene | — | — | 0 | n-C3H7 | H |
| XIII-43 | 1,2-phenylene | — | — | 0 | i-C3H7 | H |
| XIII-44 | 1,2-phenylene | — | — | 0 | Ph | H |
| XIII-45 | 2-methoxy-1,4-phenylene | — | — | 0 | H | H |
| XIII-46 | 2-methyl-1,4-phenylene | — | — | 0 | H | H |
| XIII-47 | 2-chloro-1,4-phenylene | — | — | 0 | H | H |

TABLE 7-continued

[Structure: HO-C6H4-S-C(R8)(R9)-(C(R10)(R11))c-Y6-C(=O)-S-C6H4-OH]

| Compound No. | Y6 | R10 | R11 | n | R8 | R9 |
|---|---|---|---|---|---|---|
| XIII-48 | 2,4-dimethyl-(OCH3)-phenyl | — | — | 0 | H | H |
| XIII-49 | 2,3-dimethyl-4-chloro-phenyl | — | — | 0 | H | H |

TABLE 8

[Structure: (OH)t, (R1)p-phenyl-Y7-C(=O)-S-C6H4-OH]

| Compound No. | Y7 | (OH)t, (R1)p 2 | 3 | 4 | 5 | 6 | Melting point (°C.) |
|---|---|---|---|---|---|---|---|
| XIV-1 | NH | H | H | H | H | H | 167–171 |
| XIV-2 | NH | H | H | CH3 | H | H | |
| XIV-3 | NH | H | H | OCH3 | H | H | |
| XIV-4 | NH | H | H | Cl | H | H | |
| XIV-5 | NH | H | H | CO2H | H | H | |
| XIV-6 | NH | H | H | CO2CH3 | H | H | |
| XIV-7 | NH | H | CH3 | H | H | H | |
| XIV-8 | NH | H | OCH3 | H | H | H | |
| XIV-9 | NH | H | Cl | H | H | H | |
| XIV-10 | NH | H | CO2H | H | H | H | |
| XIV-11 | NH | H | CO2CH3 | H | H | H | |
| XIV-12 | NH | CH3 | H | H | H | H | |
| XIV-13 | NH | OCH3 | H | H | H | H | |
| XIV-14 | NH | Cl | H | H | H | H | |
| XIV-15 | NH | CO2H | H | H | H | H | |
| XIV-16 | NH | CO2CH3 | H | H | H | H | |
| XIV-17 | NH | NO2 | H | H | H | H | |
| XIV-18 | NH | H | NO2 | H | H | H | |
| XIV-19 | NH | H | H | NO2 | H | H | |
| XIV-20 | NH | CH3 | H | H | —NH—C(=O)—NH2 | H | |
| XIV-21 | NH | CH3 | H | H | —NH—C(=O)—NHCH3 | H | |
| XIV-22 | NH | CH3 | H | H | —NH—C(=O)—N(CH3)2 | H | |
| XIV-23 | NH | CH3 | H | H | —N(CH3)—C(=O)—N(CH3)2 | H | |

TABLE 8-continued $$\text{(OH)}_t\text{-Ar-}Y^7\text{-C(=O)-S-C}_6\text{H}_4\text{-OH}$$
$(R^1)_p$

| Compound No. | $Y^7$ | \(OH)t, (R¹)p 2 | 3 | 4 | 5 | 6 | Melting point (°C.) |
|---|---|---|---|---|---|---|---|
| XIV-24 | NH | CH₃ | H | H | —NH—C(=O)—NH—C₆H₅ | H | |
| XIV-25 | NH | H | H | CH₃ | " | H | |
| XIV-26 | NH | CH₃ | H | H | —NH—C(=O)—NH—C₆H₄—CH₃ | H | |
| XIV-27 | NH | H | H | CH₃ | " | H | |
| XIV-28 | NH | CH₃ | H | H | —NH—C(=O)—NH—C₆H₄—OCH₃ | H | |
| XIV-29 | NH | H | H | CH₃ | " | H | |
| XIV-30 | NH | CH₃ | H | H | —NH—C(=O)—NH—C₆H₄—OH | H | |
| XIV-31 | NH | H | H | CH₃ | " | H | |
| XIV-32 | NH | CH₃ | H | H | —NH—C(=O)—NH—C₆H₄—OH (m) | H | |
| XIV-33 | NH | H | H | CH₃ | " | H | |
| XIV-34 | NH | CH₃ | H | H | —NH—C(=O)—NH—C₆H₄—OH (o) | H | |
| XIV-35 | — | H | H | OH | H | H | 231–234 |
| XIV-36 | — | H | OH | H | H | H | |
| XIV-37 | — | OH | H | H | H | H | |
| XIV-38 | — | CO₂H | H | H | H | H | |
| XIV-39 | — | CO₂CH₃ | H | H | H | H | |

TABLE 9
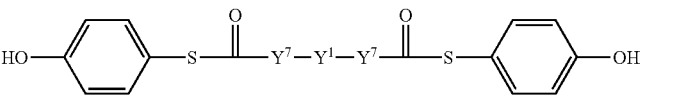
| Compound No. | Y⁷ | Y¹ | Melting point (° C.) |
|---|---|---|---|
| XIV-40 | NH | 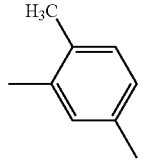 | 177–180 |
| XIV-41 | NH | 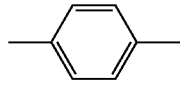 | |
| XIV-42 | NH | 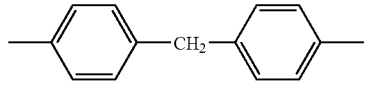 | 108–112 |
| XIV-43 | NH | 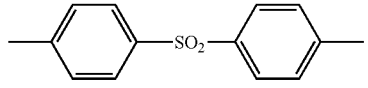 | |
| XIV-44 | NH | 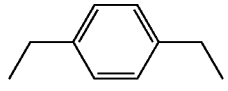 | |
| XIV-45 | NH | 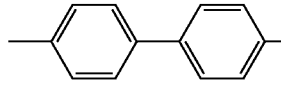 | |
| XIV-46 | NH | 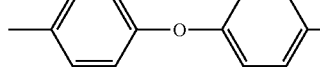 | |
| XIV-47 | NH | 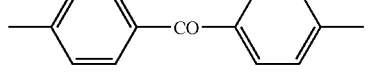 | |
| XIV-48 | NH | 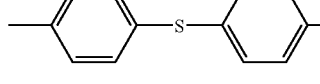 | |
| XIV-49 | — | —CH$_2$— | |
| XIV-50 | — | —CH$_2$—CH$_2$— | 226–229 |
| XIV-51 | — | —CH$_2$—CH$_2$—CH$_2$—CH$_2$— | |
| XIV-52 | — | 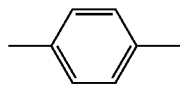 | 250+ |
| XIV-53 | — | 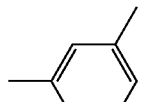 | 218–221 |

TABLE 9-continued

HO—⌬—S—C(=O)—Y⁷—Y¹—Y⁷—C(=O)—S—⌬—OH

| Compound No. | Y⁷ | Y¹ | Melting point (° C.) |
|---|---|---|---|
| XIV-54 | — | (1,2-phenylene) | 198–200 |
| XIV-55 | — | —⌬—O—CH₂—CH₂—O—⌬— | |

TABLE 10

HO—⌬—S(O)$_m$—(CR³R⁴)$_a$—C(=O)—O—Y¹—N(R⁵)—C(=O)—(CR³R⁴)$_a$—S(O)$_m$—⌬—OH

| Compound No. | R³ | R⁴ | R⁵ | m | a | Y¹ |
|---|---|---|---|---|---|---|
| XV-1 | H | H | H | 0 | 1 | —CH₂—CH₂— |
| XV-2 | H | H | H | 1 | 1 | |
| XV-3 | H | H | H | 2 | 1 | |
| XV-4 | H | H | H | 0 | 2 | |
| XV-5 | H | H | H | 1 | 2 | |
| XV-6 | H | H | H | 2 | 2 | |
| XV-7 | CH₃ | H | H | 0 | 1 | |
| XV-8 | CH₃ | H | H | 1 | 1 | |
| XV-9 | CH₃ | H | H | 2 | 1 | |
| XV-10 | CH₃ | CH₃ | H | 0 | 1 | |
| XV-11 | CH₃ | CH₃ | H | 1 | 1 | |
| XV-12 | CH₃ | CH₃ | H | 2 | 1 | |
| XV-13 | H | H | CH₃ | 0 | 1 | —CH₂—CH₂— |
| XV-14 | H | H | CH₃ | 1 | 1 | |
| XV-15 | H | H | CH₃ | 2 | 1 | |
| XV-16 | H | H | Ph | 0 | 1 | |
| XV-17 | H | H | CH₂Ph | 0 | 1 | |
| XV-18 | H | H | 4-CH₃—Ph | 0 | 1 | |
| XV-19 | H | H | —CH₂—CH₂—O—C(=O)—CH₂—S—⌬—OH | 0 | 1 | |
| XV-20 | H | H | H | 0 | 1 | —CH₂—CH₂—CH₂— |
| XV-21 | H | H | H | 1 | 1 | |
| XV-22 | H | H | H | 2 | 1 | |
| XV-23 | H | H | H | 0 | 1 | —CH₂—CH₂—CH₂—CH₂— |
| XV-24 | H | H | H | 1 | 1 | |
| XV-25 | H | H | H | 2 | 1 | |
| XV-26 | H | H | H | 0 | 1 | —⌬— (1,4-phenylene) |
| XV-27 | H | H | H | 1 | 1 | |
| XV-28 | H | H | H | 2 | 1 | |
| XV-29 | H | H | H | 0 | 2 | |
| XV-30 | H | H | H | 1 | 2 | |
| XV-31 | H | H | H | 2 | 2 | |
| XV-32 | CH₃ | H | H | 0 | 1 | |
| XV-33 | CH₃ | H | H | 1 | 1 | |
| XV-34 | CH₃ | H | H | 2 | 1 | |
| XV-35 | CH₃ | CH₃ | H | 0 | 1 | |
| XV-36 | CH₃ | CH₃ | H | 1 | 1 | |
| XV-37 | CH₃ | CH₃ | H | 2 | 1 | |
| XV-38 | H | H | CH₃ | 0 | 1 | |
| XV-39 | H | H | CH₃ | 1 | 1 | |
| XV-40 | H | H | CH₃ | 2 | 1 | |

TABLE 10-continued

HO—⟨phenyl⟩—S(O)m—(CR³R⁴)ₐ—C(O)—O—Y¹—N(R⁵)—C(O)—(CR³R⁴)ₐ—S(O)m—⟨phenyl⟩—OH

| Compound No. | R³ | R⁴ | R⁵ | m | a | Y¹ |
|---|---|---|---|---|---|---|
| XV-41 | H | H | H | 0 | 1 | 1,3-dimethylbenzene |
| XV-42 | H | H | H | 1 | 1 | |
| XV-43 | H | H | H | 2 | 1 | |
| XV-44 | H | H | H | 0 | 2 | |
| XV-45 | H | H | H | 1 | 2 | |
| XV-46 | H | H | H | 2 | 2 | |
| XV-47 | CH₃ | H | H | 0 | 1 | |
| XV-48 | CH₃ | H | H | 1 | 1 | |
| XV-49 | CH₃ | H | H | 2 | 1 | |
| XV-50 | CH₃ | CH₃ | H | 0 | 1 | |
| XV-51 | CH₃ | CH₃ | H | 1 | 1 | |
| XV-52 | CH₃ | CH₃ | H | 2 | 1 | |
| XV-53 | H | H | CH₃ | 0 | 1 | |
| XV-54 | H | H | CH₃ | 1 | 1 | |
| XV-55 | H | H | CH₃ | 2 | 1 | |
| XV-56 | H | H | H | 0 | 1 | 1,2-dimethylbenzene |
| XV-57 | H | H | H | 1 | 1 | |
| XV-58 | H | H | H | 2 | 1 | |
| XV-59 | H | H | H | 0 | 2 | |
| XV-60 | H | H | H | 1 | 2 | |
| XV-61 | H | H | H | 2 | 2 | |
| XV-62 | CH₃ | H | H | 0 | 1 | |
| XV-63 | CH₃ | H | H | 1 | 1 | |
| XV-64 | CH₃ | H | H | 2 | 1 | |
| XV-65 | CH₃ | CH₃ | H | 0 | 1 | |
| XV-66 | CH₃ | CH₃ | H | 1 | 1 | |
| XV-67 | CH₃ | CH₃ | H | 2 | 1 | |
| XV-68 | H | H | CH₃ | 0 | 1 | |
| XV-69 | H | H | CH₃ | 1 | 1 | |
| XV-70 | H | H | CH₃ | 2 | 1 | |
| XV-71 | H | H | H | 0 | 1 | 2,5-dimethyl-nitrobenzene (O₂N substituent) |
| XV-72 | H | H | H | 0 | 1 | 2,5-dimethyl-nitrobenzene (NO₂ substituent) |
| XV-73 | H | H | H | 0 | 1 | 2,5-dimethyl-chlorobenzene (Cl substituent) |
| XV-74 | H | H | H | 0 | 1 | 2,5-dimethyl-chlorobenzene (Cl substituent) |

TABLE 10-continued $$\text{HO}-\bigcirc-\text{S(O)}_m-\left(\begin{array}{c}R^3\\|\\-\\|\\R^4\end{array}\right)_a-\overset{O}{\overset{\|}{C}}-O-Y^1-\underset{R^5}{N}-\overset{O}{\overset{\|}{C}}-\left(\begin{array}{c}R^3\\|\\-\\|\\R^4\end{array}\right)_a-\text{S(O)}_m-\bigcirc-\text{OH}$$

| Compound No. | $R^3$ | $R^4$ | $R^5$ | m | a | $Y^1$ |
|---|---|---|---|---|---|---|
| XV-75 | H | H | H | 0 | 1 | 2,4-dimethyl-5-methylphenyl (H$_3$C at 3-position) |
| XV-76 | H | H | H | 0 | 1 | 2,5-dimethyl-3-(methoxycarbonyl)phenyl |
| XV-77 | H | H | H | 0 | 1 | 2,6-dimethylphenyl |
| XV-78 | H | H | H | 0 | 1 | 2,4-dimethyl-5-methoxyphenyl |
| XV-79 | H | H | H | 0 | 1 | 2,3,6-trimethylphenyl |
| XV-80 | H | H | H | 0 | 1 | 2,3,5-trimethylphenyl |
| XV-81 | H | H | H | 0 | 1 | 2,3-dimethyl-5-chlorophenyl |
| XV-82 | H | H | H | 0 | 1 | 2,3-dimethyl-5-nitrophenyl |

TABLE 10-continued
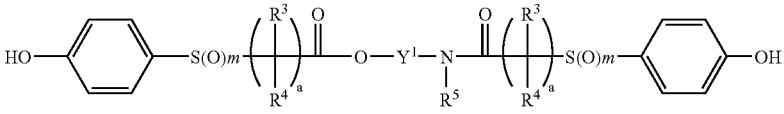
| Compound No. | R³ | R⁴ | R⁵ | m | a | Y¹ |
|---|---|---|---|---|---|---|
| XV-83 | H | H | H | 0 | 1 | 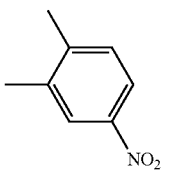 |
| XV-84 | H | H | H | 0 | 1 | 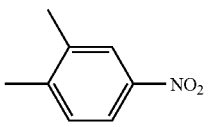 |
| XV-85 | H | H | H | 0 | 1 | 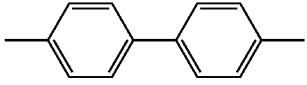 |
| XV-86 | H | H | H | 0 | 1 |  |
| XV-87 | H | H | H | 0 | 1 | 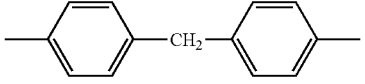 |
| XV-88 | H | H | H | 0 | 1 | 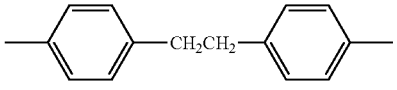 |
| XV-89 | H | H | H | 0 | 1 | 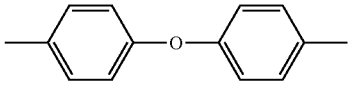 |
| XV-90 | H | H | H | 0 | 1 | 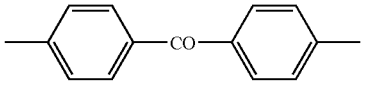 |
| XV-91 | H | H | H | 0 | 1 | 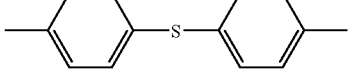 |
| XV-92 | H | H | H | 0 | 1 | 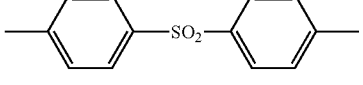 |

TABLE 11

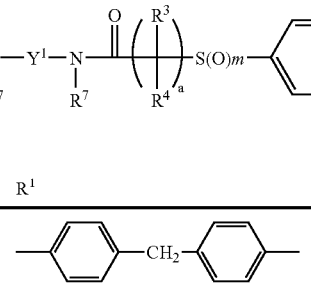

| Compound No. | (OH)t, (R¹)p 2- | 3- | 4- | 5- | 6- | Y² | Y³ | R¹ | R⁷ | R³ | R⁴ | a | m |
|---|---|---|---|---|---|---|---|---|---|---|---|---|---|
| XVI-1  | H      | H   | H      | H | H   | SO₂  | O | 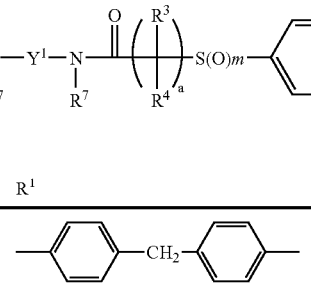  | H       | H   | H   | 1 | 0 |
| XVI-2  | CH₃    | H   | H      | H | H   | SO₂  | O |                       | H       | H   | H   | 1 | 0 |
| XVI-3  | H      | H   | CH₃    | H | H   | SO₂  | O |                       | H       | H   | H   | 1 | 0 |
| XVI-4  | H      | H   | CH₃    | H | H   | SO₂  | O |                       | H       | H   | H   | 1 | 1 |
| XVI-5  | H      | H   | CH₃    | H | H   | SO₂  | O |                       | H       | H   | H   | 1 | 2 |
| XVI-6  | H      | H   | CH₃    | H | H   | SO₂  | O |                       | H       | CH₃ | H   | 1 | 0 |
| XVI-7  | H      | H   | CH₃    | H | H   | SO₂  | O |                       | H       | CH₃ | CH₃ | 1 | 0 |
| XVI-8  | H      | H   | CH₃    | H | H   | SO₂  | O |                       | CH₃     | H   | H   | 1 | 0 |
| XVI-9  | H      | H   | CH₃    | H | H   | SO₂  | O |                       | H       | H   | H   | 2 | 0 |
| XVI-10 | H      | H   | OCH₃   | H | H   | SO₂  | O |                       | H       | H   | H   | 1 | 0 |
| XVI-11 | H      | H   | Cl     | H | H   | SO₂  | O |                       | H       | H   | H   | 1 | 0 |
| XVI-12 | H      | H   | Cl     | H | H   | CO   | O |                       | H       | H   | H   | 1 | 0 |
| XVI-13 | H      | H   | H      | H | H   | none | O |                       | H       | H   | H   | 1 | 0 |
| XVI-14 | H      | H   | H      | H | H   | none | S |                       | H       | H   | H   | 1 | 0 |
| XVI-15 | H      | H   | CH₃    | H | H   | none | O |                       | H       | H   | H   | 1 | 0 |
| XVI-16 | H      | H   | CH₃    | H | H   | none | S |                       | H       | H   | H   | 1 | 0 |
| XVI-17 | H      | H   | OCH₃   | H | H   | none | O |                       | H       | H   | H   | 1 | 0 |
| XVI-18 | H      | H   | OCH₃   | H | H   | none | S |                       | H       | H   | H   | 1 | 0 |
| XVI-19 | H      | H   | Cl     | H | H   | none | O |                       | H       | H   | H   | 1 | 0 |
| XVI-20 | H      | H   | Cl     | H | H   | none | S |                       | H       | H   | H   | 1 | 0 |
| XVI-21 | H      | NO₂ | H      | H | H   | SO₂  | O | 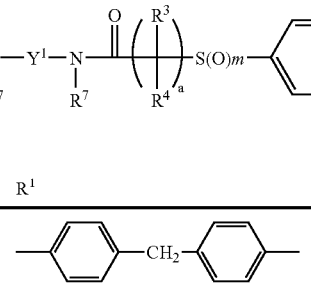  | H       | H   | H   | 1 | 0 |
| XVI-22 | H      | H   | CO₂CH₃ | H | H   | SO₂  | O |                       | H       | H   | H   | 1 | 0 |
| XVI-23 | H      | CH₃ | CH₃    | H | H   | SO₂  | O |                       | H       | H   | H   | 1 | 0 |
| XVI-24 | H      | H   | H      | H | H   | SO₂  | O |                       | Ph      | H   | H   | 1 | 0 |
| XVI-25 | H      | H   | H      | H | H   | SO₂  | O |                       | CH₂Ph   | H   | H   | 1 | 0 |
| XVI-26 | H      | H   | H      | H | H   | SO₂  | O |                       | 4-CH₃—Ph| H   | H   | 1 | 0 |
| XVI-27 | H      | H   | H      | H | H   | SO₂  | O |                       | 4-Cl—Ph | H   | H   | 1 | 0 |
| XVI-28 | NO₂    | H   | H      | H | H   | none | O |                       | H       | H   | H   | 1 | 0 |
| XVI-29 | H      | NO₂ | H      | H | H   | none | O |                       | H       | H   | H   | 1 | 0 |
| XVI-30 | H      | H   | NO₂    | H | H   | none | O |                       | H       | H   | H   | 1 | 0 |
| XVI-31 | CH₂CH₃ | H   | H      | H | H   | none | O |                       | H       | H   | H   | 1 | 0 |
| XVI-32 | Cl     | H   | H      | H | CH₃ | none | O |                       | H       | H   | H   | 1 | 0 |
| XVI-33 | H      | H   | H      | H | H   | none | O |                       | CH₃     | H   | H   | 1 | 0 |
| XVI-34 | H      | H   | H      | H | H   | none | O |                       | Ph      | H   | H   | 1 | 0 |
| XVI-35 | H      | H   | H      | H | H   | none | O |                       | CH₂Ph   | H   | H   | 1 | 0 |
| XVI-36 | H      | H   | H      | H | H   | none | O |                       | 4-CH₃—Ph| H   | H   | 1 | 0 |
| XVI-37 | H      | H   | H      | H | H   | none | O |                       | 4-Cl—Ph | H   | H   | 1 | 0 |
| XVI-38 | H      | H   | H      | H | H   | SO₂  | O | 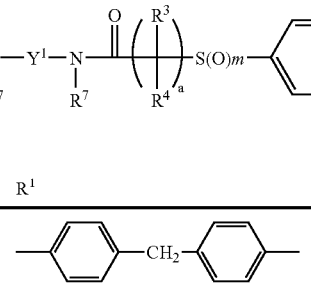  | H       | H   | H   | 1 | 0 |
| XVI-39 | CH₃    | H   | H      | H | H   | SO₂  | O |                       | H       | H   | H   | 1 | 0 |
| XVI-40 | H      | H   | CH₃    | H | H   | SO₂  | O |                       | H       | H   | H   | 1 | 0 |
| XVI-41 | H      | H   | CH₃    | H | H   | SO₂  | O |                       | H       | H   | H   | 1 | 1 |
| XVI-42 | H      | H   | CH₃    | H | H   | SO₂  | O |                       | H       | H   | H   | 1 | 2 |
| XVI-43 | H      | H   | CH₃    | H | H   | SO₂  | O |                       | H       | CH₃ | H   | 1 | 0 |
| XVI-44 | H      | H   | CH₃    | H | H   | SO₂  | O |                       | H       | CH₃ | CH₃ | 1 | 0 |
| XVI-45 | H      | H   | CH₃    | H | H   | SO₂  | O |                       | CH₃     | H   | H   | 1 | 0 |
| XVI-46 | H      | H   | CH₃    | H | H   | SO₂  | O |                       | H       | H   | H   | 2 | 0 |
| XVI-47 | H      | H   | OCH₃   | H | H   | SO₂  | O |                       | H       | H   | H   | 1 | 0 |
| XVI-48 | H      | H   | Cl     | H | H   | SO₂  | O |                       | H       | H   | H   | 1 | 0 |
| XVI-49 | H      | H   | Cl     | H | H   | CO   | O |                       | H       | H   | H   | 1 | 0 |
| XVI-50 | H      | H   | H      | H | H   | none | O |                       | H       | H   | H   | 1 | 0 |
| XVI-51 | H      | H   | H      | H | H   | none | S |                       | H       | H   | H   | 1 | 0 |
| XVI-52 | H      | H   | CH₃    | H | H   | none | O |                       | H       | H   | H   | 1 | 0 |
| XVI-53 | H      | H   | CH₃    | H | H   | none | S |                       | H       | H   | H   | 1 | 0 |
| XVI-54 | H      | H   | OCH₃   | H | H   | none | O |                       | H       | H   | H   | 1 | 0 |
| XVI-55 | H      | H   | OCH₃   | H | H   | none | S |                       | H       | H   | H   | 1 | 0 |
| XVI-56 | H      | H   | Cl     | H | H   | none | O |                       | H       | H   | H   | 1 | 0 |
| XVI-57 | H      | H   | Cl     | H | H   | none | S |                       | H       | H   | H   | 1 | 0 |
| XVI-58 | H      | H   | H      | H | H   | SO₂  | O | 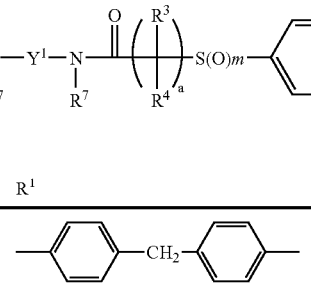  | H       | H   | H   | 1 | 0 |
| XVI-59 | CH₃    | H   | H      | H | H   | SO₂  | O |                       | H       | H   | H   | 1 | 0 |
| XVI-60 | H      | H   | CH₃    | H | H   | SO₂  | O |                       | H       | H   | H   | 1 | 0 |
| XVI-61 | H      | H   | CH₃    | H | H   | SO₂  | O |                       | H       | H   | H   | 1 | 1 |
| XVI-62 | H      | H   | CH₃    | H | H   | SO₂  | O |                       | H       | H   | H   | 1 | 2 |
| XVI-63 | H      | H   | CH₃    | H | H   | SO₂  | O |                       | H       | CH₃ | H   | 1 | 0 |
| XVI-64 | H      | H   | CH₃    | H | H   | SO₂  | O |                       | H       | CH₃ | CH₃ | 1 | 0 |
| XVI-65 | H      | H   | CH₃    | H | H   | SO₂  | O |                       | CH₃     | H   | H   | 1 | 0 |
| XVI-66 | H      | H   | CH₃    | H | H   | SO₂  | O |                       | H       | H   | H   | 2 | 0 |

TABLE 11-continued

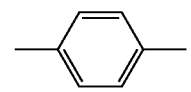

| Compound No. | (OH)t, (R¹)p 2- | 3- | 4- | 5- | 6- | Y² | Y³ | R¹ | R⁷ | R³ | R⁴ | a | m |
|---|---|---|---|---|---|---|---|---|---|---|---|---|---|
| XVI-67 | H | H | OCH₃ | H | H | SO₂ | O |  | H | H | H | 1 | 0 |
| XVI-68 | H | H | Cl | H | H | SO₂ | O |  | H | H | H | 1 | 0 |
| XVI-69 | H | H | Cl | H | H | CO | O |  | H | H | H | 1 | 0 |
| XVI-70 | H | H | H | H | H | none | O |  | H | H | H | 1 | 0 |
| XVI-71 | H | H | H | H | H | none | S |  | H | H | H | 1 | 0 |
| XVI-72 | H | H | CH₃ | H | H | none | O |  | H | H | H | 1 | 0 |
| XVI-73 | H | H | CH₃ | H | H | none | S |  | H | H | H | 1 | 0 |
| XVI-74 | H | H | OCH₃ | H | H | none | O |  | H | H | H | 1 | 0 |
| XVI-75 | H | H | OCH₃ | H | H | none | S |  | H | H | H | 1 | 0 |
| XVI-76 | H | H | Cl | H | H | none | O |  | H | H | H | 1 | 0 |
| XVI-77 | H | H | Cl | H | H | none | S |  | H | H | H | 1 | 0 |
| XVI-78 | H | H | CH₃ | H | H | SO₂ | O | —CH₂—CH₂— | H | H | H | 1 | 0 |
| XVI-79 | H | H | H | H | H | none | O |  | H | H | H | 1 | 0 |
| XVI-80 | H | H | H | H | H | none | S |  | H | H | H | 1 | 0 |
| XVI-81 | H | H | CH₃ | H | H | SO₂ | O | —CH₂—CH₂—CH₂—CH₂— | H | H | H | 1 | 0 |
| XVI-82 | H | H | H | H | H | none | O |  | H | H | H | 1 | 0 |
| XVI-83 | H | H | H | H | H | none | S |  | H | H | H | 1 | 0 |
| XVI-84 | H | H | CH₃ | H | H | SO₂ | O | 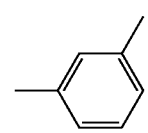 | H | H | H | 1 | 0 |
| XVI-85 | H | H | H | H | H | none | O |  | H | H | H | 1 | 0 |
| XVI-86 | H | H | H | H | H | none | S |  | H | H | H | 1 | 0 |
| XVI-87 | H | H | CH₃ | H | H | SO₂ | O | 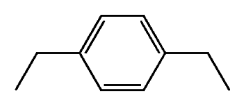 | H | H | H | 1 | 0 |
| XVI-88 | H | H | H | H | H | none | O |  | H | H | H | 1 | 0 |
| XVI-89 | H | H | H | H | H | none | S |  | H | H | H | 1 | 0 |
| XVI-90 | H | H | CH₃ | H | H | SO₂ | O | 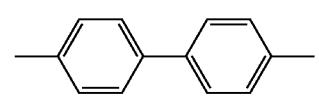 | H | H | H | 1 | 0 |
| XVI-91 | H | H | H | H | H | none | O |  | H | H | H | 1 | 0 |
| XVI-92 | H | H | H | H | H | none | S |  | H | H | H | 1 | 0 |
| XVI-93 | H | H | CH₃ | H | H | SO₂ | O | 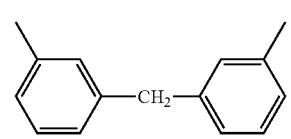 | H | H | H | 1 | 0 |
| XVI-94 | H | H | H | H | H | none | O |  | H | H | H | 1 | 0 |
| XVI-95 | H | H | H | H | H | none | S |  | H | H | H | 1 | 0 |
| XVI-96 | H | H | CH₃ | H | H | SO₂ | O | 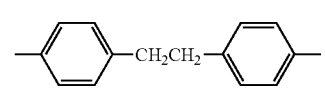 | H | H | H | 1 | 0 |
| XVI-97 | H | H | H | H | H | none | O |  | H | H | H | 1 | 0 |
| XVI-98 | H | H | H | H | H | none | S |  | H | H | H | 1 | 0 |
| XVI-99 | H | H | CH₃ | H | H | SO₂ | O | 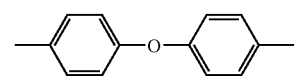 | H | H | H | 1 | 0 |
| XVI-100 | H | H | H | H | H | none | O |  | H | H | H | 1 | 0 |
| XVI-101 | H | H | H | H | H | none | S |  | H | H | H | 1 | 0 |
| XVI-102 | H | H | CH₃ | H | H | SO₂ | O | 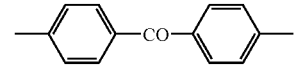 | H | H | H | 1 | 0 |
| XVI-103 | H | H | H | H | H | none | O |  | H | H | H | 1 | 0 |
| XVI-104 | H | H | H | H | H | none | S |  | H | H | H | 1 | 0 |
| XVI-105 | H | H | CH₃ | H | H | SO₂ | O | 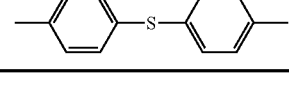 | H | H | H | 1 | 0 |
| XVI-106 | H | H | H | H | H | none | O |  | H | H | H | 1 | 0 |
| XVI-107 | H | H | H | H | H | none | S |  | H | H | H | 1 | 0 |
| XVI-108 | H | H | CH₃ | H | H | SO₂ | O |  | H | H | H | 1 | 0 |
| XVI-109 | H | H | H | H | H | none | O |  | H | H | H | 1 | 0 |
| XVI-110 | H | H | H | H | H | none | S |  | H | H | H | 1 | 0 |

TABLE 12

| Compound No. | (OH)t, (R¹)p 2- | 3- | 4- | 5- | 6- | $Y^4$ | $R^7$ | $R^3$ | $R^4$ | a | m |
|---|---|---|---|---|---|---|---|---|---|---|---|
| XVII-1 | H | H | H | H | H | CO | H | H | H | 1 | 0 |
| XVII-2 | H | H | H | H | H | CO | H | H | H | 1 | 1 |
| XVII-3 | H | H | H | H | H | CO | H | H | H | 1 | 2 |
| XVII-4 | H | H | H | H | H | CO | H | H | H | 2 | 0 |
| XVII-5 | H | H | H | H | H | CO | H | H | H | 2 | 1 |
| XVII-6 | H | H | H | H | H | CO | H | H | H | 2 | 2 |
| XVII-7 | OH | H | H | H | H | CO | H | H | H | 1 | 0 |
| XVII-8 | OH | H | H | H | H | CO | H | H | H | 1 | 1 |
| XVII-9 | OH | H | H | H | H | CO | H | H | H | 1 | 2 |
| XVII-10 | OH | H | H | H | H | CO | H | H | H | 2 | 0 |
| XVII-11 | OH | H | H | H | H | CO | H | H | H | 2 | 1 |
| XVII-12 | OH | H | H | H | H | CO | H | H | H | 2 | 2 |
| XVII-13 | H | H | OH | H | H | CO | H | H | H | 1 | 0 |
| XVII-14 | H | H | OH | H | H | CO | H | H | H | 1 | 1 |
| XVII-15 | H | H | OH | H | H | CO | H | H | H | 1 | 2 |
| XVII-16 | H | H | OH | H | H | CO | H | H | H | 2 | 0 |
| XVII-17 | H | H | OH | H | H | CO | H | H | H | 2 | 1 |
| XVII-18 | H | H | OH | H | H | CO | H | H | H | 2 | 2 |
| XVII-19 | OH | H | OH | H | H | CO | H | H | H | 1 | 0 |
| XVII-20 | $CH_3$ | H | H | H | H | CO | H | H | H | 1 | 0 |
| XVII-21 | H | $CH_3$ | H | H | H | CO | H | H | H | 1 | 0 |
| XVII-22 | H | H | $CH_3$ | H | H | CO | H | H | H | 1 | 0 |
| XVII-23 | $OCH_3$ | H | H | H | H | CO | H | H | H | 1 | 0 |
| XVII-24 | H | $OCH_3$ | H | H | H | CO | H | H | H | 1 | 0 |
| XVII-25 | H | H | $OCH_3$ | H | H | CO | H | H | H | 1 | 0 |
| XVII-26 | Cl | H | H | H | H | CO | H | H | H | 1 | 0 |
| XVII-27 | H | Cl | H | H | H | CO | H | H | H | 1 | 0 |
| XVII-28 | H | H | Cl | H | H | CO | H | H | H | 1 | 0 |
| XVII-29 | $CO_2H$ | H | H | H | H | CO | H | H | H | 1 | 0 |
| XVII-30 | H | $CO_2H$ | H | H | H | CO | H | H | H | 1 | 0 |
| XVII-31 | H | H | $CO_2H$ | H | H | CO | H | H | H | 1 | 0 |
| XVII-32 | $NO_2$ | H | H | H | H | CO | H | H | H | 1 | 0 |
| XVII-33 | H | $NO_2$ | H | H | H | CO | H | H | H | 1 | 0 |
| XVII-34 | H | H | $NO_2$ | H | H | CO | H | H | H | 1 | 0 |
| XVII-35 | $CO_2CH_3$ | H | H | H | H | CO | H | H | H | 1 | 0 |
| XVII-36 | $CONH_2$ | H | H | H | H | CO | H | H | H | 1 | 0 |
| XVII-37 | $CONHCH_3$ | H | H | H | H | CO | H | H | H | 1 | 0 |
| XVII-38 | $CON(CH_3)_2$ | H | H | H | H | CO | H | H | H | 1 | 0 |
| XVII-39 | CONHPh | H | H | H | H | CO | H | H | H | 1 | 0 |
| XVII-40 | H | H | H | H | H | CO | $CH_3$ | H | H | 1 | 0 |
| XVII-41 | H | H | H | H | H | CO | Ph | H | H | 1 | 0 |
| XVII-42 | H | H | H | H | H | CO | $CH_2Ph$ | H | H | 1 | 0 |
| XVII-43 | H | H | H | H | H | CO | 4-$CH_3$—Ph | H | H | 1 | 0 |
| XVII-44 | H | H | H | H | H | CO | H | $CH_3$ | H | 1 | 0 |
| XVII-45 | H | H | H | H | H | CO | H | $CH_3$ | $CH_3$ | 1 | 0 |
| XVII-46 | $CH_3$ | H | $CH_3$ | H | H | CO | H | H | H | 1 | 0 |
| XVII-47 | OH | H | $CH_3$ | H | H | CO | H | H | H | 1 | 0 |
| XVII-48 | $CH_2CH_3$ | H | H | H | H | CO | H | H | H | 1 | 0 |
| XVII-49 | H | H | H | H | H | $SO_2$ | H | H | H | 1 | 0 |
| XVII-50 | H | H | H | H | H | $SO_2$ | H | H | H | 1 | 1 |
| XVII-51 | H | H | H | H | H | $SO_2$ | H | H | H | 1 | 2 |
| XVII-52 | H | H | H | H | H | $SO_2$ | H | H | H | 2 | 0 |
| XVII-53 | H | H | H | H | H | $SO_2$ | H | H | H | 2 | 1 |
| XVII-54 | H | H | H | H | H | $SO_2$ | H | H | H | 2 | 2 |
| XVII-55 | OH | H | H | H | H | $SO_2$ | H | H | H | 1 | 0 |
| XVII-56 | OH | H | H | H | H | $SO_2$ | H | H | H | 1 | 1 |
| XVII-57 | OH | H | H | H | H | $SO_2$ | H | H | H | 1 | 2 |
| XVII-58 | OH | H | H | H | H | $SO_2$ | H | H | H | 2 | 0 |
| XVII-59 | OH | H | H | H | H | $SO_2$ | H | H | H | 2 | 1 |
| XVII-60 | OH | H | H | H | H | $SO_2$ | H | H | H | 2 | 2 |
| XVII-61 | H | H | OH | H | H | $SO_2$ | H | H | H | 1 | 0 |
| XVII-62 | H | H | OH | H | H | $SO_2$ | H | H | H | 1 | 1 |
| XVII-63 | H | H | OH | H | H | $SO_2$ | H | H | H | 1 | 2 |
| XVII-64 | H | H | OH | H | H | $SO_2$ | H | H | H | 2 | 0 |
| XVII-65 | H | H | OH | H | H | $SO_2$ | H | H | H | 2 | 1 |
| XVII-66 | H | H | OH | H | H | $SO_2$ | H | H | H | 2 | 2 |
| XVII-67 | OH | H | OH | H | H | $SO_2$ | H | H | H | 1 | 0 |
| XVII-68 | $CH_3$ | H | H | H | H | $SO_2$ | H | H | H | 1 | 0 |
| XVII-69 | H | $CH_3$ | H | H | H | $SO_2$ | H | H | H | 1 | 0 |
| XVII-70 | H | H | $CH_3$ | H | H | $SO_2$ | H | H | H | 1 | 0 |
| XVII-71 | $OCH_3$ | H | H | H | H | $SO_2$ | H | H | H | 1 | 0 |
| XVII-72 | H | $OCH_3$ | H | H | H | $SO_2$ | H | H | H | 1 | 0 |
| XVII-73 | H | H | $OCH_3$ | H | H | $SO_2$ | H | H | H | 1 | 0 |
| XVII-74 | Cl | H | H | H | H | $SO_2$ | H | H | H | 1 | 0 |
| XVII-75 | H | Cl | H | H | H | $SO_2$ | H | H | H | 1 | 0 |

TABLE 12-continued

| Compound No. | 2- | 3- | 4- | 5- | 6- | $Y^4$ | $R^7$ | $R^3$ | $R^4$ | a | m |
|---|---|---|---|---|---|---|---|---|---|---|---|
| XVII-76 | H | H | Cl | H | H | $SO_2$ | H | H | H | 1 | 0 |
| XVII-77 | $CO_2H$ | H | H | H | H | $SO_2$ | H | H | H | 1 | 0 |
| XVII-78 | H | $CO_2H$ | H | H | H | $SO_2$ | H | H | H | 1 | 0 |
| XVII-79 | H | H | $CO_2H$ | H | H | $SO_2$ | H | H | H | 1 | 0 |
| XVII-80 | H | $NO_2$ | H | H | H | $SO_2$ | H | H | H | 1 | 0 |
| XVII-81 | $CO_2CH_3$ | H | H | H | H | $SO_2$ | H | H | H | 1 | 0 |
| XVII-82 | $SO_2NH_2$ | H | H | H | H | $SO_2$ | H | H | H | 1 | 0 |
| XVII-83 | $SO_2NHCH_3$ | H | H | H | H | $SO_2$ | $CH_3$ | H | H | 1 | 0 |
| XVII-84 | $SO_2N(CH_3)_2$ | H | H | H | H | $SO_2$ | H | H | H | 1 | 0 |
| XVII-85 | $SO_2NHPh$ | H | H | H | H | $SO_2$ | Ph | H | H | 1 | 0 |
| XVII-86 | H | H | H | H | H | $SO_2$ | $CH_3$ | H | H | 1 | 0 |
| XVII-87 | H | H | H | H | H | $SO_2$ | Ph | H | H | 1 | 0 |
| XVII-88 | H | H | H | H | H | $SO_2$ | $CH_2Ph$ | H | H | 1 | 0 |
| XVII-89 | H | H | H | H | H | $SO_2$ | 4-$CH_3$-Ph | H | H | 1 | 0 |
| XVII-90 | H | H | H | H | H | $SO_2$ | H | $CH_3$ | H | 1 | 0 |
| XVII-91 | H | H | H | H | H | $SO_2$ | H | $CH_3$ | $CH_3$ | 1 | 0 |

The present invention can be used for many purposes, for example, recording materials using a color developing dye, such as thermal sensitive recording material and pressure sensitive copying material.

When the present invention is applied to a thermal sensitive recording paper, the same manner as in the case of using known image storage stabilizers and developers may be conducted. For example, the thermal sensitive recording paper can be produced by separately dispersing fine particles of the compound of the present invention and fine particles of a color developing dye in an aqueous solution of a water-soluble binder such as polyvinyl alcohol or cellulose to obtain suspensions, mixing the suspensions, coating a support such as paper with the mixture, and drying the coated support.

The amount of the compound represented by the formula (I) is from 1 to 10 parts by weight, and preferably from 1.5 to 5 parts by weight, based on 1 part by weight of the color developing dye.

If necessary, the recording material of the present invention can contain one or two or more kinds of publicly known developers, image stabilizers, sensitizers, fillers, dispersants, antioxidants, desensitizers, antitack agents, antifoaming agents, photostabilizers and fluorescent whitening agents, in addition to color developing dyes and the compound represented by the formula (I).

Although a color developing layer may contain these chemicals, an optional layer such as a protective layer may contain them when the recording material has a multi-layered structure. When an overcoat layer and an undercoat layer are provided on the upper portion and/or the lower portion of the color developing layer, these layers can contain antioxidants and photostabilizers. If necessary, these layers can contain antioxidants and photostabilizers in the form of being included in microcapsules.

Examples of the color developing dye used in the recording material of the present invention include, but are not limited to, color developing dyes capable of developing color by contacting with a developer as an acidic substance, for example, fluorane-based, phthalide-based, lactam-based, triphenylmethane-based, phenothiazine-based and spiropyran-based leuco dyes. As a matter of course, these color developing dyes are used alone and recording materials with color developed by each color developing dye, and can also be used in combination. For example, a recording material capable of substantially developing black color can be produced by using color developing dyes capable of developing three primary colors such as red, blue and green colors in combination with a dye capable of developing black color.

Examples of the fluorane-based color developing dye include 3-diethylamino-6-methyl-7-anilinofluorane, 3-dibutylamino-6-methyl-7-anilinofluorane, 3-(N-ethyl-N-isobutylamino)-6-methyl-7-anilinofluorane, 3-(N-methyl-N-propylamino)-6-methyl-7-anilinofluorane, 3-(N-ethyl-N-isopentylamino)-6-methyl-7-anilinofluorane, 3-diethylamino-7-(o-chloroanilino)fluorane, 3-dibutylamino-7-(o-chloroanilino)fluorane, 3-(N-ethyl-p-toluidino)-6-methyl-7-anilinofluorane, 3-(N-cyclohexyl-N-methylamino)-6-methyl-7-anilinofluorane, 3-pyrrolidino-6-methyl-7-anilinofluorane, 3-piperidino-6-methyl-7-anilinofluorane, 3-dimethylamino-7-(m-trifluoromethylanilino)fluorane, 3-dipentylamino-6-methyl-7-anilinofluorane, 3-(N-ethoxypropyl-N-ethylamino)-6-methyl-7-anilinofluorane, 3-dibutylamino-7-(o-fluoroanilino)fluorane, 3-diethylaminobenzo[a]fluorane, 3-dimethylamino-6-methyl-7-chlorofluorane, 3-diethylamino-5-methyl-7-dibenzylaminofluorane, 3-diethylamino-7-dibenzylaminofluorane, 3-diethylamino-5-chlorofluorane, 3-diethylamino-6-(N,N'-dibenzylamino)fluorane, 3,6-dimethoxyfluorane, and 2,4-dimethyl-6-(4-dimethylaminophenyl)aminofluorane.

Examples of the near infrared absorption dye include 3-{4-[4-(4-anilino)-anilino]anilino}-6-methyl-7-chlorofluorane, 3,3-bis[2-(4-dimethylaminophenyl)-2-(4-methoxyphenyl)vinyl]-4,5,6,7-tetrachlorophthalide, and 3,6,6'-tris(dimethylamino)spiro(fluorene-9,3'-phthalide).

Also 3,3-bis(4'-diethylaminophenyl)-6-diethylaminophthalide is exemplified.

Examples of the developer include bisphenol compounds such as bisphenol A, 4,4'-sec-butylidenebisphenol, 4,4'-cyclohexylidenebisphenol, 2,2-dimethyl-3,3-bis(4-hydroxyphenyl)butane, 2,2'-dihydroxydiphenyl, pentamethylene-bis(4-hydroxybenzoate), 2,2-dimethyl-3,3-di(4-hydroxyphenyl)pentane, and 2,2-di(4-hydroxyphenyl)hexane; sulfur-containing bisphenol compounds such as 4,4'-dihydroxydiphenylthioether, 1,7-di(4-hydroxyphenylthio)-3,5-dioxaheptane, 2,2'-bis(4-hydroxyphenylthio) diethyl ether, and 4,4'-dihydroxy-3,3'-dimethyldiphenylthioether;

4-hydroxybenzoate such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, and diphenylmethyl 4-hydroxybenzoate; benzoic acid metal salts such as zinc benzoate and zinc 4-nitrobenzoate; salicylic acids such as 4-[2-(4-methoxyphenyloxy)ethyloxy]salicylic acid; salicylic acid metal salts such as zinc salicylate and zinc bis[4-(octyloxycarbonylamino)-2-hydroxybenzoate];

hydroxysulfones such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-benzyloxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone, and 4,4'-dihydroxy-3,3',5,5'-tetrabromodiphenylsulfone; benzenesulfonamides such as N-(2-hydroxyphenyl)benzenesulfonamide, N-(2-hydroxyphenyl)-p-toluenesulfonamide, N-(2-hydroxyphenyl)-p-ethylbenzenesulfonamide, N-(2-hydroxyphenyl)-p-methoxybenzenesulfonamide, N-(2-hydroxyphenyl)-p-chlorobenzenesulfonamide, N-(2-hydroxyphenyl)-p-phenylbenzenesulfonamide, N-(2-hydroxyphenyl)-p-allylbenzenesulfonamide, and N-(2-hydroxyphenyl)-p-benzylbenzenesulfonamide;

4-hydroxyphthalic acid diesters such as dimethyl 4-hydroxyphthalate, dicyclohexyl 4-hydroxyphthalate, and diphenyl 4-hydroxyphthalate; esters of hydroxynaphthoic acid, such as 2-hydroxy-6-carboxynaphthalene; trihalomethylsulfones such as tribromomethylphenylsulfone; sulfonyl ureas such as 4,4'-bis(p-toluenesulfonylaminocarbonylamino)diphenylmethane; hydroxyacetophenone, p-phenylphenol, benzyl 4-hydroxyphenylacetate, p-benzylphenol, hydroquinone-monobenzyl ether, tetracyanoquinodimethanes, 2'-hydroxy-(4-hydroxyphenylthio)acetanilide, 3'-hydroxy-(4-hydroxyphenylthio)acetanilide, 4'-hydroxy-(4-hydroxyphenylthio)acetanilide, 2,4-dihydroxy-2'-methoxybenzanilide; and diphenylsulfone crosslinking compounds represented by the formula (27):

robenzyl) oxalate, dimethyl phthalate, dimethyl terephthalate, dibenzyl terephthalate, dibenzyl isophthalate, terephthalate, dibenzyl terephthalate, dibenzyl isophthalate, bis(t-butylphenol);

diphenylsulfone and derivatives thereof; diethers of 4,4'-dihydroxydiphenylsulfone, such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, and 4,4'-dihexyloxydiphenylsulfone; diethers of 2,4'-dihydroxydiphenylsulfone, such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone, and 2,4'-dihexyloxydiphenylsulfone;

1,2-bis(phenoxy)ethane, 1,2-bis(4-methylphenoxy)ethane, 1,2-bis(3-methylphenoxy)ethane, 2-naphthol benzyl ether, diphenylamine, carbazole, 2,3-di-m-tolylbutane, 4-acetylbiphenyl, 4-benzylbiphenyl, 4,4'-dimethylbiphenyl, m-terphenyl, di-B-naphthylphenylenediamine, 1-hydroxynaphthoic acidphenyl, 2-naphthylbenzyl ether, 4-methylphenyl-biphenyl ether, 2,2-bis(3,4-dimethylphenyl)ethane, 2,3,5,6-tetramethyl-4'-methyldiphenylmethane, and diphenyl carbonate.

Examples of usable filler include silica, clay, kaolin, calcined kaolin, talc, satin white, aluminum hydroxide, calcium carbonate, magnesium carbonate, zinc oxide, titanium oxide, plastic pigment. In the recording material of the present invention, salts of an alkali earth metal are preferable and carbonates thereof are more preferable, and calcium carbonate and magnesium carbonate are suitable. The amount of the filler is from 0.1 to 15 parts by weight, and preferably from 1 to 10 parts by weight, based on 1 part by weight of the color developing dye. Also, other fillers can be used in combination.

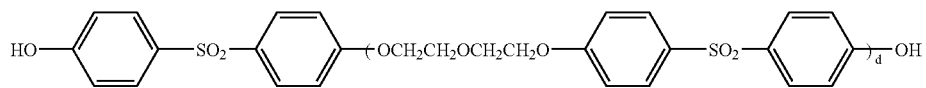

(27)

(where d is an integer of 0–10) or mixtures thereof.

Examples of the image stabilizer include epoxy group-containing diphenylsulfones such as 4-benzyloxy-4'-(2-methylglycidyloxy)-diphenylsulfone and 4,4'-diglycidyloxydiphenylsulfone; 1,4-diglycidyloxybenzene, 4-[α-(hydroxymethyl)benzyloxy]-4'-hydroxydiphenylsulfone, 2-propanol derivative, salicylic acid derivative, metal salt (especially zinc salt) of oxynaphthoic acid derivative, metal salt of 2,2-methylenebis(4,6-t-butylphenyl)phosphate, and water-insoluble zinc compound.

Examples of the sensitizer include higher fatty acid amides such as stearamide, oleamide, N-methylstearamide, erucamide, methylolbehenamide, methylenebisstearamide, and ethylenebisstearamide; higher fatty acid anilides such as stearanilide and linolanilide; amides such as benzamide and benzylamide; anilides such as acetoacetanilide, 4-acetotoluidide, salicylanilide, 4-hydroxybenzanilide, and thioacetanilide; dibenzyl oxalate, di(4-methylbenzyl) oxalate, di(4-chlo- Examples of the dispersant include sulfosuccinate such as dioctyl sodium sulfosuccinate; sodium dodecylbenzenesulfonate, and sodium salts and fatty acid salts of lauryl alcohol sulfate.

Examples of the antioxidant include 2,2'-methylenebis(4-methyl-6-t-butylphenol), 2,2'-methylenebis(4-ethyl-6-t-butylphenol), 4,4'-propylmethylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, and 4-{4-[1,1-bis(4-hydroxyphenyl)ethyl]-α,α-dimethylbenzyl}phenol.

Examples of the desensitizer include aliphatic higher alcohol, polyethylene glycol, and guanidine derivative.

Examples of the antitack agent include stearic acid, zinc stearate, calcium stearate, carnauba wax, paraffin wax, and ester wax.

Examples of the photostabilizer include salicylic acid-based ultraviolet absorbents such as phenyl salicylate, p-t-butylphenyl salicylate, and p-octylphenyl salicylate; benzophenone-based ultraviolet absorbents such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane; benzotriazole-based ultraviolet absorbents such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-[2'-hydroxy-3"-(3",4",5",6"-tetrahydrophthalamidemethyl)-5'-methylphenyl]benzotriazole, 2-(2'-hydroxy-5'-t-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, and condensate of polyethylene glycol and methyl-3-[3-t-butyl-5-(2H-benzotriazol-2-yl)-4-hydroxyphenyl]propionate;

cyano acrylate-based ultraviolet absorbents such as 2'-ethylhexyl-2-cyano-3,3-diphenyl acrylate and ethyl-2-cyano-3,3-diphenyl acrylate; hindered amine-based ultraviolet absorbents such as bis(2,2,6,6-tetramethyl-4-piperidyl)sebacate, succinic acid-bis(2,2,6,6-tetramethyl-4-piperidyl)ester, 2-(3,5-di-t-butyl)malonic acid-bis(1,2,2,6,6-pentamethyl-4-piperidyl)ester; and 1,8-dihydroxy-2-acetyl-3-methyl-6-methoxynaphthalene.

Examples of the fluorescent dye include 4,4'-bis[2-anilino-4-(2-hydroxyethyl)amino-1,3,5-triazinyl-6-amino]stilbene-2,2'disulfonic acid=disodium salt, 4,4'-bis[2-anilino-4-bis(hydroxyethyl)amino-1,3,5-triazinyl-6-bis[2-anilino-4-bis(hydroxyethyl)amino-1,3,5-triazinyl-6-amino]stilbene-2,2'-disulfonic acid=disodium salt, 4,4'-bis[2-methoxy-4-(2-hydroxyethyl)amino-1,3,5-triazinyl-6-amino]stilbene-2,2'-disulfonic acid=disodium salt, 4,4'-bis[2-methoxy-4-(2-hydroxypropyl)amino-1,3,5-triazinyl-6-amino]stilbene-2,2'-disulfonic acid=disodium salt, 4,4'-bis[2-methoxy-4-(2-hydroxypropyl)amino-1,3,5-triazinyl-6-amino]stilbene-2,2'-disulfonic acid=disodium salt, 4,4'-bis[2-m-sulfoanilino-4-bis(hydroxyethyl)amino-1,3,5-triazinyl-6-amino]stilbene-2,2'-disulfonic acid=disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid=tetrasodium salt, 4,4'-bis[2-p-sulfoanilino-4-bis(hydroxyethyl)amino-1,3,5-triazinyl-6-amino]stilbene-2,2'-disulfonic acid=tetrasodium salt, 4,4'-bis[2-(2,5-disulfoanilino)-4-phenoxyamino-1,3,5-triazinyl-6-amino]stilbene-2,2'-disulfonic acid=hexasodium salt, 4,4'-bis[2-(2,5-disulfoanilino)-4-(p-methoxycarbonylphenoxy)amino-1,3,5-triazinyl-6-amino]stilbene-2,2'-disulfonic acid=hexasodium salt, 4,4'-bis[2-(p-sulfophenoxy)-4-bis(hydroxyethyl)amino-1,3,5-triazinyl-6-amino]stilbene-2,2'-disulfonic acid=tetrasodium salt, 4,4'-bis[2-(2,5-disulfoanilino)-4-formalinylamino-1,3,5-triazinyl-6-amino]stilbene-2,2'-disulfonic acid=hexasodium salt, and 4,4'-bis[2-(2,5-disulfoanilino)-4-bis(hydroxyethyl)amino-1,3,5-triazinyl-6-amino]stilbene-2,2'-disulfonic acid=hexasodium salt.

When the compound of the present invention is used in a pressure sensitive copying paper, it can be produced in the same manner as in the case of using known image storage stabilizers, sensitizers and developers. For example, a color developing agent sheet is made by dispersing a color developing dye, which is microcapsulated by a publicly known method, using a suitable dispersant, and coating a paper with the resulting dispersion. Also a developer sheet is made by coating a paper with a dispersion of a developer. When the compound of the present invention is used as an image storage stabilizer, it may be dispersed in a dispersion of either of a color developing agent sheet and a developer sheet. Both sheets thus obtained are combined to obtain a pressure sensitive copying paper. The pressure sensitive copying paper may be a unit composed of a coated-back paper comprising microcapsules including an organic solvent solution of a color developing dye coated and supported on the lower surface, and a coated-front paper comprising a developer (acidic substance) coated and supported on the upper surface, or a so-called self content paper wherein microcapsules and a developer are coated on the same paper surface.

The developer, or developer used in combination with the compound of the present invention may be conventionally known developers and examples thereof include inorganic acidic substances such as acid clay, activated clay, attapulgite, bentonite, colloidal silica, aluminum silicate, magnesium silicate, zinc silicate, tin silicate, calcined kaolin, and talc; aliphatic carboxylic acids such as oxalic acid, maleic acid, tartaric acid, citric acid, succinic acid, and stearic acid; aromatic carboxylic acids such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3,5-di-t-butylsalicylic acid, 3-methyl-5-benzylsalicylic acid, 3-phenyl-5-(2,2-dimethylbenzyl)salicylic acid, 3,5-di-(2-methylbenzyl)salicylic acid, and 2-hydroxy-1-benzyl-3-naphthoic acid, and salts of metals such as zinc, magnesium, aluminum and titanium of these aromatic carboxylic acids; phenol resin-based developers such as p-phenylphenol-formalin resin and p-butylphenol-acetylene resin; and mixtures of these phenol resin-based developers and metal salts of the aromatic carboxylic acids.

Examples of the support used in the present invention include conventionally known papers, synthetic papers, films, plastic films, foamed plastic films, nonwoven fabrics, and regenerated papers such as waste paper pulp. These materials can also be used in combination as the support.

BEST MODE FOR CARRYING OUT THE INVENTION

The compound of the present invention will now be described in more detail by way of examples. In the following examples, parts are by weight unless otherwise specified.

1) Examples to Phenolic Compounds Represented by the Formula (XII)

EXAMPLE 1

Synthesis of 4-(4-hydroxyphenylthiomethyl)-N-phenylbenzamide (Compound No. XII-248)

In a 200 ml four-necked flask equipped with a stirrer and a thermometer, 1.34 g (10.6 mmol) of 4-mercaptophenol, 0.7 g (10.6 mmol) of potassium hydroxide and 50 ml of methanol were added at room temperature. After confirming that potassium hydroxide has been dissolved, the inner temperature was cooled to 10° C. and 2.6 g (10.6 mmol) of 4-chloromethyl-N-phenylbenzamide was added, followed by stirring at room temperature for 3 hours. After the completion of the reaction, the reaction solution was acidified with hydrochloric acid and 50 ml of water was added, and then the deposited crystal was collected by filtration to obtain 3.0 g of 4-(4-hydroxyphenylthiomethyl)-N-phenylbenzamide. The yield was 84%. The melting point was 220–222° C.

EXAMPLE 2

Synthesis of 4-(4-hydroxyphenylthiomethyl)-N-(2-hydroxyphenyl)benzamide (Compound No. XII-267)

In the same manner as in Example 1, except that 4-chloromethyl-N-(2-hydroxyphenyl)benzamide was used in place of 4-chloromethyl-N-phenylbenzamide in Example 1, the reaction was conducted. The melting point was 152–156° C.

EXAMPLE 3

Synthesis of 4-(4-hydroxyphenylthiomethyl)-N-(3-hydroxyphenyl)benzamide (Compound No. XII-264)

In the same manner as in Example 1, except that 4-chloromethyl-N-(3-hydroxyphenyl)benzamide was used in place of 4-chloromethyl-N-phenylbenzamide in Example 1, the reaction was conducted. The melting point was 218–222° C.

EXAMPLE 4

Synthesis of 4-(4-hydroxyphenylsulfonylmethyl)-N-(2-hydroxyphenyl)benzamide (Compound No. XII-269)

In a 200 ml four-necked flask equipped with a stirrer and a thermometer, 3.2 g (9.11 mmol) of the compound synthesized in Example 2 and 100 ml of ethyl acetate were charged at normal temperature. The inner temperature was cooled to 10° C. and 3.14 g (18.2 mmol) of 70% m-chloroperbenzoic acid was added, followed by stirring at normal temperature for 3 hours. After the completion of the reaction, dimethyl sulfur was added thereby to decompose excess peroxide, and then the deposited crystals were collected by filtration to obtain 3.0 g of 4-(4-hydroxyphenylsulfonylmethyl)-N-(2-hydroxyphenyl)benzamide. The yield was 86% and the melting point was 250° C. or higher.

EXAMPLE 5

| Dye dispersion (solution A) | |
|---|---|
| 3-di-n-butylamino-6-methyl-7-anilinofluorane | 16 Parts |
| Aqueous 10% polyvinyl alcohol solution | 84 Parts |
| Developer dispersion (solution B) | |
| 4-(4-hydroxyphenylthiomethyl)-N-phenylbenzamide | 16 Parts |
| Aqueous 10% polyvinyl alcohol solution | 84 Parts |
| Filler dispersion (solution C) | |
| Calcium carbonate | 27.8 Parts |
| Aqueous 10% polyvinyl alcohol solution | 26.2 Parts |
| Water | 71 Parts |

Each component for solutions A to C was sufficiently ground using a sand grinder to obtain dispersion solutions A to C, and a coating solution was prepared by mixing 1 part by weight of the dispersion solution A, 2 parts by weight of the dispersion solution B and 4 parts by weight of the dispersion solution C. Using a wire rod (No. 12), a white paper was coated with the resulting coating solution and the coated white paper was dried and then subjected to a calendering treatment to obtain a thermal sensitive recording paper (coating weight is about 5.5 g/m$^2$ on a dry basis).

EXAMPLE 6

In the same manner as in Example 5, except that 4-(4-hydroxyphenylthiomethyl)-N-(2-hydroxyphenyl)benzamide was used in place of 4-(4-hydroxyphenylthiomethyl)-N-phenylbenzamide in the developer dispersion (solution B) of Example 5, a thermal sensitive recording paper was made.

EXAMPLE 7

In the same manner as in Example 5, except that 4-(4-hydroxyphenylthiomethyl)-N-(3-hydroxyphenyl)benzamide was used in place of 4-(4-hydroxyphenylthiomethyl)-N-phenylbenzamide in the developer dispersion (solution B) of Example 5, a thermal sensitive recording paper was made.

COMPARATIVE EXAMPLE 1

In the same manner as in Example 5, except that 2'-hydroxy-(4-hydroxyphenylthio)acetanilide was used in place of 4-(4-hydroxyphenylthiomethyl)-N-phenylbenzamide in the developer dispersion (solution B) of Example 5, a thermal sensitive recording paper was made.

COMPARATIVE EXAMPLE 2

In the same manner as in Example 5, except that 2,4'-dihydroxydiphenylsulfone was used in place of 4-(4-hydroxyphenylthiomethyl)-N-phenylbenzamide in the developer dispersion (solution B) of Example 5, a thermal sensitive recording paper was made.

TEST EXAMPLE 1

Test on Light Resistance of Background

A portion of each of thermal sensitive recording papers made in Examples 5 to 7 and Comparative Examples 1 and 2 was cut out and was used as a test paper. Using a light resistance testing machine (manufactured by Suga Test Instruments Co., Ltd. under the trade name of Ultraviolet Long Life Fade Meter, Model FAL-5), the background density of each test paper after irradiation with ultraviolet light having a wavelength of 380 nm for 12 hours was measured. The resulting background density was compared with the original background density. The measurement results are shown in Table 13.

TEST EXAMPLE 2

Test on Heat Resistance of Background

A portion of each of thermal sensitive recording papers made in Examples 5 to 7 and Comparative Examples 1 and 2 was cut out and was used as a test paper. Each test paper was allowed to stand in a constant-temperature oven (Model DK-400, manufactured by YAMATO) at 100° C. for 24 hours and the background density was measured. The resulting background density was compared with the original background density. The measurement results are shown in Table 13.

TEST EXAMPLE 3

Test on Light Resistance of Images

A portion of each of thermal sensitive recording papers made in Examples 5 to 7 and Comparative Examples 1 and 2 was cut out and was used as a test paper. Using a thermal sensitive paper color developing apparatus (manufactured by Ohkura Electric Co., Ltd. under the trade name of Model TH-PMD), color of each test paper was developed up to the saturated condition. Using a light resistance testing machine (manufactured by Suga Test Instruments Co., Ltd. under the trade name of Ultraviolet Long Life Fade Meter, Model FAL-5), the image density of each test paper after irradiation with ultraviolet light having a wavelength of 380 nm for 48 hours was measured. The resulting image density was compared with the original image density. The measurement results are shown in Table 13.

TEST EXAMPLE 4

Test on Heat Resistance of Images

A portion of each of thermal sensitive recording papers made in Examples 5 to 7 and Comparative Examples 1 and 2 was cut out and was used as a test paper. Using a thermal sensitive paper color developing apparatus (manufactured by Ohkura Electric Co., Ltd. under the trade name of Model TH-PMD), color of each test paper was developed up to the saturated condition. Each test paper was allowed to stand in a constant-temperature oven (Model DK-400, manufactured by YAMATO) at 100° C. for 24 hours and the image density was measured. The resulting image density was compared with the original image density. The measurement results are shown in Table 13.

TABLE 13

|  | Test Example 1 | Test Example 2 | Test Example 3 | Test Example 4 |
|---|---|---|---|---|
| Example 5 | ○ | ◎ | ○ | Δ |
| Example 6 | ○ | ○ | ○ | ◎ |
| Example 7 | ○ | ◎ | ○ | Δ |
| Comparative Example 1 | ○ | ○ | ○ | Δ |
| Comparative Example 2 | ○ | Δ | Δ | ○ |

(In the table, the symbol ◎ denotes excellent, the symbol ○ denotes ordinary, and the symbol Δ denotes poor)

2) Examples to Phenolic Compounds Represented by the Formula (XIII)

EXAMPLE 8

Synthesis of S-(4-hydroxyphenyl)(4-hydroxyphenylthio)thioacetate (Compound No. XIII-5)

In a 200 ml four-necked flask equipped with a stirrer and a thermometer, 2.52 g (20 mmol) of 4-mercaptophenol, 1.32 g (20 mmol) of 85% potassium hydroxide and 50 ml of methanol were added at normal temperature. After confirming that potassium hydroxide has been dissolved, the inner temperature was cooled to 10° C. and 4.05 g (20 mmol) of S-(4-hydroxyphenyl) chlorothioacetate was added, followed by stirring at normal temperature for 3 hours. After the completion of the reaction, the reaction solution was acidified with hydrochloric acid and 50 ml of water was added, and then the deposited crystal was collected by filtration to obtain 5.0 g of S-(4-hydroxyphenyl)(4-hydroxyphenylthio) thioacetate. The yield was 86%. The melting point was 145–148° C.

EXAMPLE 9

Synthesis of S-(4-hydroxyphenyl) 4-(4-hydroxyphenylthiomethyl)thiobenzoate (Compound No. XIII-16)

In the same manner as in Example 8, except that S-(4-hydroxyphenyl) 4-chloromethylthiobenzoate was used in place of S-(4-hydroxyphenyl) chlorothioacetate in Example 8, the reaction was conducted to obtain S-(4-hydroxyphenyl) 4-(4-hydroxyphenylthiomethyl)thiobenzoate. The melting point was 202–209° C.

EXAMPLE 10

| Dye dispersion (solution A) | |
|---|---|
| 3-di-n-butylamino-6-methyl-7-anilinofluorane | 16 Parts |
| Aqueous 10% polyvinyl alcohol solution | 84 Parts |
| Developer dispersion (solution B) | |
| S-(4-hydroxyphenyl) (4-hydroxyphenylthio)thioacetate | 16 Parts |
| Aqueous 10% polyvinyl alcohol solution | 84 Parts |
| Filler dispersion (solution C) | |
| Calcium carbonate | 27.8 Parts |
| Aqueous 10% polyvinyl alcohol solution | 26.2 Parts |
| Water | 71 Parts |

A coating solution was prepared by sufficiently grinding each mixture of components for solutions A to C using a sand grinder to obtain each of the dispersions for solutions A to C, and mixing 1 part by weight of the dispersion for solution A, 2 parts by weight of the dispersion for solution B and 4 parts by weight of the dispersion for solution C. Using a wire rod (No. 12), a white paper was coated with the resulting coating solution and the coated white paper was dried and then subjected to a calendering treatment to obtain a thermal sensitive recording paper (coating weight was about 5.5 g/m² on a dry basis).

EXAMPLE 11

In the same manner as in Example 10, except that S-(4-hydroxyphenyl) 4-(4-hydroxyphenylthiomethyl)thiobenzoate was used in place of S-(4-hydroxyphenyl) (4-hydroxyphenylthio)thioacetate in the developer dispersion (solution B) of Example 10, a thermal sensitive recording paper was made.

COMPARATIVE EXAMPLE 3

In the same manner as in Example 10, except that 2,4'-dihydroxydiphenylsulfone was used in place of S-(4-hydroxyphenyl) (4-hydroxyphenylthio)thioacetate in the developer dispersion (solution B) of Example 10, a thermal sensitive recording paper was made.

TEST EXAMPLE 5

Test on Light Resistance of Images

A portion of each of thermal sensitive recording papers made in Examples 10 and 11 and Comparative Example 3 was cut out and was used as a test paper. Using a thermal sensitive paper color developing apparatus (manufactured by Ohkura Electric Co., Ltd., under the trade name of Model TH-PMD), color of each test paper was developed up to the saturated condition. Using a light resistance testing machine (manufactured by Suga Test Instruments Co., Ltd., under the trade name of Ultraviolet Long Life Fade Meter, Model FAL-5), the image density of each test paper after irradiation with ultraviolet light having a wavelength of 380 nm for 48 hours was measured. The measurement results are shown in Table 14.

Image retention (%)=(CI$_t$/CI$_0$)×100
CI$_0$: print density before test
CI$_t$: print density after t days

TABLE 14

| | Image density (upper column: Macbeth value, lower column: <retention %>) | |
|---|---|---|
| | original | Light resistance of images 48 hr |
| Comparative Example 3 | 1.26 | 0.93 <74> |
| Example 10 | 1.32 | 1.23 <93> |
| Example 11 | 1.31 | 1.26 <96> |

3) Examples to Phenolic Compounds Represented by the Formula (XIV)

EXAMPLE 12

Synthesis of S-(4-hydroxy)phenylphenylthiocarbamate (Compound No. XIV-1)

In a 100 ml four-necked flask equipped with a stirrer and a thermometer, 2.52 g (20 mmol) of 4-mercaptophenol, 0.1 g of triethylamine and 50 ml of toluene were charged at normal temperature. The inner temperature of this solution was cooled to 10° C. and 2.38 g (20 mmol) of phenyl isocyanate was added, followed by stirring at normal temperature for 3 hours. After the completion of the reaction, the deposited crystals were collected by filtration to obtain 4.4 g of S-(4-hydroxy)phenylphenylthiocarbamate. The yield was 90% and the melting point was 167–171° C.

EXAMPLE 13

Synthesis of S,S-bis(4-hydroxyphenyl)toluene-2,4-dithiocarbamate (Compound No. XIV-40)

In a 100 ml four-necked flask equipped with a stirrer and a thermometer, 2.52 g (20 mmol) of 4-mercaptophenol, 0.1 g of triethylamine and 50 ml of toluene were charged at room temperature. The inner temperature of this solution was cooled to 10° C. and 1.74 g (10 mmol) of 2,4-toluene diisocyanate was added, followed by stirring at normal temperature for 3 hours. After the completion of the reaction, the deposited crystals were collected by filtration to obtain 3.2 g of S,S-bis(4-hydroxyphenyl)toluene-2,4-dithiocarbamate. The yield was 75% and the melting point was 177–180° C.

EXAMPLE 14

Synthesis of S,S-bis(4-hydroxyphenyl) Dithiosuccinate Compound No. XIV-50)

In a 200 ml four-necked flask equipped with a stirrer and a thermometer, 5.04 g (40 mmol) of 4-mercaptophenol, 3.48 g (44 mmol) of pyridine and 100 ml of dimethoxyethane were charged at room temperature. The inner temperature of this solution was cooled to 10° C. and 3.1 g (20 mmol) of succinic acid chloride was added, followed by stirring at normal temperature for 3 hours. After the completion of the reaction, the deposited crystals were collected by filtration to obtain 5.8 g of S,S-bis(4-hydroxyphenyl) dithiosuccinate. The yield was 87% and the melting point was 226–229° C.

EXAMPLE 15

Synthesis of S,S-bis(4-hydroxyphenyl) Dithioisophthalate (Compound No. XIV-53)

In the same manner as in Example 14, except that isophthalic acid chloride was used in place of succinic acid chloride in Example 14, the reaction was conducted to obtain S,S-bis(4-hydroxyphenyl) dithioisophthalate. The melting point was 218–221° C.

EXAMPLE 16

| Dye dispersion (solution A) | |
|---|---|
| 3-di-n-butylamino-6-methyl-7-anilinofluorane | 16 Parts |
| Aqueous 10% polyvinyl alcohol solution | 84 Parts |
| Developer dispersion (solution B) | |
| S-(4-hydroxy)phenylphenylthiocarbamate | 16 Parts |
| Aqueous 10% polyvinyl alcohol solution | 84 Parts |
| Filler dispersion (solution C) | |
| Calcium carbonate | 27.8 Parts |
| Aqueous 10% polyvinyl alcohol solution | 26.2 Parts |
| Water | 71 Parts |

A coating solution was prepared by sufficiently grinding each mixture of components for solutions A to C using a sand grinder to obtain each of the dispersions for solutions A to C, and mixing 1 part by weight of the dispersion for solution A, 2 parts by weight of the dispersion for solution B, and 4 parts by weight of the dispersion for solution C. Using a wire rod (No. 12), a white paper was coated with the resulting coating solution and the coated white paper was dried and then subjected to a calendering treatment to obtain a thermal sensitive recording paper (coating weight was about 5.5 g/m² on a dry basis).

EXAMPLE 17

In the same manner as in Example 16, except that S,S-bis(4-hydroxyphenyl)toluene-2,4-dithiocarbamate was used in place of S-(4-hydroxy)phenylphenylthiocarbamate in the developer dispersion (solution B) of Example 16, a thermal sensitive recording paper was made.

EXAMPLE 18

In the same manner as in Example 16, except that S,S-bis(4-hydroxyphenyl) dithiosuccinate was used in place of S-(4-hydroxy)phenylphenylthiocarbamate in the developer dispersion (solution B) of Example 16, a thermal sensitive recording paper was made.

EXAMPLE 19

In the same manner as in Example 16, except that S,S-bis(4-hydroxyphenyl) dithioisophthalate was used in place of S-(4-hydroxy)phenylphenylthiocarbamate in the developer dispersion (solution B) of Example 16, a thermal sensitive recording paper was made.

COMPARATIVE EXAMPLE 4

In the same manner as in Example 16, except that 2,4'-dihydroxydiphenylsulfone was used in place of S-(4-hydroxy)phenylphenylthiocarbamate in the developer dispersion (solution B) of Example 16, a thermal sensitive recording paper was made.

TEST EXAMPLE 6

Test on Resistance of Background to Humidity and Heat

A portion of each of the thermal sensitive recording papers made in Examples 16 to 19 and Comparative Example 4 was cut out and was used as a test paper. The optical density of the background of each test paper after storing in an incubator controlled humidity and temperature for 24 hours was measured by Macbeth Densitometer (manufactured by Macbeth Co. under the trade name of RD-514, Filter used: #106). The measurement results are shown in Table 15.

TEST EXAMPLE 7

Test on Heat Resistance of Background

A portion of each of thermal sensitive recording papers made in Examples 16 to 19 and Comparative Example 4 was cut out and was used as a test paper. The background density of each test paper after standing in a constant-temperature oven (Model DK-400, manufactured by YAMATO) at 100° C. for 24 hours was measured. The measurement results are shown in Table 15.

TEST EXAMPLE 8

Test on Light Resistance of Images

A portion of each of thermal sensitive recording papers made in Examples 16 to 19 and Comparative Example 4 was cut out and was used as a test paper. Using a thermal sensitive paper color developing apparatus (manufactured by Ohkura Electric Co., Ltd. under the trade name of Model TH-PMD), color of each test paper was developed up to the saturated condition. Using a light resistance testing machine (manufactured by Suga Test Instruments Co., Ltd. under the trade name of Ultraviolet Long Life Fade Meter, Model FAL-5), the image density of each test paper after irradiation with ultraviolet light having a wavelength of 380 nm for 48 hours was measured. The measurement results are shown in Table 16.

TEST EXAMPLE 9

Test on Resistance of Images to Plasticizers

A portion of each of the thermal sensitive recording papers made in Examples 16 to 19 and Comparative Example 4 was cut out and was used as a test paper. Using a thermal sensitive paper color developing apparatus (manufactured by Ohkura Electric Co., Ltd. under the trade name of Model TH-PMD), color of each test paper was developed up to the saturated condition. A polyvinyl chloride wrapping film (Polymawrap 300) manufactured by Shin-Etsu Polymer Co., Ltd., was adhered to the color developed surface. The print density after standing at 40° C. for 16 hours was measured by Macbeth Densitometer RD-918. The measurement results are shown in Table 16.

Image retention (%) $(CI_t/CI_0) \times 100$ $CI_0$: print density before test $CI_t$: print density after t days

TABLE 15

| | Background density | | |
|---|---|---|---|
| | Original | Resistance to humidity and heat | Heat resistance |
| Comparative Example 4 | 0.11 | 0.08 | 0.14 |
| Example 16 | 0.15 | 0.10 | 0.06 |
| Example 17 | 0.08 | 0.08 | 0.07 |
| Example 18 | 0.06 | 0.05 | 0.05 |
| Example 19 | 0.06 | 0.05 | 0.05 |

TABLE 16

| | Image density (upper column: Macbeth value, lower column: <retention %>) | | |
|---|---|---|---|
| | Original | Light resistance | Resistance to plasticizers |
| Comparative Example 4 | 1.26 | 0.93<br><74> | 0.46<br><37> |
| Example 16 | 1.30 | 1.02<br><78> | 0.35<br><27> |
| Example 17 | 1.20 | 1.00<br><83> | 0.89<br><74> |
| Example 18 | 1.31 | 0.99<br><76> | 0.57<br><44> |
| Example 19 | 1.26 | 1.01<br><80> | 0.63<br><50> |

4) Examples to Phenolic Compound Represented by the Formula (XV)

EXAMPLE 20

Synthesis of 2-[(4-hydroxyphenylthio)acetamide]ethyl (4-hydroxyphenylthio)acetate (Compound No. XV-1)

In a 200 ml four-necked flask equipped with a stirrer and a thermometer, 2.52 g (20 mmol) of 4-mercaptophenol, 1.32 g (20 mmol) of 85% potassium hydroxide and 50 ml of methanol were added at normal temperature. After confirming that potassium hydroxide has been dissolved, the inner temperature was cooled to 10° C. and 2.14 g (10 mmol) of 2-(chloroacetamide)ethyl chloroacetate was added, followed by stirring at normal temperature for 3 hours. After the completion of the reaction, the reaction solution was acidified with hydrochloric acid and 50 ml of water was added, and then the deposited crystals were collected by filtration to obtain 3.5 g of 2-[(4-hydroxyphenylthio)acetamide]ethyl (4-hydroxyphenylthio)acetate. The yield was 89% and the melting point was 136–140° C.

EXAMPLE 21

Synthesis of 4-[(4-hydroxyphenylthio)acetamide]phenyl (4-hydroxyphenylthio)acetate (Compound No. XV-26)

In the same manner as in Example 20, except that 4-(chloroacetamide)phenyl chloroacetate was used in place of 2-(chloroacetamide)ethyl chloroacetate in Example 20, the reaction was conducted to obtain 4-[(4-hydroxyphenylthio)acetamide]phenyl (4-hydroxyphenylthio)acetate. The melting point was 142–146° C.

EXAMPLE 22

| Dye dispersion (solution A) | |
|---|---|
| 3-di-n-butylamino-6-methyl-7-anilinofluorane | 16 Parts |
| Aqueous 10% polyvinyl alcohol solution | 84 Parts |
| Developer dispersion (solution B) | |
| 2-[(4-hydroxyphenylthio)acetamide]ethyl (4-hydroxyphenylthio)acetate | 16 Parts |
| Aqueous 10% polyvinyl alcohol solution | 84 Parts |
| Filler dispersion (solution C) | |
| Calcium carbonate | 27.8 Parts |
| Aqueous 10% polyvinyl alcohol solution | 26.2 Parts |
| Water | 71 Parts |

A coating solution was prepared by sufficiently grinding each mixture of components for solutions A to C using a sand grinder to obtain each of the dispersions for solutions A to C, and mixing 1 part by weight of the dispersion for solution A, 2 parts by weight of the dispersion for solution B, and 4 parts by weight of the dispersion for solution C. Using a wire rod (No. 12), a white paper was coated with the resulting coating solution and the coated white paper was dried and then subjected to a calendering treatment to obtain a thermal sensitive recording paper (coating weight was about 5.5 g/m² on a dry basis).

EXAMPLE 23

In the same manner as in Example 22, except that 4-[(4-hydroxyphenylthio)acetamide]phenyl (4-hydroxyphenylthio)acetate was used in place of 2-[(4-hydroxyphenylthio)acetamide]ethyl (4-hydroxyphenylthio)acetate in the developer dispersion (solution B) of Example 22, a thermal sensitive recording paper was made.

COMPARATIVE EXAMPLE 5

In the same manner as in Example 22, except that 2,4'-dihydroxydiphenylsulfone was used in place of 2-[(4-hydroxyphenylthio)acetamide]ethyl (4-hydroxyphenylthio) acetate ester in the developer dispersion (solution B) of Example 22, a thermal sensitive recording paper was made.

TEST EXAMPLE 10

Test Resistance of Background to Humidity and Heat

A portion of each of the thermal sensitive recording papers made in Examples 22 and 23 and Comparative Example 5 was cut out and was used as a test paper. The optical density of the background of each test paper after storing in an incubator controlled humidity and temperature for 24 hours was measured by Macbeth Densitometer (manufactured by Macbeth Co. under the trade name of RD-514, Filter used: #106). The measurement results are shown in Table 17.

TEST EXAMPLE 11

Test on Light Resistance of Images

A portion of each of thermal sensitive recording papers made in Examples 22 and 23 and Comparative Example 5 was cut out and was used as a test paper. Using a thermal sensitive paper color developing apparatus (manufactured by Ohkura Electric Co., Ltd. under the trade name of Model TH-PMD), color of each test paper was developed up to the saturated condition. Using a light resistance testing machine (manufactured by Suga Test Instruments Co., Ltd. under the trade name of Ultraviolet Long Life Fade Meter, Model FAL-5), the image density of each test paper after irradiation with ultraviolet light having a wavelength of 380 nm for 48 hours was measured. The measurement results are shown in Table 17.

TEST EXAMPLE 12

Test on Heat Resistance of Images

A portion of each of thermal sensitive recording papers made in Examples 22 and 23 and Comparative Example 5 was cut out and was used as a test paper. In the same manner as in Test Example 1, color of each test paper was developed up to the saturated condition. Each test paper was allowed to stand in a constant-temperature oven (Model DK-400, manufactured by YAMATO) at 100° C. for 24 hours and the image density was measured. The measurement results are shown in Table 17.

TABLE 17

|  | Resistance of background to humidity and heat | Light resistance of images | Heat resistance of images |
| --- | --- | --- | --- |
| Comparative Example 5 | ○ | ○ | ○ |
| Example 22 | ◎ | ◎ | Δ |
| Example 23 | ◎ | ◎ | ◎ |

(In the table, the symbol ◎ denotes excellent, the symbol ○ denotes ordinary, and the symbol Δ denotes poor)

5) Examples to Phenolic Compounds Represented by the Formula (XVI)

EXAMPLE 24

Synthesis of 4-(4-hydroxyphenylthio)acetamide-4'-(4-toluenesulfonyl)ureidediphenylmethane (Compound No. XVI-3)

In a 100 ml four-necked flask equipped with a stirrer and a thermometer, 7.28 g (20 mmol) of 4-amino-4'-(4-hydroxyphenylthio)acetamidediphenylmethane and 100 ml of dimethoxyethane were charged and dissolved at normal temperature. Then, 4.33 g (22 mmol) of 4-toluenesulfonyl isocyanate was added, followed by stirring at normal temperature for 6 hours. After the completion of the reaction, the solvent was concentrated and ethyl acetate was added, and then the deposited crystals were collected by filtration to obtain 10.1 g of 4-(4-hydroxyphenylthio)acetamide-4'-(4-toluenesulfonyl)ureidediphenylmethane. The yield was 90% and the melting point was 144–147° C.

EXAMPLE 25

| Dye dispersion (solution A) | |
| --- | --- |
| 3-di-n-butylamino-6-methyl-7-anilinofluorane | 16 Parts |
| Aqueous 10% polyvinyl alcohol solution | 84 Parts |
| Developer dispersion (solution B) | |
| 4-(4-hydroxyphenylthio)acetamide-4'-(4-toluenesulfonyl)ureidediphenylmethane | 16 Parts |
| Aqueous 10% polyvinyl alcohol solution | 84 Parts |
| Filler dispersion (solution C) | |
| Calcium carbonate | 27.8 Parts |
| Aqueous 10% polyvinyl alcohol solution | 26.2 Parts |
| Water | 71 Parts |

A coating solution was prepared by sufficiently grinding each mixture of components for solutions A to C using a sand grinder to obtain each of the dispersions for solutions A to C, and mixing 1 part by weight of the dispersion for solution A, 2 parts by weight of the dispersion for solution B and 4 parts by weight of the dispersion for solution C. Using a wire rod (No. 12), a white paper was coated with the resulting coating solution and the coated white paper was dried and then subjected to a calendering treatment to obtain a thermal sensitive recording paper (coating weight was about 5.5 g/m² on a dry basis).

COMPARATIVE EXAMPLE 6

In the same manner as in Example 25, except that 2,4'-dihydroxydiphenylsulfone was used in place of 4-(4-hydroxyphenylthio)acetamide-4'-(4-toluenesulfonyl)ureidediphenylmethane in the developer dispersion (solution B) of Example 25, a thermal sensitive recording paper was made.

TEST EXAMPLE 13

Test on Light Resistance of Images

A portion of each of the thermal sensitive recording papers made in Example 25 and Comparative Example 6 was cut out and was used as a test paper. Using a thermal sensitive paper color developing apparatus (manufactured by Ohkura Electric Co., Ltd. under the trade name of Model TH-PMD), color of each test paper was developed up to the saturated condition. Using a light resistance testing machine (manufactured by Suga Test Instruments Co., Ltd. under the trade name of Ultraviolet Long Life Fade Meter, Model FAL-5), the image density of each test paper after irradiation-with ultraviolet light having a wavelength of 380 nm for 48 hours was measured. The measurement results are shown in Table 18.

TEST EXAMPLE 14

Test on Heat Resistance of Images

A portion of each of the thermal sensitive recording papers made in Example 25 and Comparative Example 6 was cut out and was used as a test paper. In the same manner as in Test Example 1, the color of each test paper was developed up to the saturated condition. Each test paper was allowed to stand in a constant-temperature oven (Model DK-400, manufactured by YAMATO) at 100° C. for 24 hours and the image density was measured. The measurement results are shown in Table 18.

TEST EXAMPLE 15

Test on Resistance of images to Plasticizers

A portion of each of the thermal sensitive recording papers made in Example 25 and Comparative Example 6 was cut out and was used as a test paper. In the same manner as in Test Example 1, color of each test paper was developed up to the saturated condition. A polyvinyl chloride wrapping film (Polymawrap 300) manufactured by Shin-Etsu Polymer Co., Ltd. was adhered to the color developed surface. The print density after standing at 40° C. for 16 hours was measured by Macbeth Densitometer RD-918. The measurement results are shown in Table 18.

Image retention (%)=$(CI_t/CI_0) \times 100$
$CI_0$: print density before test
$CI_t$: print density after t days

TABLE 18

| | Image density (upper column: Macbeth value, lower column: <retention %>) | | | |
|---|---|---|---|---|
| | Original | Light resistance of images 48 hr | Heat resistance of images 24 hr | Resistance of images to plasticizers 16 hr |
| Comparative Example 6 | 1.26 | 0.89 <71> | 0.93 <74> | 0.46 <37> |
| Example 25 | 1.26 | 0.93 <74> | 1.23 <98> | 0.91 <72> |

6) Examples to Phenolic Compounds Represented by the Formula (XVI)

EXAMPLE 26

Synthesis of N-benzoyl-(4-hydroxyphenylthio)acetamide (Compound No. XVII-1)

In a 200 ml four-necked flask equipped with a stirrer and a thermometer, 2.52 g (20 mmol) of 4-mercaptophenol, 1.32 g (20 mmol) of 85% potassium hydroxide and 50 ml of methanol were added at normal temperature. After confirming that potassium hydroxide had been dissolved, the inner temperature was cooled to 10° C. and 3.95 g (20 mmol) of N-benzoyl-chloroacetamide was added, followed by stirring at normal temperature for 3 hours. After the completion of the reaction, the reaction solution was acidified with hydrochloric acid and 50 ml of water was added, and then the deposited crystals were collected by filtration to obtain 5.0 g of N-benzoyl-(4-hydroxyphenylthio)acetamide. The yield was 87% and the melting point was 149–151° C.

EXAMPLE 27

Synthesis of N-(2-hydroxy)benzoyl-(4-hydroxyphenylthio)acetamide (Compound No. XVII-7)

In the same manner as in Example 26, except that N-(2-hydroxy)benzoyl-chloroacetamide was used in place of N-benzoyl-chloroacetamide in Example 26, the reaction was conducted to obtain N-(2-hydroxy)benzoyl-(4-hydroxyphenylthio)acetamide. The melting point was 156–158° C.

EXAMPLE 28

Synthesis of N-(4-methyl)benzenesulfonyl-(4-hydroxyphenylthio)acetamide (Compound No. XVII-70)

In the same manner as in Example 26, except that N-(4-methyl)benzenesulfonyl-chloroacetamide was used in place of N-benzoyl-chloroacetamide in Example 26, the reaction was conducted to obtain N-(4-methyl)benzenesulfonyl-(4-hydroxyphenylthio)acetamide. The melting point was 127–130° C.

EXAMPLE 29

| Dye dispersion (solution A) | |
|---|---|
| 3-di-n-butylamino-6-methyl-7-anilinofluorane | 16 Parts |
| Aqueous 10% polyvinyl alcohol solution | 84 Parts |
| Developer dispersion (solution B) | |
| N-benzoyl-(4-hydroxyphenylthio)acetamide | 16 Parts |
| Aqueous 10% polyvinyl alcohol solution | 84 Parts |
| Filler dispersion (solution C) | |
| Calcium carbonate | 27.8 Parts |
| Aqueous 10% polyvinyl alcohol solution | 26.2 Parts |
| Water | 71 Parts |

A coating solution was prepared by sufficiently grinding each mixture of components for solutions A to C using a sand grinder to obtain each of the dispersions for solutions A to C, and mixing 1 part by weight of the dispersion for solution A, 2 parts by weight of the dispersion for solution B, and 4 parts by weight of the dispersion for solution C. Using a wire rod (No. 12), a white paper was coated with the resulting coating solution and the coated white paper was dried and then subjected to a calendering treatment to obtain a thermal sensitive recording paper (coating weight was about 5.5 g/m² on a dry basis).

EXAMPLE 30

In the same manner as in Example 29, except that N-(2-hydroxy)benzoyl-(4-hydroxyphenylthio)acetamide was used in place of N-benzoyl-(4-hydroxyphenylthio)acetamide in the developer dispersion (solution B) of Example 29, a thermal sensitive recording paper was made.

COMPARATIVE EXAMPLE 7

In the same manner as in Example 29, except that 2,4'-dihydroxydiphenylsulfone was used in place of N-benzoyl-(4-hydroxyphenylthio)acetamide in the developer dispersion (solution B) of Example 29, a thermal sensitive recording paper was made.

TEST EXAMPLE 16

Test on Resistance of Background to Humidity and Heat

A portion of each of the thermal sensitive recording papers made in Examples 29 and 30 and Comparative Example 7 was cut out and was used as a test paper. The optical density of the background of each test paper after storing in an incubator controlled humidity and temperature for 24 hours was measured by Macbeth Densitometer (manufactured by Macbeth Co. under the trade name of RD-514, Filter used: #106). The measurement results are shown in Table 19.

TEST EXAMPLE 17

Test on Light Resistance of Images

A portion of each of the thermal sensitive recording papers made in Examples 29 and 30 and Comparative Example 7 was cut out and was used as a test paper. Using a thermal sensitive paper color developing apparatus (manufactured by Ohkura Electric Co., Ltd. under the trade name of Model TH-PMD), the color of each test paper was developed up to the saturated condition. Using a light resistance testing machine (manufactured by Suga Test Instruments Co., Ltd. under the trade name of Ultraviolet Long Life Fade Meter, Model FAL-5), the image density of each test paper after irradiation with ultraviolet light having a wavelength of 380 nm for 48 hours was measured. The measurement results are shown in Table 19.

TABLE 19

|  | Background | | Images | |
| --- | --- | --- | --- | --- |
|  | Original | Resistance to humidity and heat | Original | Light resistance |
| Comparative Example 7 | 0.11 | 0.08 | 1.26 | 0.93 |
| Example 29 | 0.05 | 0.05 | 1.28 | 0.96 |
| Example 30 | 0.08 | 0.10 | 1.29 | 1.19 |

INDUSTRIAL APPLICABILITY

As described above, according to the present invention, there can be provided a novel phenolic compound, and a recording material using the same, which is excellent in storage stability of the background and images, especially light resistance of the images. In particular, the recording material containing a phenolic compound represented by the formula (XII) of the present invention is excellent in light resistance of the images, heat resistance of the images, light resistance of the background, and heat resistance of the background; the recording material containing a phenolic compound represented by the formula (XIV) of the present invention is excellent in light resistance of the images, resistance of the images to plasticizers, resistance of the background to humidity and heat, and heat resistance of the background; the recording material containing a phenolic compound represented by the formula (XV) of the present invention is excellent in light resistance of the images, heat resistance of the images, and resistance of the background to humidity and heat; the recording material containing a phenolic compound represented by the formula (XVI) of the present invention is excellent in light resistance of the images, heat resistance of the images, and resistance of the images to plasticizers; and the recording material containing a phenolic compound represented by the formula (XVII) of the present invention is excellent in light resistance of the images, and resistance of the background to humidity and heat.

What is claimed is:

1. A phenolic compound represented by the formula (I):

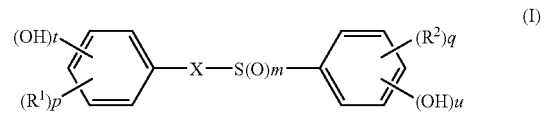

wherein m represents an integer of 0 to 2; $R^1$ and $R^2$ each independently represents a hydroxyl group, a nitro group, a carboxyl group, a halogen atom, a C1–C6 alkyl group, a C1–C6 alkoxy group, a C1–C6 alkoxycarbonyl group, a sulfamoyl group, a phenylsulfamoyl group, a C1–C6 alkylsulfamoyl group, a di(C1–C6) alkylsulfamoyl group, a carbamoyl group, a phenylcarbamoyl group, a C1–C6 alkylcarbamoyl group, a di(C1–C6) alkylcarbamoyl group, an ureide group, a C1–C6 alkylureide group, a di(C1–C6) alkylureide group, a tri(C1–C6) alkylureide group, or a phenylureide group which may have a substituent; p and q each independently represents an integer of 0 to 4, $R^1$ may be the same or different when p is an integer of 2 or more, and $R^2$ may be the same or different when q is an integer of 2 or more; t and u each independently represents 0 or 1 and does not simultaneously represent 0; and X represents a group represented by any of the formulas (II) to (VII);

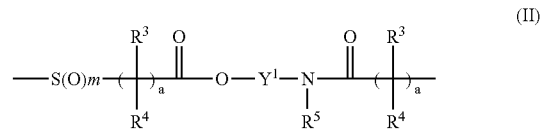

(wherein m is as defined above; $R^3$ and $R^4$ each independently represents a hydrogen atom or a C1–C6 alkyl group; a represents an integer of 1 to 6; $Y^1$ represents a C1–C6 alkylene group, or a group of the following formula:

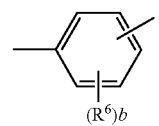

(wherein $R^6$ represents a nitro group, a halogen atom, a C1–C6 alkyl group, a C1–C6 alkoxy group, or a C1–C6 alkoxycarbonyl group; and b represents an integer of 0 to 4 and $R^6$ may be the same or different when b is an integer of 2 or more) or a group selected from the following formulas:

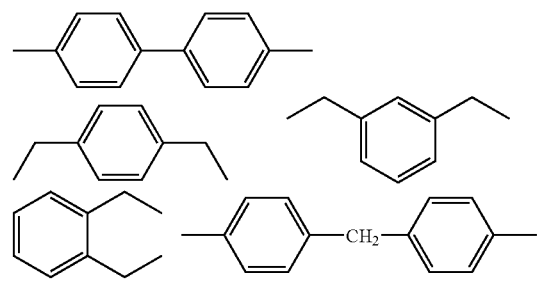

-continued

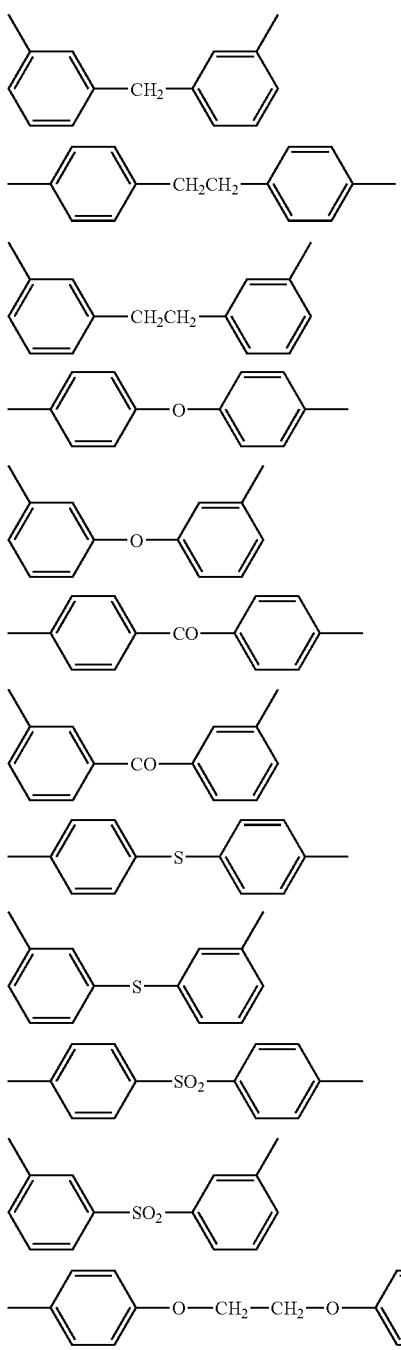

and $R^5$ represents a hydrogen atom, a C1–C6 alkyl group, a phenyl group which may have a substituent, a benzyl group which may have a substituent, or the following formula:

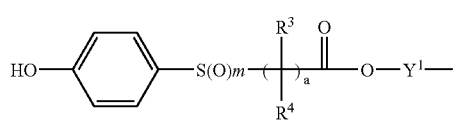

(wherein $R^3$, $R^4$, a, m and $Y^1$ are as defined above)),

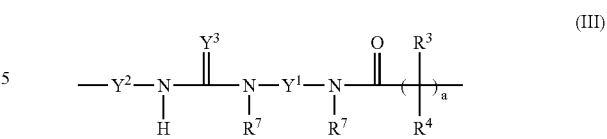

(wherein $R^3$, $R^4$, a and $Y^1$ are as defined above; $R^7$ represents a hydrogen atom, a C1–C6 alkyl group, a phenyl group which may have a substituent, or a benzyl group which may have a substituent; $Y^2$ represents a single bond, CO or $SO_2$; and $Y^3$ represents an oxygen atom or a sulfur atom),

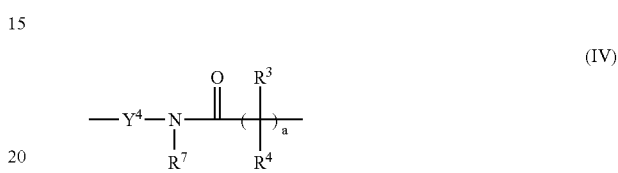

(wherein $R^3$, $R^4$, $R^7$ and a are as defined above; and $Y^4$ represents CO or $SO_2$),

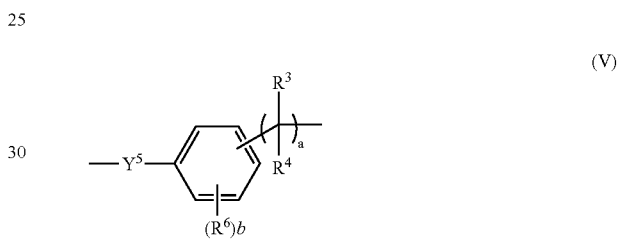

(wherein $R^3$, $R^4$, $R^6$, a and b are as defined above; and $Y^5$ represents CO or $NR^7CO$ ($R^7$ is as defined above)),

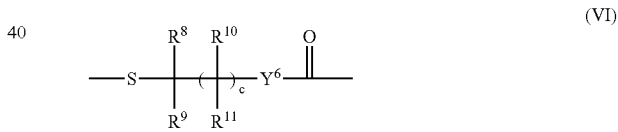

(wherein $R^8$ and $R^9$ each independently represents a hydrogen atom, a C1–C6 alkyl group, or a phenyl group which may have a substituent; $R^{10}$ and $R^{11}$ each independently represents a hydrogen atom or a C1–C6 alkyl group; c represents an integer of 0 to 6; and $Y^6$ represents a single bond or the following formula:

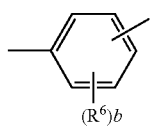

(wherein $R^6$ and b are as defined above)), and

(wherein $Y^7$ represents a single bond or NH; and $Y^8$ represents a single bond or the following formula:

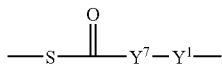

(wherein $Y^{1'}$ represents a group selected from the following formulas:

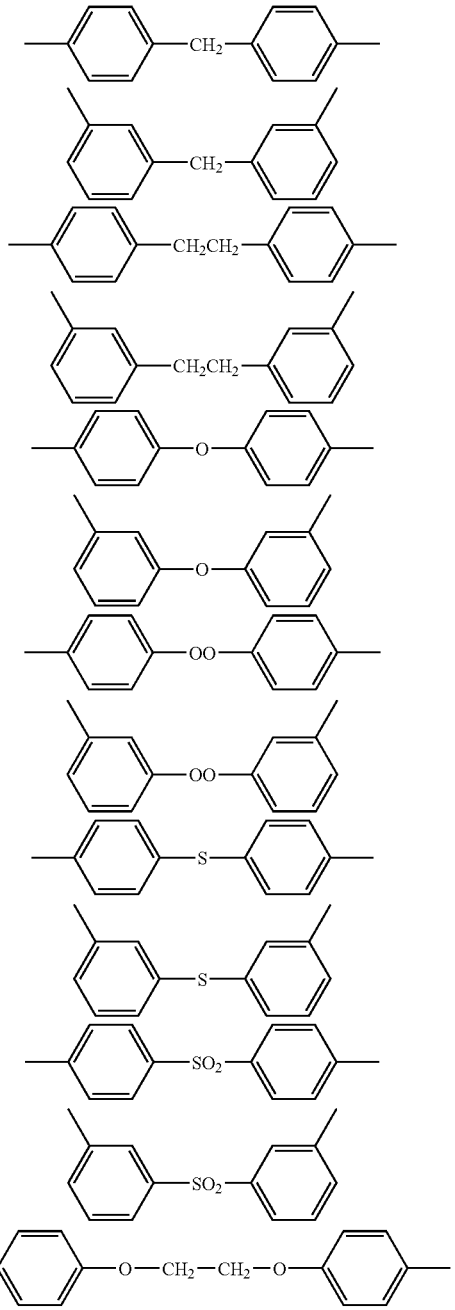

and $Y^7$ are as defined above));
provided that, when X represents a group represented by the formula (VI) or (VII), m represents 0, when X represents a group represented by the formula (II) or (VI), p and q represent 0, t and u represent 1, and both of two hydroxyl groups represent a para-substituting group, when X represents a group represented by the formula (III), (IV) or (VII), q represents 0, u represents 1 and this hydroxyl group represents a para-substituting group, when X represents a group represented by the formula (VII) and $Y^8$ represents the following formula:

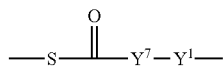

(wherein $Y^{1'}$ and $Y^7$ are as defined above), p represents 0, t represents 1, and this hydroxyl group represents a para-substituting group, and when X represents a group represented by the formula (VII) and $Y^8$ represents a single bond, $Y^7$ represents a single bond.

2. The phenolic compound according to claim 1, wherein X is a group represented by the formula (VIII):

(VIII)

wherein $R^3$, $R^4$ and a are as defined above; and $Y^9$ represents a group represented by any of the formulas (IX) to (XI):

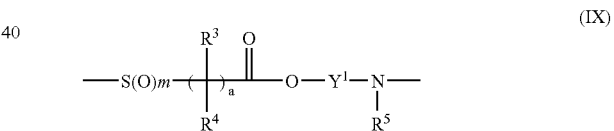

(IX)

(wherein $R^3$, $R^4$, $R^5$, a, m and $Y^1$ are as defined above),

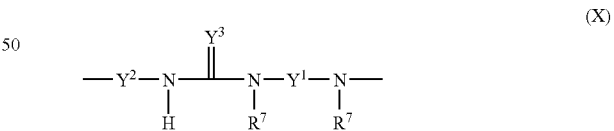

(X)

(wherein $R^7$, $Y^1$, $Y^2$ and $Y^3$ are as defined above), and

(XI)

(wherein $R^7$ and $Y^4$ are as defined above).

3. The phenolic compound according to claim 1, wherein the phenolic compound represented by the formula (I) is a phenolic compound represented by the formula (XII):

(XII)

[chemical structure XII]

wherein R¹ R², R³, R⁴, R⁶, a, b, m, p, q, t, u and Y⁵ are as defined above.

4. The phenolic compound according to claim 1, wherein the phenolic compound represented by the formula (I) is a phenolic compound represented by the formula (XIII):

(XIII)

[chemical structure XIII]

wherein R⁸, R⁹, R¹⁰, R¹¹, c and Y⁶ are as defined above.

5. The phenolic compound according to claim 1, wherein the phenolic compound represented by the formula (I) is a phenolic compound represented by the formula (XIV):

(XIV)

[chemical structure XIV]

wherein Y⁷ is as defined above; and Y¹⁰ represents the following formula:

[chemical structure]

(wherein R¹, p and t are as defined above) or the following formula:

[chemical structure]

(wherein Y¹' and Y⁷ are as defined above) provided that when Y¹⁰ represents the following formula:

[chemical structure]

(wherein R¹, p and t are as defined above), Y⁷ represents a single bond.

6. The phenolic compound according to claim 1, wherein the phenolic compound represented by the formula (I) is a phenolic compound represented by the formula (XV):

(XV)

[chemical structure XV]

wherein R³, R⁴, R⁵, a, m and Y¹ are as defined above.

7. The phenolic compound according to claim 1, wherein the phenolic compound represented by the formula (I) is a phenolic compound represented by the formula (XVI):

(XVI)

[chemical structure XVI]

wherein R¹, R³, R⁴, R⁷, a, m, p, t, Y¹, Y² and Y³ are as defined above.

8. The phenolic compound according to claim 1, wherein the phenolic compound represented by the formula (I) is a phenolic compound represented by the formula (XVII):

(XVII)

[chemical structure XVII]

wherein R¹, R³, R⁴, R⁷, a, m, p, t and Y⁴ are as defined above.

* * * * *